(12) United States Patent
Walker et al.

(10) Patent No.: US 6,524,799 B1
(45) Date of Patent: Feb. 25, 2003

(54) DNA ENCODING SPARC-RELATED PROTEINS

(75) Inventors: Michael G. Walker, Sunnyvale, CA (US); Randi E. Krasnow, Stanford, CA (US)

(73) Assignee: Incyte Genomics, Inc., Palo Alto, CA (US)

(*) Notice: Subject to any disclaimer, the term of this patent is extended or adjusted under 35 U.S.C. 154(b) by 58 days.

(21) Appl. No.: 09/642,703

(22) Filed: Aug. 16, 2000

Related U.S. Application Data

(63) Continuation-in-part of application No. 09/349,015, filed on Jul. 7, 1999.
(51) Int. Cl.[7] .......................... C12Q 1/68; C12P 21/06; C12N 1/19; C12N 5/10; C07H 21/04
(52) U.S. Cl. .................. 435/6; 435/69.1; 435/252.3; 435/320.1; 435/325; 536/23.5
(58) Field of Search .................. 435/252.3, 69.2, 435/320.1, 425, 6, 69.1, 325; 536/23.5

(56) References Cited

PUBLICATIONS

Lane, et al., "The biology of SPARC, a protein that modulates cell–matrix interactions" FASEB J 8:163–173(1994).
Motamed, K., "Molecules in focus SPARC (osteonectin/BM–40)", *Int. J. Biochem Cell Biol*, 31:1363–1366 (1999).
Raines,et al., "The Extracellular glycoprotein SPARC interacts with platelet–derived growth factor (PDGF)–AB and –BB and inhibits the binding of PDGF to its receptors", *Proc Natl Acad Sci*, 89:1281–1285 (1992).
Funk et al., "The $Ca^{2+}$–binding glycoprotein SPARC modulates cell cycle progression in bovine aortic endothelial cells", Proc Natl Acad Sci.,: 2648–2652 (1991).
Watson, et al., TGF–β1 and 25–Hyfroxycholesterol Stimulate Osteoblast–like Vascular Cells to Calcify, J. Clin Invest 93:2106–2113(1994).
Vajkoczy et al., "Targeting Angiogenesis Inhibits Tumor Infiltration and Expression of the Pro–Invasive Protein SPARC", Int J. Cancer 87:261–268 (2000).
Nakamura et al., Enhancement of SPARC (Osteonectin) Synthesis in Arthritic Cartilage, Arthritis and Rheumatism 39:539–551 (1996).
Gilles et al., "SPARC/Osteonectin Induces Matrix Metalloproteinase 2 Activation in Human Breast Cancer Cell Lines[1]", Cancer Res 58:5529–55326 (1998).
Porter et al., "Distribution of SPARC in Normal and Neoplastic Human Tissue[1]", J Histochem Cytochem 43:791–800 (1995).
Brown et al., "Activation of SPARC Expression in Reactive Stroma Associated with Human Epithelial Ovarian Cancer[1]", Gynecol Oncol 75:25–33 (1999).
Thomas et al., "Differential Expression of Osteonectin/SPARC during Human Prostate Cancer Progression[1]", Clin Cancer Res 6:1140–1149 (2000).
Unemori et al., "Connective tissue Metabolism including Cytokines in Scleroderma", Curr Opin Rheumatol #:953–959 (1991).
Kantorow et al., "Increased Expression of Osteonectin/SPARC mRNA and Protein in Age–Related Human Cataracts and Spatial Expression in the Normal Human lens", Mol Vis 6:24–29 (2000).
Bassuk et al., "Induction of TGF–[beta]1 by the matricellular protein SPARC in a rat model of glomerulonephritis", Kidney Int 57:117–128 (2000).
Poleev, A. et al., (Direct Submission) NCBI Accession No. AAD41590 (GI 5305327), Feb. 6, 1999.
Bolton et al., "The Labelling of Proteins to High Specifc Radioactivities by Conjugation to a $^{125}I$–Containing Acylating Agent", Biochem J 133:529–539 (1973).

*Primary Examiner*—Elizabeth Slobodyansky
(74) *Attorney, Agent, or Firm*—Incyte Genomics, Inc.

(57) ABSTRACT

The invention provides mammalian cDNAs which encode mammalian SPARC-related proteins. It also provides for the use of the cDNA, fragments, complements, and variants thereof and of the encoded protein, portions thereof and antibodies thereto for diagnosis and treatment of atherosclerosis and cell proliferative disorders. The invention additionally provides expression vectors and host cells for the production of the proteins and transgenic model systems.

12 Claims, 22 Drawing Sheets

Figure 1A

```
5'  CGA GGG CGG ACG CAA AGA ACG CGG AGG ACC TCT GGG TGC CTG CAG GGG AGC TGC
      9          18          27          36          45          54

TCC AGC CGG GCC GCC GGG AGC GGT GAG AGC ATC GCG CAG CCG CCC CTC CAC
     63          72          81          90          99         108

GCG CCC CAG CCC CAG CCG TCG CCC ACT GGG CTC CGG CTG TGC CAG GGC
    117         126         135         144         153         162

GCA CGC GGC CGA TCT CCC GCT CCC ACC TCC GCC ACC ATG CTG CTC CCC
    171         180         189         198         207      M   L   L   P
                                                        216

CAG CTC TGG CTG CCG CTG CTC GGG CTG GCT CTC CCG CCG GTG CCC GCT CAG
     Q   L   W   L   P   L   L   G   L   A   L   P   P   V   P   A   Q
    225         234         243         252         261         270

AAG TTC TCG GCG CTC ACG TTT TTG AGA GTG GAT CAA GAT AAA GAC AAG GAT TGT
     K   F   S   A   L   T   F   L   R   V   D   Q   D   K   D   K   D   C
    279         288         297         306         315         324
```

```
AGC TTG GAC TGT GCG GGT TCG CCC CAG AAA CCT CTC TGC GCA TCT GAC GGA AGG
 S   L   D   C   A   G   S   P   Q   K   P   L   C   A   S   D   G   R
333         342         351         360         369         378

ACC TTC CTT TCC CGT TGT GAA TTT CAA CGT GCC AAG TGC AAA GAT CCC CAG CTA
 T   F   L   S   R   C   E   F   Q   R   A   K   C   K   D   P   Q   L
387         396         405         414         423         432

GAG ATT GCA TAT CGA GGA AAC TGC AAA GAC GTG TCC AGG TGT GTG GCC GAA AGG
 E   I   A   Y   R   G   N   C   K   D   V   S   R   C   V   A   E   R
441         450         459         468         477         486

AAG TAT ACC CAG GAG CAA GCC CGG AAG GAG TTT CAG CAA GTC TTC ATT CCT GAG
 K   Y   T   Q   E   Q   A   R   K   E   F   Q   Q   V   F   I   P   E
495         504         513         522         531         540

TGC AAT GAC GAC GGC ACC TAC AGT CAG GTC CAG TGT CAC AGC TAC ACG GGA TAC
 C   N   D   D   G   T   Y   S   Q   V   Q   C   H   S   Y   T   G   Y
549         558         567         576         585         594
```

```
603                612                621                630                639                648
TGC  TGG  TGC      GTC  ACG  CCC      AAC  GGG  AGG      CCC  ATC  AGC      GGC  ACT  GCC      GTG  GCC  CAC
 C    W    C        V    T    P        N    G    R        P    I    S        G    T    A        V    A    H 657                666                675                684                693                702
AAG  ACG  CCC      CGG  TGC  CCG      GGT  TCC  GTA      AAT  GAA  AAG      TTA  CCC  CAA      CGC  GAA  GGC
 K    T    P        R    C    P        G    S    V        N    E    K        L    P    Q        R    E    G 711                720                729                738                747                756
ACA  GAA  GAT      ATT  GCC  GCA      TCA  CGT  GCT      CCA  GCG  TTG      GAG  ACT  CAG      CCT  CAA  GGA
 T    E    D        I    A    A        S    R    A        P    A    L        E    T    Q        P    Q    G 765                774                783                792                801                810
GAT  GAA  GAT      ATT  GCA  GAT      GCC  TCA  CGT      TAC  CCT  ACC      CTT  TGG  ACT      GAA  CAG  GTT  AAA
 D    E    D        I    A    D        A    S    R        Y    P    T        L    W    T        E    Q    V    K 819                828                837                846                855                864
AGT  CGG  CAG      AAC  AAA  ACC      AAT  TCA  AAT      AAG  TCA  GTG      TCC  TGT  GAC      CAA  GAG  CAC
 S    R    Q        N    K    T        N    S    N        K    S    V        S    C    D        Q    E    H
```

```
      873       882       891       900       909       918
CAG   TCT   GCC   CTG   GAG   GCC   AAG   CAG   CCC   AAG   AAC   GAC   AAT   GTG   GTG   ATC   CCT
---   ---   ---   ---   ---   ---   ---   ---   ---   ---   ---   ---   ---   ---   ---   ---   ---
 Q     S     A     L     E     A     K     Q     P     K     N     D     N     V     V     I     P 927       936       945       954       963       972
GAG   TGT   GCG   CAC   GGC   GGC   CTC   TAC   AAG   CAG   CCA   GTG   CAG   TGC   CAC   CCC   TCC   ACG   GGG
---   ---   ---   ---   ---   ---   ---   ---   ---   ---   ---   ---   ---   ---   ---   ---   ---   ---   ---
 E     C     A     H     G     G     L     Y     K     Q     P     V     Q     C     H     P     S     T     G 981       990       999      1008      1017      1026
TAC   TGC   TGG   CAG   CTG   GTG   GAC   ACG   GGG   CGC   CCC   ATT   CCC   GGC   ACA   TCC   ACA
---   ---   ---   ---   ---   ---   ---   ---   ---   ---   ---   ---   ---   ---   ---   ---   ---
 Y     C     W     Q     L     V     D     T     G     R     P     I     P     G     T     S     T 1035      1044      1053      1062      1071      1080
AGG   TAC   GAG   CAG   CCG   AAA   TGT   GAC   AAC   ACG   GCC   AGG   GCC   CAC   CCA   GCC   AAA   GCC
---   ---   ---   ---   ---   ---   ---   ---   ---   ---   ---   ---   ---   ---   ---   ---   ---   ---
 R     Y     E     Q     P     K     C     D     N     T     A     R     A     H     P     A     K     A 1089      1098      1107      1116      1125      1134
CGG   GAC   CTG   TAC   AAG   GGC   CGC   CAG   CTA   CAA   GGT   TGT   CCG   GGT   GCC   AAA   AAG   CAT
---   ---   ---   ---   ---   ---   ---   ---   ---   ---   ---   ---   ---   ---   ---   ---   ---   ---
 R     D     L     Y     K     G     R     Q     L     Q     G     C     P     G     A     K     K     H
```

Figure 1D

```
     1143      1152      1161      1170      1179      1188
GAG  TTT  CTG  ACC  AGC  GTT  CTG  GAC  GCG  CTG  TCC  GAC  ATG  GTC  CAC  GCC  GCC
 E    F    L    T    S    V    L    D    A    L    S    T    D    M    V    H    A    A 1197      1206      1215      1224      1233      1242
TCC  GAC  CCC  TCC  TCG  TCA  GGC  AGG  CTC  TCA  GAA  CCC  GAC  CCC  AGC  CAT  ACC
 S    D    P    S    S    S    G    R    L    S    E    P    D    P    S    H    T 1251      1260      1269      1278      1287      1296
CTA  GAG  GAG  CGG  GTG  GTG  CAC  TGG  TAC  TTC  AAA  CTA  CTG  GAT  AAA  AAC  TCC  AGT
 L    E    E    R    V    V    H    W    Y    F    K    L    L    D    K    N    S    S 1305      1314      1323      1332      1341      1350
GGA  GAC  ATC  GGC  AAA  AAG  GAA  ATC  AAA  CCC  TTC  AAG  AGG  TTC  CTT  CGC  AAA  AAA
 G    D    I    G    K    K    E    I    K    P    F    K    R    F    L    R    K    K 1359      1368      1377      1386      1395      1404
TCA  AAG  CCC  AAA  AAA  TGT  GTG  AAA  AAG  TTT  GTT  GAA  TAC  TGT  GAA  TAC  GTG  AAT  AAT
 S    K    P    K    K    C    V    K    K    F    V    E    Y    C    E    Y    V    N    N
```

Figure 1E

```
         1413        1422        1431        1440        1449        1458
GAC AAA TCC ATC TCC GTA CAA GAA CTG ATG GGC TGC CTG GGC GTG GCG AAA GAG
 D   K   S   I   S   V   Q   E   L   M   G   C   L   G   V   A   K   E
         1467        1476        1485        1494        1503        1512
GAC GGC AAA GCG GAC ACC AAG AAA CGC CAC ACC CCC AGA GGT CAT GCT GAA AGT
 D   G   K   A   D   T   K   K   R   H   T   P   R   G   H   A   E   S
         1521        1530        1539        1548        1557        1566
ACG TCT AAT AGA CAG CCA AGG AAA CAA GGA TAA ATG GCT CAT ACC CCG AAG GCA
 T   S   N   R   Q   P   R   K   Q   G   *
         1575        1584        1593        1602        1611        1620
GTT CCT AGA CAC ATG GGA AAT TTC CCT CAC CAA AGA GCA ATT AAG AAA ACA AAA
         1629        1638        1647        1656        1665        1674
ACA ACA CAT AGT ATT TGC ACT ATT TGC ACT TTG TAC TTT AAA TGT AAA TTC ACT TTG TAG
         1683        1692        1701        1710        1719        1728
AAA TGA GCT ATT TAA ACA GAC TGT TTT AAT CTG TGA AAA TGG AGA GCT GGC TTC
         1737        1746        1755        1764        1773        1782
AGA AAA TTA ATC ACA TAC AAT GTA TGT GTC CTC TTT TGA CCT TGG AAA TCT GTA
```

Figure 1F

```
                1791      1800      1809      1818      1827      1836
                TGT GGT GGA GAA GTA TTT GAA TGC ATT TAG GCT TAA TTT CTT CGC CTT CCA CAT
                1845      1854      1863      1872      1881      1890
                GTT AAC AGT AGA GCT CTA TGC ACT CCG GCT GCA ATC GTA TGG CTT TCT CTA ACC
                1899      1908      1917      1926      1935      1944
                CCT GCA GTC ACT TCC AGA TGC CTG TGC TTA CAG CAT TGT GGA ATC ATG TTG GAA
                1953      1962      1971      1980      1989      1998
                GCT CCA CAT GTC CAT GGA AGT TTG TGA TGT ACG GCC GAC CCT ACA GGC AGT TAA
                2007      2016      2025      2034      2043      2052
                CAT GCA TGG GCT GGT TTG TTT CTT GGG ATT TTC TGT TAG TTT GTC TTG TTT TGC
                2061      2070      2079      2088      2097      2106
                TTT CCA GAG ATC TTG CTC ATA CAA TGA ATC ACG CAA CCA CTA AAG CTA TCC AGT
                2115      2124      2133      2142      2151      2160
                TAA GTG CAG GTA GTT CCC CTG GAG GAA ATA ATA TTT TCA AAC TGT CGT TGG TGT
                2169      2178      2187      2196      2205      2214
                GAT ACT TTG GCT CAA AGG ATC TTT GCT TTT CCA TTT TAA GCT TCT GTT TTG AGT
                2223      2232      2241      2250      2259      2268
                TTT GCC CTG GGG CTT GAA TGA GTC CCA GAG AGT CGT TCG GAT GGT GGG AGG CTG
```

Figure 1G

```
              2277           2286           2295           2304           2313           2322
CCT AGG AGG CAG TAA ATC CAG TCA CAG TGC CTG GGA GGG GCC CAT CCT TCC AAA
2331           2340           2349           2358           2367           2376
ATG TAA ATC CAG TCG CGG TGT GAC CGA GCT GGC TAA CAG GCT TGT CTG CCT GGT
              2385           2394           2403           2412           2421           2430
TTT CCT ACA CGT GGA CAT TAT TCT CCT GAT CCT CCT ACC TGG TCC ACC CCA
2439           2448           2457           2466           2475           2484
GGG CTA CCG GAA GGT AAA ATC TTC ACC TGA ACC AAT TAT GAG CAG TCT CCT TAC
              2493           2502           2511           2520           2529           2538
TGA AGG TAC AGC CGG ATA CGT GGT GCC CCC GGG GCT GGT GTT GGC AGC CGG GGG
2547           2556           2565           2574           2583           2592
GAG GTG CCT GAG GGT CCC CAC GGT TCC TTT CTG CTT TTC TGA ATG CAT CAA GGG
              2601           2610           2619           2628           2637           2646
TAC GAG AAC TTG CCA ATG GGA AAT TCA TCC GAG TGG CAC TGG CAG AGA AGG ATA
2655           2664           2673           2682           2691           2700
GGA GTG GAA TGC CCA CAC AGT GAC CAA CAG AAC TGG TCT GCG TGC ATA ACC AGC
              2709           2718           2727           2736           2745           2754
TGC CAC CCT CAG GCC TGG GCC CCA GAG CTC AGG GCA CCC AGT GTC TTA AGG AAC
```

Figure 1H

```
                                                2763                    2772                    2781                    2790                    2799                    2808
CAT TTG GAG GAC AGT CTG AGA GCA GGA ACT TCA AGC TGT GAT TCT ATC TCG GCT
        2817                    2826                    2835                    2844                    2853                    2862
CAG ACT TTT GGT TGG AAA AAG ATC TTC ATG GCC CCA AAT CCC CTG AGA CAT GCC
        2871                    2880                    2889                    2898                    2907                    2916
TTG TAG AAT GAT TTT GTG ATG TTG TGA TGC TTG TGG AGC ATC GCG TAA GGC TTC
        2925                    2934                    2943                    2952                    2961                    2970
TTG CTT ATT TAA ACT GTG CAA GGT AAA AAT CAA GCC TTT GGA GCC ACA GAA CCA
        2979                    2988                    2997                    3006                    3015                    3024
GCT CAA GTA CAT GCC AAT GTT GTT TAA GAA ACA GTT ATG ATC CTA AAC TTT TTG
        3033                    3042                    3051                    3060                    3069                    3078
GAT AAT CTT TTA TAT TTC TGA CCT TTG AAT TTA ATC ATT GTT CTT AGA TTA AAA
        3087                    3096                    3105                    3114                    3123                    3132
TAA AAT ATG CTA TTG AAA CTA AAA AAA AAA AAA AAG AGG GGA GAA GAA AAA AAA
GG 3'
```

```
5'                9              18              27              36              45              54
    T CCC        TGA CCG         CGA GCT         CTG CGA         GCC CCC         GCC GGA         CCA CCC         GCT CCC
                 63              72              81              90              99              108
    CGC CTG      CGC GAG         GGC CCC         GAG CGA         AAG GAA         AGG CGC         GCT GTG         CGC CCC
                 117             126             135             144             153             162
    GCG GAG      CCC GCG         AAC CCC         GCT CGC         TGC CGG         CTG CCC         AGC CTG         GGC ACC ATG
                                                                                                                         M
                 171             180             189             198             207             216
    CTG CCC      GCG CGC         TGC CTG         CAC TTG         CTC ACG         CCC CAC         TTG CTG         GTG TTG GTG
      L           P   A           R   C           L   H           L   T           P   H           L   L           V   L   V
                 225             234             243             252             261             270
    CAG CTG      TCC CCT         GCT CGC         GGC CAC         CGC ACC         ACA GGC         CCC AGG         TTT CTA ATA AGT
      Q   L       S   P           A   R           G   H           R   T           T   G           P   R           F   L   I   S
                 279             288             297             306             315             324
    GAC CGT      GAC CCA         CAG TGC         AAC CTC         CAC TGC         TCC AGG         ACT CAA         CCC AAA CCC ATC
      D   R       D   P           Q   C           N   L           H   C           S   R           T   Q           P   K   P   I
```

| | | | | | | | | |
|---|---|---|---|---|---|---|---|---|
| | 333 | | 342 | | 351 | 360 | 369 | 378 |
| TGT | GCC | TCT | GAT | GGC | TCC | TAC | ATG | GAG | TAC | CAG | CGA | GCC | AAG |
| C | A | S | D | G | S | Y | M | E | Y | Q | R | A | K |
| | 387 | | 396 | | 405 | 414 | 423 | 432 |
| TGC | CGA | GAC | CCG | ACC | CTG | GGC | GTG | CAT | CGA | GGT | AGA | TGC | AAA | GAT | GCT | GGC |
| C | R | D | P | T | L | G | V | H | R | G | R | C | K | D | A | G |
| | 441 | | 450 | | 459 | 468 | 477 | 486 |
| CAG | AGC | AAG | TGT | CGC | CTG | GAG | CGG | GCT | CAA | CTG | GAG | CAA | GCC | AAG | AAG | CCT |
| Q | S | K | C | R | L | E | R | A | Q | L | E | Q | A | K | K | P |
| | 495 | | 504 | | 513 | 522 | 531 | 540 |
| CAG | GAA | GCT | GTG | TTT | GTC | CCA | GAG | TGT | GGC | GAG | GAT | GGC | TCC | TTT | ACC | CAG | GTG |
| Q | E | A | V | F | V | P | E | C | G | E | D | G | S | F | T | Q | V |
| | 549 | | 558 | | 567 | 576 | 585 | 594 |
| CAG | TGC | CAT | ACT | TAC | ACT | GGG | TAC | TGC | TGG | TGT | GTC | ACC | CCG | GAT | GGG | AAG | CCC |
| Q | C | H | T | Y | T | G | Y | C | W | C | V | T | P | D | G | K | P |

```
603                 612             621             630             639             648
ATC AGT GGC TCT TCT GTG CAG AAT AAA ACT CCT GTA TGT TCA GGT TCA GTC ACC
 I   S   G   S   S   V   Q   N   K   T   P   V   C   S   G   S   V   T 657                 666             675             684             693             702
GAC AAG CCC TTG AGC CAG GGT AAC TCA GGA AGG AAA GAT GAC GGG TCT AAG CCG
 D   K   P   L   S   Q   G   N   S   G   R   K   D   D   G   S   K   P 711                 720             729             738             747             756
ACA CCC ATG GAG ACC CAG CCG GTG TTC GAT GGA GAT GAA ATC ACA GCC CCA
 T   P   M   E   T   Q   P   V   F   D   G   D   E   I   T   A   P 765                 774             783             792             801             810
ACT CTA TGG ATT AAA CAC TTG GTG ATC AAG GAC TCC AAA CTG AAC ACC AAC
 T   L   W   I   K   H   L   V   I   K   D   S   K   L   N   T   N 819                 828             837             846             855             864
ATA AGA AAT TCA GAG AAA GTC TAT TCG TGT GAC CAG GAG AGG CAG AGT GCC CTG
 I   R   N   S   E   K   V   Y   S   C   D   Q   E   R   Q   S   A   L
```

```
         873        882        891        900        909        918
GAA GAG GCC CAG CAG AAT CCC CGT GAG GGT ATT GTC ATC CCT GAA TGT GCC CCT
 E   E   A   Q   Q   N   P   R   E   G   I   V   I   P   E   C   A   P 927        936        945        954        963        972
GGG GGA CTC TAT AAG CCA GTG CAA TGC CAC CAG TCC ACT GGC TAC TGC TGG TGT
 G   G   L   Y   K   P   V   Q   C   H   Q   S   T   G   Y   C   W   C 981        990        999       1008       1017       1026
GTG CTG GTG GAC ACA GGG CGC CCG CTG CCT GGG ACC TCC ACA CGC TAC GTG ATG
 V   L   V   D   T   G   R   P   L   P   G   T   S   T   R   Y   V   M 1035       1044       1053       1062       1071       1080
CCC AGT TGT GAG AGC GAC GCC AGG AAG ACT ACA GAG GCG GAT GAC CCC TTC
 P   S   C   E   S   D   A   R   K   T   T   E   A   D   D   P   F 1089       1098       1107       1116       1125       1134
AAG GAC AGG GAG CTA CCA GGC TGT CCA GAA GGG AAG ATG GAG TTT ATC ACC
 K   D   R   E   L   P   G   C   P   E   G   K   M   E   F   I   T
```

Figure 2D

```
           1143        1152        1161        1170        1179        1188
AGC CTA GAT GCT CTC ACC ACT GAC ATG GTT CAG GCC ATT AAC TCA GCA GCG
 S   L   D   A   L   T   T   D   M   V   Q   A   I   N   S   A   A 1197        1206        1215        1224        1233        1242
CCC ACT GGA GGT GGG AGG TTC TCA GAG CCA GAC CCC AGC CAC ACC CTG GAG GAG
 P   T   G   G   G   R   F   S   E   P   D   P   S   H   T   L   E   E 1251        1260        1269        1278        1287        1296
CGG GTA CAC TGG TAT TTC AGC CAG CTG GAC AGC AAT AGC AGC AAC AAC ATT
 R   V   H   W   Y   F   S   Q   L   D   S   N   S   S   N   N   I 1305        1314        1323        1332        1341        1350
AAC AAG GAG ATG AAG CCC TTC AAG CGC TAC GTG AAG AAA GCC AAG CCC
 N   K   E   M   K   P   F   K   R   Y   V   K   K   A   K   P 1359        1368        1377        1386        1395        1404
AAG AAA TGT GCC CGG CGT TTC ACC GAC TAC TGT GAC CTG AAC AAA GAC AAG GTC
 K   K   C   A   R   R   F   T   D   Y   C   D   L   N   K   D   K   V
```

Figure 2E

```
      1413           1422           1431           1440           1449           1458
ATT TCA CTG CCT GAG CTG AAG GGC TGC CTG GGT GTT AGC AAA GAA GGA CGC CTC
--- --- --- --- --- --- --- --- --- --- --- --- --- --- --- --- --- ---
 I   S   L   P   E   L   K   G   C   L   G   V   S   K   E   G   R   L 1467           1476           1485           1494           1503           1512
GTC TAA GGA GCA GAA AAC CCA AGG GCA GGT GGA GAG TCC AGG GAG GCA GGA TGG
---
 V 1521           1530           1539           1548           1557           1566
ATC ACC AGA CAC CTA ACC TTC AGC GTT GCC CAT GGC CCT GCC ACA TCC CGT GTA 1575           1584           1593           1602           1611           1620
ACA GTG GTG CCC ACC ATG TTT GCA CTT TTA ATA ACT CTT ACT TGC GTG TTT 1629           1638           1647           1656           1665           1674
TGT TTT TGG TTT CAT TTT AAA ACA CCA ATA TCT AAT ACC ACA GTG GGA AAA GGA 1683           1692           1701           1710           1719           1728
AAG GGA AGA AAG ACT TTA TTC TCT CTC TTA TTG GGA GTT TTT GGA TCT GCT ACT 1737           1746           1755           1764           1773           1782
GAC AAC TTT TAG AGG GTT TTG GGG TGG GGG AGG GTG TTG GGG CTG AGA 1791           1800           1809           1818           1827           1836
AGA AAG AGA TTT ATA TGC TGT ATA TAA ATA TAT ATG TAA ATT GTA TAG TTC TTT
```

Figure 2F

```
              1845       1854       1863       1872       1881       1890
          TGT ACA GGC ATT GGC ATT GCT GTT TGT TTA TTT CTC TCC CTC TGC CTG CTG TGG
              1899       1908       1917       1926       1935       1944
          GTG GTG GGC ACT CTG GAC ACA TAG TCC AGC TTT CTA AAA TCC AGG ACT CTA TCC
              1953       1962       1971       1980       1989       1998
          TGG GCC TAC TAA ACT TCT GTT TGG AGA CTG ACC CTT GTG TAT AAA GAC GGG AGT
              2007       2016       2025       2034       2043       2052
          CCT GCA ATT GTA CTG CGG ACT CCA CGA GTT CTT TTC TGG TGG GAG GAC TAT ATT
              2061       2070       2079       2088       2097       2106
          GCC CCA TGC CAT TAG TTG TCA AAA TTG ATA AGT CAC TTG GCT CTC GGC CTT GTC
              2115       2124       2133       2142       2151       2160
          CAG GGA GGT TGG GCT AAG GAG AGA TGG AAA CTG CCC TGG GAG AGG AAG GGA GTC
              2169       2178       2187       2196       2205       2214
          CAG ATC CCA TGA ATA GCC CAC ACA GGT ACC GGC TCT CAG AGG GTC CGT GCA TTC
              2223       2232       2241       2250       2259       2268
          CTG CTC TCC GGA CCC CCA AAG GGC CCA TTG GTG GGT GCA CCA GTA TCT TAG
              2277       2286       2295       2304       2313       2322
          TGA CCC TCG GAG CAA ATT ATC CAC AAA GGA TTT GCA TTA CGT CAC TCG AAA CGT
```

Figure 2G

```
        2331                    2340                    2349                    2358                    2367                    2376
TTT CAT CCA TGC TTA GCA TCT ACT CTG TAT AAC GCA TGA GAG GGG AGG CAA AGA
        2385                    2394                    2403                    2412                    2421                    2430
AGA AAA AGA CAC ACA GAA GGG CCT TTA AAA AAG TAG ATA TTT AAT ATC TAA GCA
        2439                    2448                    2457                    2466                    2475                    2484
GGG GAG GGG ACA GGA CAG AAA GCC TGC ACT GAG GGG TGC GGT GCC AAC AGG GAA
        2493                    2502                    2511                    2520                    2529                    2538
ACT CTT CAC CTC CCT GCA AAC CTA CCA GTG AGG CTC CCA GAG ACG CAG CTG TCT
        2547                    2556                    2565                    2574                    2583                    2592
CAG TGC CAG GGG CAG ATT GGG TGT GAC CTC TCC ACT CCT CCA TCT CCT GCT GTT
        2601                    2610                    2619                    2628                    2637                    2646
GTC CTA GTG GCT ATC ACA GGC CTG GGT GGG TGG GTT GGG GGA GGT GTC AGT CAC
        2655                    2664                    2673                    2682                    2691                    2700
CTT GTT GGT AAC ACT AAA GTT GTT TTG TTT TAA AAA CCC AAT ACT GAG
        2709                    2718                    2727                    2736                    2745                    2754
GTT CTT CCT GTT CCC TCA AGT TTT CTT ATG GGC TTC CAG GCT TTA AGC TAA TTC
        2763                    2772                    2781                    2790                    2799                    2808
CAG AAG TAA AAC TGA TCT TGG GTT TCC TAT TCT GCC TCC CCT AGA AGG GCA GGG
```

Figure 2H

```
                2817      2826      2835      2844      2853      2862
GTG ATA ACC CAG CTA CAG GGA AAT CCC GGC CCA ACT TTC CAC AGG CAT CAC AGG 2871      2880      2889      2898      2907      2916
CAT CTT CCG CGG ATT CTA GGG TGG GCT GCC CAG CCT TCT GGT CTG AGG CGC AGC 2925      2934      2943      2952      2961      2970
TCC CTC TGC CCA GGT GCT GTG CCT ATT CAA GTG GCC TTC AGG CAG AGC AGC AAG 2979      2988      2997      3006      3015      3024
TGG CCC TTA GCG CCC CTT CCC ATA AGC AGC TGT GGT GGC AGT GAG GGA GGT TGG 3033      3042      3051      3060      3069      3078
GTA GCC CTG GAC TGG TCC CCT CCT CAG ATC ACC CTT GCA AAT CTG GCC TCA TCT 3087      3096      3105      3114      3123      3132
TGT ATT CCA ACC CGA CAT CCC TAA AAG TAC CTC CAC CCG TTC CGG GTC TGG AAG 3141      3150      3159      3168      3177      3186
GCG TTG GCA CCA CAA GCA CTG TCC CTG TGG GAG GAG CAC AAC CTT CTC GGG ACA 3195      3204      3213      3222      3231      3240
GGA TCT GAT GGG GTC TTG GGC TAA AGG AGG TCC CTG CTG TCC TGG AGA AAG TCC 3249      3258      3267      3276      3285      3294
TAG AGG TTA TCT CAG GAA TGA CTG GTG GCC CTG CCC CAA CGT GGA AAG GTG GGA
```

Figure 2I

```
                    3303                3312                3321                3330                3339                3348
              AGG AAG CCT TCT CCC ATT AGC CCC AAT GAG AGA ACT CAA CGT GCC GGA GCT GAG
                    3357                3366                3375                3384                3393                3402
              TGG GCC TTG CAC GAG ACA CTG GCC CCA CTT TCA GGC CTG GAG GAA GCA TGC ACA
                    3411                3420                3429                3438                3447                3456
              CAT GGA GAC GGC GCC TGC CTG TAG ATG TTT GGA TCT TCG AGA TCT CCC CAG GCA
                    3465                3474                3483                3492                3501                3510
              TCT TGT CTC CCA CAG GAT CGT GTG TGT AGG TGG TGT TGT GTG GTT TTC CTT TGT
                    3519                3528                3537                3546                3555                3564
              GAA GGA GAG AGG GAA ACT ATT TGT AGC TTG TTT TAT AAA AAA TAA AAA ATG GGT
                    3573
              AAA TCT TGA AAA 3'
```

Figure 2J

```
1    ML- - - - - - LPQLCWLPL- - LLVLVQL   LLAGLLPPVPAQ    2617724
1    MLPARCARLLTPHL- - LLVLVQLSPARGH                      6899373
1    MLPAR-VRLLTPHL- - LLVLVQLSPAGGH                      g5305327

23   KFSALTFLRVDQDKDKDCSLDCAGSPQKPL                       2617724
28   RTTGPRFL- -ISDRDPQCNLHCSRTQPKPI                      6899373
27   RTTGPRFL- -ISDRDPPCNPHCPRTQPKPI                      g5305327

53   CASDGRTFLSRCEFQRAKCKDPQLEIAYRG                       2617724
56   CASDGRSYESMCEYQRAKCRDPTLGVVHRG                       6899373
55   CASDGRSYESMCEYQRAKCRDPALAVVHRG                       g5305327

83   NCKDV- -SRCVAERKYTQEQARKEFQQVFI                      2617724
86   RCKDAGQSKCRLERAQALEQAKKPQEAVFV                       6899373
85   RCKDAGQSKCRLERAQALEQAKKPQEAVFV                       g5305327

111  PECNDDGTYSQVQCHSYTGYCWCVTPNGRP                       2617724
116  PECGEDGSFTQVQCHTYTGYCWCVTPDGKP                       6899373
115  PECGEDGSFTQVQCHTYTGYCWCVTPDGKP                       g5305327

141  ISGTAVAHKTPRCPGSVNEKLPQREGTGKT                       2617724
146  ISGSSVQNKTPVCSGSVTDKPLSQGNSGRK                       6899373
145  ISGSSVQNKTPVCSGPVTDKPLSQGNSGRK                       g5305327
```

```
171  DDAA--APALETQPQGDEEDIASRYPTLWT      2617724
176  DDGSKPTPTMETQPVFDGDEITA--PTLWI      6899373
175  DDGSKPTPTMETQPVFDGDEITA--PTLWI      g5305327

199  EQVKSRQNKTNKNSVS----SCDQEHQS        2617724
204  KHLVIKDSKLNNTNI---RNSEKVYSCDQERQS   6899373
203  KHLVIKDSKLNNTNVRNSEKVHSCDQERQS      g5305327

223  ALEEAKQPKNDNVVIPECAHGGLYKPVQCH      2617724
234  ALEEAQQNPREGIVIPECAPGGLYKPVQCH      6899373
233  ALEEARQNPREGIVIPECAPGGLYKPVQCH      g5305327

253  PSTGYCWCVLVDTGRPIPGTSTRYEQPKCD      2617724
264  QSTGYCWCVLVDTGRPLPGTSTRYVMPSCE      6899373
263  QSTGYCWCVLVDTGRPLPGTSTRYVMPSCE      g5305327

283  NTARAHPAKARDLYKGRQLQGCPGAKKHEF      2617724
294  SDARAKTTEADDPFKDRELPGCPEGKKMEF      6899373
293  SDARAKSVEADDPFKDRELPGCPEGKKMEF      g5305327
```

Figure 3B

| | | | | |
|---|---|---|---|---|
| 313 | LTSVLDALSTDMVHA-ASDPSSSGRLSEP | 2617724 |
| 324 | ITSLLDALTTDMVQAINSAAPTGGGRFSEP | 6899373 |
| 323 | ITSLLDALTTDMVQAINSAAPTGGGRFSEP | g5305327 |
| | | |
| 342 | DPSHTLEERVVHWYFKLLDKNSSGDIGKKE | 2617724 |
| 354 | DPSHTLEERVVHWYFSQLDSNSSNNINKRE | 6899373 |
| 353 | DPSHTLEERVAHWYFSQLDSNSSDDINKRE | g5305327 |
| | | |
| 372 | IKPFKRFLRKKSKPKKCVKKFVEYCDVNND | 2617724 |
| 384 | MKPFKRYVKKKAKPKKCARRFTDYCDLNKD | 6899373 |
| 383 | MKPFKRYVKKKAKPKKCARRFTDYCDLNKD | g5305327 |
| | | |
| 402 | KSISVQELMGCLGVAKEDGKADTKKRHTPR | 2617724 |
| 414 | KVISLPELKGCLGVSKEG--------- | 6899373 |
| 413 | KVISLPELKGCLGVSKEGGSLGS----FPQ | g5305327 |
| | | |
| 432 | GHAESTSNRQPRKQG | 2617724 |
| 432 | ------------RLV | 6899373 |
| 439 | GKRAGTNPFIGR-LV | g5305327 |

Figure 3C

SEQUENCE LISTING

<160> NUMBER OF SEQ ID NOS: 41

<210> SEQ ID NO 1
<211> LENGTH: 446
<212> TYPE: PRT
<213> ORGANISM: Homo sapiens
<220> FEATURE:
<221> NAME/KEY: misc_feature
<223> OTHER INFORMATION: Incyte ID No: 2617724.orf1

<400> SEQUENCE: 1

```
Met Leu Leu Pro Gln Leu Cys Trp Leu Pro Leu Leu Ala Gly Leu
 1               5                  10                  15

Leu Pro Pro Val Pro Ala Gln Lys Phe Ser Ala Leu Thr Phe Leu
                20                  25                  30

Arg Val Asp Gln Asp Lys Asp Lys Asp Cys Ser Leu Asp Cys Ala
                35                  40                  45

Gly Ser Pro Gln Lys Pro Leu Cys Ala Ser Asp Gly Arg Thr Phe
                50                  55                  60

Leu Ser Arg Cys Glu Phe Gln Arg Ala Lys Cys Lys Asp Pro Gln
                65                  70                  75

Leu Glu Ile Ala Tyr Arg Gly Asn Cys Lys Asp Val Ser Arg Cys
                80                  85                  90

Val Ala Glu Arg Lys Tyr Thr Gln Glu Gln Ala Arg Lys Glu Phe
                95                  100                 105

Gln Gln Val Phe Ile Pro Glu Cys Asn Asp Asp Gly Thr Tyr Ser
                110                 115                 120

Gln Val Gln Cys His Ser Tyr Thr Gly Tyr Cys Trp Cys Val Thr
                125                 130                 135

Pro Asn Gly Arg Pro Ile Ser Gly Thr Ala Val Ala His Lys Thr
                140                 145                 150

Pro Arg Cys Pro Gly Ser Val Asn Glu Lys Leu Pro Gln Arg Glu
                155                 160                 165

Gly Thr Gly Lys Thr Asp Asp Ala Ala Ala Pro Ala Leu Glu Thr
                170                 175                 180

Gln Pro Gln Gly Asp Glu Glu Asp Ile Ala Ser Arg Tyr Pro Thr
                185                 190                 195

Leu Trp Thr Glu Gln Val Lys Ser Arg Gln Asn Lys Thr Asn Lys
                200                 205                 210

Asn Ser Val Ser Ser Cys Asp Gln Glu His Gln Ser Ala Leu Glu
                215                 220                 225

Glu Ala Lys Gln Pro Lys Asn Asp Asn Val Val Ile Pro Glu Cys
                230                 235                 240

Ala His Gly Gly Leu Tyr Lys Pro Val Gln Cys His Pro Ser Thr
                245                 250                 255

Gly Tyr Cys Trp Cys Val Leu Val Asp Thr Gly Arg Pro Ile Pro
                260                 265                 270

Gly Thr Ser Thr Arg Tyr Glu Gln Pro Lys Cys Asp Asn Thr Ala
                275                 280                 285

Arg Ala His Pro Ala Lys Ala Arg Asp Leu Tyr Lys Gly Arg Gln
                290                 295                 300

Leu Gln Gly Cys Pro Gly Ala Lys Lys His Glu Phe Leu Thr Ser
                305                 310                 315

Val Leu Asp Ala Leu Ser Thr Asp Met Val His Ala Ala Ser Asp
```

-continued

```
               320                 325                 330
Pro Ser Ser Ser Ser Gly Arg Leu Ser Glu Pro Asp Pro Ser His
               335                 340                 345

Thr Leu Glu Glu Arg Val Val His Trp Tyr Phe Lys Leu Leu Asp
               350                 355                 360

Lys Asn Ser Ser Gly Asp Ile Gly Lys Lys Glu Ile Lys Pro Phe
               365                 370                 375

Lys Arg Phe Leu Arg Lys Ser Lys Pro Lys Lys Cys Val Lys
               380                 385                 390

Lys Phe Val Glu Tyr Cys Asp Val Asn Asn Asp Lys Ser Ile Ser
               395                 400                 405

Val Gln Glu Leu Met Gly Cys Leu Gly Val Ala Lys Glu Asp Gly
               410                 415                 420

Lys Ala Asp Thr Lys Lys Arg His Thr Pro Arg Gly His Ala Glu
               425                 430                 435

Ser Thr Ser Asn Arg Gln Pro Arg Lys Gln Gly
               440                 445

<210> SEQ ID NO 2
<211> LENGTH: 434
<212> TYPE: PRT
<213> ORGANISM: Homo sapiens
<220> FEATURE:
<221> NAME/KEY: misc_feature
<223> OTHER INFORMATION: Incyte ID No: 6899373.orf2

<400> SEQUENCE: 2

Met Leu Pro Ala Arg Cys Ala Arg Leu Leu Thr Pro His Leu Leu
  1               5                  10                  15

Leu Val Leu Val Gln Leu Ser Pro Ala Arg Gly His Arg Thr Thr
                 20                  25                  30

Gly Pro Arg Phe Leu Ile Ser Asp Arg Asp Pro Gln Cys Asn Leu
                 35                  40                  45

His Cys Ser Arg Thr Gln Pro Lys Pro Ile Cys Ala Ser Asp Gly
                 50                  55                  60

Arg Ser Tyr Glu Ser Met Cys Glu Tyr Gln Arg Ala Lys Cys Arg
                 65                  70                  75

Asp Pro Thr Leu Gly Val Val His Arg Gly Arg Cys Lys Asp Ala
                 80                  85                  90

Gly Gln Ser Lys Cys Arg Leu Glu Arg Ala Gln Ala Leu Glu Gln
                 95                 100                 105

Ala Lys Lys Pro Gln Glu Ala Val Phe Val Pro Glu Cys Gly Glu
                110                 115                 120

Asp Gly Ser Phe Thr Gln Val Gln Cys His Thr Tyr Thr Gly Tyr
                125                 130                 135

Cys Trp Cys Val Thr Pro Asp Gly Lys Pro Ile Ser Gly Ser Ser
                140                 145                 150

Val Gln Asn Lys Thr Pro Val Cys Ser Gly Ser Val Thr Asp Lys
                155                 160                 165

Pro Leu Ser Gln Gly Asn Ser Gly Arg Lys Asp Asp Gly Ser Lys
                170                 175                 180

Pro Thr Pro Thr Met Glu Thr Gln Pro Val Phe Asp Gly Asp Glu
                185                 190                 195

Ile Thr Ala Pro Thr Leu Trp Ile Lys His Leu Val Ile Lys Asp
                200                 205                 210
```

```
Ser Lys Leu Asn Asn Thr Asn Ile Arg Asn Ser Glu Lys Val Tyr
            215                 220                 225

Ser Cys Asp Gln Glu Arg Gln Ser Ala Leu Glu Glu Ala Gln Gln
            230                 235                 240

Asn Pro Arg Glu Gly Ile Val Ile Pro Glu Cys Ala Pro Gly Gly
            245                 250                 255

Leu Tyr Lys Pro Val Gln Cys His Gln Ser Thr Gly Tyr Cys Trp
            260                 265                 270

Cys Val Leu Val Asp Thr Gly Arg Pro Leu Pro Gly Thr Ser Thr
            275                 280                 285

Arg Tyr Val Met Pro Ser Cys Glu Ser Asp Ala Arg Ala Lys Thr
            290                 295                 300

Thr Glu Ala Asp Asp Pro Phe Lys Asp Arg Glu Leu Pro Gly Cys
            305                 310                 315

Pro Glu Gly Lys Lys Met Glu Phe Ile Thr Ser Leu Leu Asp Ala
            320                 325                 330

Leu Thr Thr Asp Met Val Gln Ala Ile Asn Ser Ala Ala Pro Thr
            335                 340                 345

Gly Gly Gly Arg Phe Ser Glu Pro Asp Pro Ser His Thr Leu Glu
            350                 355                 360

Glu Arg Val Val His Trp Tyr Phe Ser Gln Leu Asp Ser Asn Ser
            365                 370                 375

Ser Asn Asn Ile Asn Lys Arg Glu Met Lys Pro Phe Lys Arg Tyr
            380                 385                 390

Val Lys Lys Lys Ala Lys Pro Lys Lys Cys Ala Arg Arg Phe Thr
            395                 400                 405

Asp Tyr Cys Asp Leu Asn Lys Asp Lys Val Ile Ser Leu Pro Glu
            410                 415                 420

Leu Lys Gly Cys Leu Gly Val Ser Lys Glu Gly Arg Leu Val
            425                 430

<210> SEQ ID NO 3
<211> LENGTH: 3134
<212> TYPE: DNA
<213> ORGANISM: Homo sapiens
<220> FEATURE:
<221> NAME/KEY: misc_feature
<223> OTHER INFORMATION: Incyte ID No: 2617724

<400> SEQUENCE: 3
cgagggcgga cgcaaagaac gcggaggacc tctgggtgcc tgcagggag ctgctccagc      60
cgggccgccg ggagcggtgg ggagagcatc gcgcagccgc ccctccacgc gcccgcccag    120
ccgcgctcgc ccactgggct ctcccggctg cagtgccagg gcgcaggacg cggccgatct    180
cccgctcccg ccacctccgc caccatgctg ctcccccagc tctgctggct gccgctgctc    240
gctgggctgc tcccgccggt gcccgctcag aagttctcgg cgctcacgtt tttgagagtg    300
gatcaagata aagacaagga ttgtagcttg gactgtgcgg gttcgcccca gaaacctctc    360
tgcgcatctg acggaaggac cttccttttcc cgttgtgaat tcaacgtgc caagtgcaaa    420
gatccccagc tagagattgc atatcgagga actgcaaag acgtgtccag gtgtgtggcc    480
gaaaggaagt atacccagga gcaagcccgg aaggagtttc agcaagtgtt cattcctgag    540
tgcaatgacg acggcaccta cagtcaggtc cagtgtcaca gctacacggg atactgctgg    600
tgcgtcacgc ccaacgggag gcccatcagc ggcactgccg tggcccacaa gacgccccgg    660
tgcccgggtt ccgtaaatga aaagttaccc caacgcgaag gcacaggaaa aacagatgat    720
```

-continued

```
gccgcagctc cagcgttgga gactcagcct caaggagatg aagaagatat tgcatcacgt      780
taccctaccc tttggactga acaggttaaa agtcggcaga acaaaaccaa taagaattca      840
gtgtcatcct gtgaccaaga gcaccagtct gccctggagg aagccaagca gcccaagaac      900
gacaatgtgg tgatccctga gtgtgcgcac ggcggcctct acaagccagt gcagtgccac      960
ccctccacgg ggtactgctg gtgcgtcctg gtggacacgg ggcgcccat tcccggcaca      1020 tccacaaggt acgagcagcc gaaatgtgac aacacggcca gggcccaccc agccaaagcc     1080
cgggacctgt acaagggccg ccagctacaa ggttgtccgg gtgccaaaaa gcatgagttt     1140
ctgaccagcg ttctggacgc gctgtccacg gacatggtcc acgccgcctc cgaccectcc     1200 tcctcgtcag gcaggctctc agaacccgac cccagccata ccctagagga gcgggtggtg     1260
cactggtact tcaaactact ggataaaaac tccagtggag acatcggcaa aaggaaatc      1320 aaaccettca agaggttcct tcgcaaaaaa tcaaagccca aaaaatgtgt gaagaagttt     1380
gttgaatact gtgacgtgaa taatgacaaa tccatctccg tacaagaact gatgggctgc     1440
ctgggcgtgg cgaaagagga cggcaaagcg gacaccaaga aacgccacac ccccagaggt     1500
catgctgaaa gtacgtctaa tagacagcca aggaaacaag gataaatggc tcatacccg     1560 aaggcagttc ctagacacat gggaaatttc cctcaccaaa gagcaattaa gaaaacaaaa     1620
acagaaacac atagtatttg cactttgtac tttaaatgta aattcacttt gtagaaatga     1680
gctatttaaa cagactgttt taatctgtga aaatggagag ctggcttcag aaaattaatc     1740
acatacaatg tatgtgtcct cttttgacct tggaaatctg tatgtggtgg agaagtattt     1800
gaatgcattt aggcttaatt tcttcgcctt ccacatgtta acagtagagc tctatgcact     1860
ccggctgcaa tcgtatggct ttctctaacc cctgcagtca cttccagatg cctgtgctta     1920
cagcattgtg gaatcatgtt ggaagctcca catgtccatg gaagtttgtg atgtacggcc     1980
gaccctacag gcagttaaca tgcatgggct ggtttgtttc ttgggatttt ctgttagttt     2040
gtcttgtttt gctttccaga gatcttgctc atacaatgaa tcacgcaacc actaaagcta     2100
tccagttaag tgcaggtagt tcccctggag gaaataatat tttcaaactg tcgttggtgt     2160
gatactttgg ctcaaaggat cttttgctttt ccattttaag cttctgtttt gagttttgcc     2220
ctggggcttg aatgagtccc agagagtcgt tcggatggtg ggaggctgcc taggaggcag     2280
taaatccagt cacagtgcct gggaggggcc catccttcca aaatgtaaat ccagtcgcgg     2340
tgtgaccgag ctggctaaca ggcttgtctg cctggttttc tcctacacg tggacattat     2400 tctcctgatc ctcctacctg gtccacccca gggctaccgg aagtaaaat cttcacctga     2460 accaattatg agcagtctcc ttactgaagg tacagccgga tacgtggtgc ccccgggct     2520 ggtgttggca gccgggggga ggtgcctgag ggtccccacg gttcctttct gcttttctga     2580
atgcatcaag ggtacgagaa cttgccaatg ggaaattcat ccgagtggca ctggcagaga     2640
aggataggag tggaatgccc acacagtgac caacagaact ggtctgcgtg cataaccagc     2700 tgccacccctc aggcctgggc cccagagctc agggcaccca gtgtcttaag gaaccatttg     2760
gaggacagtc tgagagcagg aacttcaagc tgtgattcta tctcggctca gacttttggt     2820
tggaaaaaga tcttcatggc cccaaatccc ctgagacatg ccttgtagaa tgattttgtg     2880
atgttgtgat gcttgtggag catcgcgtaa ggcttcttgc ttatttaaac tgtgcaaggt     2940
aaaaatcaag cctttggagc cacagaacca gctcaagtac atgccaatgt tgtttaagaa     3000
acagttatga tcctaaactt tttggataat cttttatatt tctgaccttt gaatttaatc     3060
```

-continued

| attgttctta gattaaaata aaatatgcta ttgaaactaa aaaaaaaaaa gaggggagaa | 3120 |
| gaaaaaaaaa aagg | 3134 |

<210> SEQ ID NO 4
<211> LENGTH: 221
<212> TYPE: DNA
<213> ORGANISM: Homo sapiens
<220> FEATURE:
<221> NAME/KEY: misc_feature
<223> OTHER INFORMATION: Incyte ID No: 1388229H1
<221> NAME/KEY: unsure
<222> LOCATION: 44
<223> OTHER INFORMATION: a, t, c, g, or other

<400> SEQUENCE: 4

| cgagggcgga cgcaaagaac gcggaggacc tctgggtgcc tgcngggag ctgctccagc | 60 |
| cgggccgccg ggagcggtgg ggagagcatc gcggaccgcc cctccacgcg cccgcccagc | 120 |
| cgcgttcgcc cactgggctc tcccggctgc agtgccaggg cgcaggacgc ggccgatctc | 180 |
| ccgctcccgc cacctccgcc accatgctgc tcccccagct c | 221 |

<210> SEQ ID NO 5
<211> LENGTH: 507
<212> TYPE: DNA
<213> ORGANISM: Homo sapiens
<220> FEATURE:
<221> NAME/KEY: misc_feature
<223> OTHER INFORMATION: Incyte ID No: 2617724F6
<221> NAME/KEY: unsure
<222> LOCATION: 479, 482
<223> OTHER INFORMATION: a, t, c, g, or other

<400> SEQUENCE: 5

| gcccactggg ctctcccggc tgcagtgcca gggcgcagga cgcggccgat ctcccgctcc | 60 |
| cgccacctcc gccaccatgc tgctccccca gctctgctgg ctgccgctgc tcgctgggct | 120 |
| gctcccgccg gtgcccgctc agaagttctc ggcgctcacg ttttttgagag tggatcaaga | 180 |
| taaagacaag gattgtagct tggactgtgc gggttcgccc cagaaacctc tctgcgcatc | 240 |
| tgacggaagg accttccttt cccgttgtga atttcaacgt gccaagtgca agatcccca | 300 |
| gctagagatt gcatatcgag gaaactgcaa agacgtgtcc aggtgtgtgg gccgaaagga | 360 |
| agtatacccca ggagcaagcc cggaagagtt tcagcaaagt gttcatttcc tgagtgcaat | 420 |
| gaacgacggg caccttacag ttcaaggtcc aatgttcaca agctaacacg gggattacng | 480 |
| cntggtgcgt tcacggccca acgggaa | 507 |

<210> SEQ ID NO 6
<211> LENGTH: 456
<212> TYPE: DNA
<213> ORGANISM: Homo sapiens
<220> FEATURE:
<221> NAME/KEY: misc_feature
<223> OTHER INFORMATION: Incyte ID No: 2081850F6

<400> SEQUENCE: 6

| gctggtgcgt cacgcccaac gggaggccca tcagcggcac tgccgtggcc cacaagacgc | 60 |
| cccggtgccc gggttccgta aatgaaaagt taccccaacg cgaaggcaca ggaaaaacag | 120 |
| atgatgccgc agctccagcg ttggagactc agcctcaagg agatgaagaa gatattgcat | 180 |
| cacgttaccc tacccttttgg actgaacagg ttaaagtcg gcagaacaaa accaataaga | 240 |
| attcagtgtc atcctgtgac caagagcacc agtctgccct ggaggaagcc aagcagccca | 300 |

```
agaacgacaa tgtggtgatc cctgagtgtg cgcacggcgg cctctacaag ccagtgcagt    360
gccacccctc cacggggtac tgctggtgcg tcctggtgga cacggggcgc cccattcccg    420
ggggcacatc cacaaggtac gagcagccga aatgtg                             456
```

<210> SEQ ID NO 7  
<211> LENGTH: 341  
<212> TYPE: DNA  
<213> ORGANISM: Homo sapiens  
<220> FEATURE:  
<221> NAME/KEY: misc_feature  
<223> OTHER INFORMATION: Incyte ID No: 2313837H1  
<221> NAME/KEY: unsure  
<222> LOCATION: 10, 21, 33, 58, 126, 145, 147, 152, 157, 173, 186, 268  
<223> OTHER INFORMATION: a, t, c, g, or other

<400> SEQUENCE: 7

```
atgtgacaan acggccaggg ntcacccagt canagcccgg gacctgtaca agggccgnca    60
gctacaaggt tgtccgggtg ccaaaaagca tgagtttctg accagcgttc tggacgcgct   120
gtccanggac atggtccacg ccgcntncga cncctcntcc tcgtcaggca ggntctcaga   180
acccgncccc agccataccc tagaggagcg ggtggtgcac tggtacttca aactactgga   240
taaaaactcc agtggagaca tcggcaanaa ggaaatcaaa cccttcaaga ggttcttcgc   300
aaaaaatcaa agcccaaaaa atgtgtgaag aagtttgttg a                       341
```

<210> SEQ ID NO 8  
<211> LENGTH: 498  
<212> TYPE: DNA  
<213> ORGANISM: Homo sapiens  
<220> FEATURE:  
<221> NAME/KEY: misc_feature  
<223> OTHER INFORMATION: Incyte ID No: 1804413F6  
<221> NAME/KEY: unsure  
<222> LOCATION: 46, 226, 294, 349  
<223> OTHER INFORMATION: a, t, c, g, or other

<400> SEQUENCE: 8

```
aatcaaaccc ttcaagaggt tccttcgcaa aaatcaaag cccaanaaat gtgtgaagaa     60
gtttgttgaa tactgtgacg tgaataatga caaatccatc tccgtacaag aactgatggg   120
ctgcctgggc gtggcgaaag aggacggcaa agcggacacc aagaaacgcc acaccccag    180 aggtcatgct gaaagtacgt ctaatagaca gccaaggaaa caaggntaaa tggctcatac   240
cccgaaggca gttcctagac acatggggaa ttttccctca ccaaagagcg attnaggaaa   300
ccaaaaccgg aaaccaccat agtatttgca cttttgtact ttaaatgtna attcacttt    360 gtagaaatga gctatttaaa cagactgttt taatctgtgg aaaatggaga gctggcttca   420
gaaaattaat cacataccaa tgtatgtgtc ctcttttgac cttggaaatc tgtatgtggt   480
ggagagtatt tgaatgca                                                 498
```

<210> SEQ ID NO 9  
<211> LENGTH: 209  
<212> TYPE: DNA  
<213> ORGANISM: Homo sapiens  
<220> FEATURE:  
<221> NAME/KEY: misc_feature  
<223> OTHER INFORMATION: Incyte ID No: 3207379H1

<400> SEQUENCE: 9

```
atgagctatt taaacagact gttttaatct gtgaaaatgg agagctggct tcagaaaatt    60
aatcacatac aatgtatgtg tcctcttttg accttggaaa tctgtatgtg gtggagaagt   120
```

```
atttgaatgc atttaggctt aatttcttcg ccttccacat gttaacagta gagctctatg      180
cactccggct gcaatcgtat ggctttctc                                        209

<210> SEQ ID NO 10
<211> LENGTH: 515
<212> TYPE: DNA
<213> ORGANISM: Homo sapiens
<220> FEATURE:
<221> NAME/KEY: misc_feature
<223> OTHER INFORMATION: Incyte ID No: 2347051F6
<221> NAME/KEY: unsure
<222> LOCATION: 464
<223> OTHER INFORMATION: a, t, c, g, or other

<400> SEQUENCE: 10
catgttaaca gtagagctct atgcactccg gctgcaatcg tatggctttc tctaacccct       60
gcagtcactt ccagatgcct gtgcttacag cattgtggaa tcatgttgga agctccacat      120
gtccatggaa gtttgtgatg tacggccgac cctacaggca gttaacatgc atgggctggt      180
ttgtttcttg ggattttctg ttagtttgtc ttgttttgct ttccagagat cttgctcata      240
caatgaatca cgcaaccact aaagctatcc agttaagtgc aggtagttcc cctggaggaa      300
ataatatttt caaactgtcg ttggtgtgat actttggctc aaaggatctt tgcttttcca      360
ttttaagctt ctgttttgag ttttgccctg gggcttgaat gagtcccaga gagtcgttcg      420
gatggtggga ggctgcctag gaggcagtaa atccagtcac agtncctggg aggggccat      480 ccttccaaaa atgtaaaatc cagtctcggt gtgac                                 515

<210> SEQ ID NO 11
<211> LENGTH: 556
<212> TYPE: DNA
<213> ORGANISM: Homo sapiens
<220> FEATURE:
<221> NAME/KEY: misc_feature
<223> OTHER INFORMATION: Incyte ID No: 1259341F1
<221> NAME/KEY: unsure
<222> LOCATION: 66, 489
<223> OTHER INFORMATION: a, t, c, g, or other

<400> SEQUENCE: 11
ggctgcctag gaggcagtaa atccagtcac agtgcctggg aggggcccat ccttccaaaa       60
tgtaantcca gtcgcggtgt gaccgagctg gctaacaggc ttgtctgcct ggttttcctc      120
ctacacgtgg acattattct cctgatcctc ctacctggtc cacccaggg ctaccggaag      180 gtaaaatctt cacctgaacc aattatgagc agtctcctta ctgaaggtac agccggatac      240
gtggtgcccc cggggctggt gttggcagcc ggggggaggt gcctgagggt ccccacggtt      300
cctttctgct tttctgaatg catcaagggt acgagaactt gccaatggga aattcatccg      360
agtggcactg gcagagaagg ataggagtgg aatgcccaca cagtgaccaa cagaactggt      420
ctgcgtgcat aaccagctgc caccctcagg cctgggcccc agagctcagg gcacccagtg      480
tcttaaggna ccatttggag gacagtctga gagcaggaac tttcaagctg tgattctatc      540
tcggctcaga ctttttt                                                     556

<210> SEQ ID NO 12
<211> LENGTH: 556
<212> TYPE: DNA
<213> ORGANISM: Homo sapiens
<220> FEATURE:
<221> NAME/KEY: misc_feature
<223> OTHER INFORMATION: Incyte ID No: 1804413T6
<221> NAME/KEY: unsure
```

<222> LOCATION: 461, 501, 540, 542
<223> OTHER INFORMATION: a, t, c, g, or other

<400> SEQUENCE: 12

```
tcaaaggtca gaaatataaa agattatcca aaaagtttag gatcataact gtttcttaaa      60
caacattggc atgtacttga gctggttctg tggctccaaa ggcttgattt ttaccttgca     120
cagtttaaat aagcaagaag ccttacgcga tgctccacaa gcatcacaac atcacaaaat    180
cattctacaa ggcatgtctc aggggatttg gggccatgaa gatcttttc caaccaaaag     240
tctgagccga gatagaatca cagcttgaag ttcctgctct cagactgtcc tccaaatggt    300
tccttaagac actgggtgcc ctgagctctg ggcccaggc ctgagggtgg cagctggtta     360
tgcacgcaga ccagttctgt tggtcactgt gtgggcattc cactcctaac cttctctgcc    420
agtgccactc ggatgaattt cccattggca agttctcgta nccttgatgc attcagaaaa    480
gcagaaagga accgtgggga ncctcaggca cttccccgg tgccacaaca gcccggggn      540
ancacgtatc ggtgta                                                     556
```

<210> SEQ ID NO 13
<211> LENGTH: 578
<212> TYPE: DNA
<213> ORGANISM: Homo sapiens
<220> FEATURE:
<221> NAME/KEY: misc_feature
<223> OTHER INFORMATION: Incyte ID No: 081943R1
<221> NAME/KEY: unsure
<222> LOCATION: 233, 331, 339, 411, 440, 443, 454, 467, 484, 486, 538, 545, 549-563, 572
<223> OTHER INFORMATION: a, t, c, g, or other

<400> SEQUENCE: 13

```
ttctgaatgc atcaagggta cgagaacttg ccaatgggaa attcatccga gtggcactgg      60
cagagaagga taggagtgga atgcccacac agtgaccaac agaactggtc tgcgtgcata    120
accagctgcc accctcaggc ctgggcccca gagctcaggg cacccagtgt cttaaggaac    180
catttggagg acagtctgag agcaggaact tcaagctgtg attctatctc ggntcagact    240
tttggttgga aaaagatctt catggcccca atcccctga gacatgcctt gtagatgatt     300
ttgtgatgtt gtgatgcttg tggagcatcg ngtaaaggnt tcttgcttat ttaaactgtg    360
caaggtaaaa atcaagcctt tggagccaca gaaccagctt caagtacatg nccaatgttg    420
tttaaggaac agttatggtn ccnaaaactt tttnggtaaa cctttanaat ttctgaccct    480
ttgnanttta atccattggt ccttagggtt taaaatttaa aatattgctt aatttggnaa    540
ccttnaaann nnnnnnnnn nnnaaaaaaa ancctcgg                              578
```

<210> SEQ ID NO 14
<211> LENGTH: 77
<212> TYPE: DNA
<213> ORGANISM: Canis familiaris
<220> FEATURE:
<221> NAME/KEY: misc_feature
<223> OTHER INFORMATION: Incyte ID No: 702245306H1

<400> SEQUENCE: 14

```
ccagccacac cctcgaggag agggtggtcc actggtactt caagctactc gataagaact      60
ccaggcgggg acacttg                                                    77
```

<210> SEQ ID NO 15
<211> LENGTH: 538
<212> TYPE: DNA

```
<213> ORGANISM: Rattus norvegicus
<220> FEATURE:
<221> NAME/KEY: misc_feature
<223> OTHER INFORMATION: Incyte ID No: 702570096T2

<400> SEQUENCE: 15 tcctatttc ctgtgctgtc tattcgaaga agttacttcg gcatttcctc tgtgtggtgt      60
gactgcttcc ttggttgttt ggtcttaccc tcctctctgg tgacgcccat tcagcccatg    120
atctcctgca ccgtgtatgg acttatctgt tgttcatatc gcagtattca atcaaatctt    180
cttcacgcac tttttgggct tggatttctt tcgcaggaac ctcttaaagg gttggatttc    240
cttcttgcca atgtctccgc tagagttctt atcaagcagc ttgaagtacc aattgcacaa    300
ccctctcctc cagggttgtg gctggggtct ggctctgaca gcctgccaga tgaggaagag    360
gggtcagaga cggcgtggac catgtcagtg gagagcgcat ccaggacact tgtcagaaac    420
tcgtgctttt tggcaccagg acaaccctgc agtggcctgt tcttgtacag gtcccgggcc    480
ttcgctgggt gagctcgggc tgtgtcatca cattagggct gctcatacct tgtggagg     538

<210> SEQ ID NO 16
<211> LENGTH: 208
<212> TYPE: DNA
<213> ORGANISM: Rattus norvegicus
<220> FEATURE:
<221> NAME/KEY: misc_feature
<223> OTHER INFORMATION: Incyte ID No: 701234138H1

<400> SEQUENCE: 16
ggatgcgctc tccactgaca tggtccacgc cgtctctgac ccctcttcct catctggcag     60
gctgtcagag ccagacccca gccacaccct ggaggagagg gttgtgcatt gggacttcaa    120
gctgcttgat aagaactcta gcggagacat tggcaagaag gaaatcaaac cctttaagag    180
gttcctgcga aagaaatcca agcccaaa                                       208

<210> SEQ ID NO 17
<211> LENGTH: 216
<212> TYPE: DNA
<213> ORGANISM: Rattus norvegicus
<220> FEATURE:
<221> NAME/KEY: misc_feature
<223> OTHER INFORMATION: Incyte ID No: 700888003H1

<400> SEQUENCE: 17
tggaccgagc aagttgaaga gtccggcaga gacaaggacc agataagaaa tatgagcatc      60
cctcctgtga tcaagagcac cagtcggctc ttgaggaagc caagcaaccc aagaatgaca    120
atgtagtgat ccctgagtgt acacacggcg gcctctacaa gccagtgcaa tgccacccat    180
ccactggata ctgctggtgt gtgctggtag acactg                              216

<210> SEQ ID NO 18
<211> LENGTH: 308
<212> TYPE: DNA
<213> ORGANISM: Rattus norvegicus
<220> FEATURE:
<221> NAME/KEY: misc_feature
<223> OTHER INFORMATION: Incyte ID No: 700268254H1

<400> SEQUENCE: 18
cggtctccac cagatgcggt aggaccgcag agcagttctt gacccctcgc tctcgcgttc     60
gcacaccgga tcttcgccga gtgcctgggt gcagcgtgtg gggcgtctgc ctcgcttggt    120
ccctccagc gtcaccatgc tgccgccaca gctgtgctgg ctgccgctgc tcgctgcgtt    180
```

```
gctgccgcca gtgcccgcgc agaagttctc ggcgctcacg ttcttgagag tcgatcaaga      240
caaagacaga gactgcagcc tggactgccc cagctcccct cagaagccgc tctgcgcctc      300
agatggga                                                               308
```

<210> SEQ ID NO 19
<211> LENGTH: 294
<212> TYPE: DNA
<213> ORGANISM: Rattus norvegicus
<220> FEATURE:
<221> NAME/KEY: misc_feature
<223> OTHER INFORMATION: Incyte ID No: 700271122H1

<400> SEQUENCE: 19

```
agataccctc accacagaca tggttcaggc cattaactca gcagcgccca ctgaaggtgg       60
gaggttctca gagccagacc ccagccacac cctggaggag cgggtggcac actggtactt      120
cagccagctg gatagcaaca gcagtgatga cattaacaag cgggagatga aaccgttcaa      180
gcgctatgtg aagaagaaag ccaagcccaa gaagtgcgcc cggcgcttca ccgactactg      240
tgacctgaac aaggataagg ccatctcgct gcctgagctg aagggctgcc tggg            294
```

<210> SEQ ID NO 20
<211> LENGTH: 3574
<212> TYPE: DNA
<213> ORGANISM: Homo sapiens
<220> FEATURE:
<221> NAME/KEY: misc_feature
<223> OTHER INFORMATION: Incyte ID No: 6899373

<400> SEQUENCE: 20

```
tccctgaccg cgagctctgc gagccccgc cgcaggacca cggcccgctc cccgcctgcg        60
cgagggcccc gagcgaagga aggaagggag gcgcgctgtg cgcccgcgg agcccgcgaa       120 ccccgctcgc tgccggctgc ccagcctggc tggcaccatg ctgcccgcgc gctgcgcccg      180
cctgctcacg ccccacttgc tgctggtgtt ggtgcagctg tccctgctc gcggccaccg      240 caccacaggc cccaggtttc taataagtga ccgtgaccca cagtgcaacc tccactgctc      300
caggactcaa cccaaaccca tctgtgcctc tgatggcagg tcctacgagt ccatgtgtga      360
gtaccagcga gccaagtgcc gagacccgac cctgggcgtg gtgcatcgag gtagatgcaa      420
agatgctggc cagagcaagt gtcgcctgga gcgggctcaa gccctggagc aagccaagaa      480
gcctcaggaa gctgtgtttg tcccagagtg tggcgaggat ggctcctta cccaggtgca      540 gtgccatact tacactgggt actgctggtg tgtcaccccg gatgggaagc ccatcagtgg      600
ctcttctgtg cagaataaaa ctcctgtatg ttcaggttca gtcaccgaca gcccttgag      660 ccagggtaac tcaggaagga agatgacgg gtctaagccg acacccacga tggagaccca      720
gccggtgttc gatggagatg aaatcacagc cccaactcta tggattaaac acttggtgat      780
caaggactcc aaactgaaca acaccaacat aagaaattca gagaaagtct attcgtgtga      840
ccaggagagg cagagtgccc tggaagaggc cagcagaat ccccgtgagg gtattgtcat      900
ccctgaatgt gcccctgggg gactctataa gccagtgcaa tgccaccagt ccactggcta      960
ctgctggtgt gtgctggtgg acacaggcg cccgctgcct gggacctcca cacgctacgt     1020
gatgcccagt tgtgagagcg acgccagggc caagactaca gaggcggatg acccttcaa     1080 ggacagggag ctaccaggct gtccagaagg gaagaaatg gagttatca ccagcctact     1140 ggatgctctc accactgaca tggttcaggc cattaactca gcagcgccca ctggaggtgg     1200
```

```
gaggttctca gagccagacc ccagccacac cctggaggag cgggtagtgc actggtattt    1260
cagccagctg gacagcaata gcagcaacaa cattaacaag cgggagatga agcccttcaa    1320
gcgctacgtg aagaagaaag ccaagcccaa gaaatgtgcc cggcgtttca ccgactactg    1380
tgacctgaac aaagacaagg tcatttcact gcctgagctg aagggctgcc tgggtgttag    1440
caaagaagga cgcctcgtct aaggagcaga aacccaagg gcaggtggag agtccaggga    1500
ggcaggatgg atcaccagac acctaacctt cagcgttgcc catggccctg ccacatcccg    1560
tgtaacataa gtggtgccca ccatgtttgc acttttaata actcttactt gcgtgttttg    1620
tttttggttt cattttaaaa caccaatatc taataccaca gtgggaaaag gaaagggaag    1680
aaagacttta ttctctctct tattgtaagt ttttggatct gctactgaca acttttagag    1740
ggttttgggg gggtggggga gggtgttgtt ggggctgaga agaaagagat ttatatgctg    1800
tatataaata tatatgtaaa ttgtatagtt cttttgtaca ggcattggca ttgctgtttg    1860
tttatttctc tccctctgcc tgctgtgggt ggtgggcact ctggacacat agtccagctt    1920
tctaaaatcc aggactctat cctgggccta ctaaacttct gtttggagac tgacccttgt    1980
gtataaagac gggagtcctg caattgtact gcggactcca cgagttcttt tctggtggga    2040
ggactatatt gccccatgcc attagttgtc aaaattgata agtcacttgg ctctcggcct    2100
tgtccaggga ggttgggcta aggagagatg gaaactgccc tgggagagga agggagtcca    2160
gatcccatga atagcccaca caggtaccgg ctctcagagg gtccgtgcat tcctgctctc    2220
cggaccccca aagggcccag cattggtggg tgcaccagta tcttagtgac cctcggagca    2280
aattatccac aaaggatttg cattacgtca ctcgaaacgt tttcatccat gcttagcatc    2340
tactctgtat aacgcatgag aggggaggca aagaagaaaa agacacacag aagggccttt    2400
aaaaagtag atatttaata tctaagcagg ggaggggaca ggacagaaag cctgcactga    2460
ggggtgcggt gccaacaggg aaactcttca cctcctgca aacctaccag tgaggctccc    2520
agagacgcag ctgtctcagt gccaggggca gattgggtgt gacctctcca ctcctccatc    2580
tcctgctgtt gtcctagtgg ctatcacagg cctgggtggg tgggttgggg gaggtgtcag    2640
tcaccttgtt ggtaacacta agttgtttt gttggtttt taaaaaccca atactgaggt    2700
tcttcctgtt ccctcaagtt ttcttatggg cttccaggct ttaagctaat tccagaagta    2760
aaactgatct tgggtttcct attctgcctc ccctagaagg gcagggtga taacccagct    2820
acagggaaat cccggcccaa ctttccacag gcatcacagg catcttccgc ggattctagg    2880
gtgggctgcc cagccttctg gtctgaggcg cagctccctc tgcccaggtg ctgtgcctat    2940
tcaagtggcc ttcaggcaga gcagcaagtg gcccttagcg ccccttccca taagcagctg    3000
tggtggcagt gagggaggtt gggtagccct ggactggtcc cctcctcaga tcacccttgc    3060
aaatctggcc tcatcttgta ttccaacccg acatccctaa aagtacctcc acccgttccg    3120
ggtctggaag gcgttggcac cacaagcact gtccctgtgg gaggagcaca accttctcgg    3180
gacaggatct gatgggtct tgggctaaag gaggtccctg ctgtcctgga gaaagtccta    3240
gaggttatct caggaatgac tggtggccct gccccaacgt ggaaaggtgg gaaggaagcc    3300
ttctcccatt agccccaatg agagaactca acgtgccgga gctgagtggg ccttgcacga    3360
gacactggcc ccactttcag gcctggagga agcatgcaca catggagacg gcgcctgcct    3420
gtagatgttt ggatcttcga gatctcccca ggcatcttgt ctcccacagg atcgtgtgtg    3480
taggtggtgt tgtgtggttt cctttgtga aggagagagg gaaactattt gtagcttgtt    3540
ttataaaaaa taaaaaatgg gtaaatcttg aaaa                                3574
```

<210> SEQ ID NO 21
<211> LENGTH: 538
<212> TYPE: DNA
<213> ORGANISM: Homo sapiens
<220> FEATURE:
<221> NAME/KEY: misc_feature
<223> OTHER INFORMATION: Incyte ID No: 6899373H1
<221> NAME/KEY: unsure
<222> LOCATION: 52-75, 121
<223> OTHER INFORMATION: a, t, c, g, or other

<400> SEQUENCE: 21

| | | | | | |
|---|---|---|---|---|---|
| atggccttaa | tcatgtcgac | ggcggcgcag | tgtctgaagg | ctgcgctgtg | cnnnnnnnnn | 60 |
| nnnnnnnnnn | nnnnagaca | cgctcgcgct | cagctcccct | ctgcgcggtt | catgactgtg | 120 |
| ntccctgacc | gcgagctctg | cgagccccg | ccgcaggacc | acggcccgct | ccccgcctgc | 180 |
| gcgagggccc | cgagcgaagg | aaggaaggga | ggcgcgctgt | gcgccccgcg | gagcccgcga | 240 |
| accccgctcg | ctgccggctg | cccagcctgg | ctggcaccat | gctgcccgcg | cgctgcgccc | 300 |
| gcctgctcac | gccccacttg | ctgctggtgt | tggtgcagct | gtcccctgct | cgcggccacc | 360 |
| gcaccacagg | ccccaggttt | ctaataagtg | agcgtgaccc | acagtgcaac | ctccactgct | 420 |
| ccaggactca | acccaaaccc | atctgtgcct | ctgatggcag | gtcctacgag | tccatgtgtg | 480 |
| agtaccagcg | agccaagtgc | cgagacccga | ccctgggcgt | ggtgcatcga | ggtagatg | 538 |

<210> SEQ ID NO 22
<211> LENGTH: 462
<212> TYPE: DNA
<213> ORGANISM: Homo sapiens
<220> FEATURE:
<221> NAME/KEY: misc_feature
<223> OTHER INFORMATION: Incyte ID No: 6898356H1

<400> SEQUENCE: 22

| | | | | | |
|---|---|---|---|---|---|
| ctccactgct | ccaggactca | acccaaaccc | atctgtgcct | ctgatggcag | gtcctacgag | 60 |
| tccatgtgtg | agtaccagcg | agccaagtgc | cgagacccga | ccctgtggcg | tggtgcatcg | 120 |
| aggtagatgc | aaagatgctg | gccagagcaa | gtgtcgcctg | gagcgggctc | aagccctgga | 180 |
| gcaagccaag | aagcctcagg | aagctgtgtt | tgtcccagag | tgtggcgagg | atggctcctt | 240 |
| tacccaggtg | cagtgccata | cttacactgg | gtactgctgg | tgtgtcaccc | cggatgggaa | 300 |
| gcccactcag | ttggctcttc | tgtgcagaat | aaaactcctg | tatgttcagg | ttcagtcacc | 360 |
| gacaagccct | tgagccaggg | taactcagga | aggaaagatg | acgggtctaa | gccgataccc | 420 |
| acgatggaga | cccagccggt | gttcgatgga | gatgaaatca | ca | | 462 |

<210> SEQ ID NO 23
<211> LENGTH: 459
<212> TYPE: DNA
<213> ORGANISM: Homo sapiens
<220> FEATURE:
<221> NAME/KEY: misc_feature
<223> OTHER INFORMATION: Incyte ID No: 6977387H1
<221> NAME/KEY: unsure
<222> LOCATION: 81, 91, 225
<223> OTHER INFORMATION: a, t, c, g, or other

<400> SEQUENCE: 23

| | | | | | |
|---|---|---|---|---|---|
| aggctggtga | taaactccat | tttcttccct | tctggacagc | ctggtagctc | cctgtccttg | 60 |
| acaggggtca | tccgcctctg | ntagtcttgg | ncctggcgtc | gctctcacaa | ctgggcatca | 120 |
| cgtagcgtgt | ggaggtccca | ggcagcgggc | gccctgtgtc | caccagcaca | caccagcagt | 180 |

```
agccagtgga ctggtggcat tgcactggct tatagagtcc cccangggca cattcaggga      240
tgacaatacc ctcacgggga ttctgctggg cctcttccag agcactctgc ctctcctggt      300
cacacgaata gactttctct gaatttctta tgttggtgtt gttcagtttg gagtccttga      360
tcaccaagtg tttaatccat agagttgggg ctgtgatttc atctccatcg aacaccggct      420
gggtctccat cgtgggtgtc ggcttagacc cgtcatctt                             459

<210> SEQ ID NO 24
<211> LENGTH: 603
<212> TYPE: DNA
<213> ORGANISM: Homo sapiens
<220> FEATURE:
<221> NAME/KEY: misc_feature
<223> OTHER INFORMATION: Incyte ID No: 6835981H1

<400> SEQUENCE: 24
gtccactggc tactgctggt gtgtgctggt ggacacaggg cgcccgctgc ctgggacctc       60
cacacgctac gtgatgccca gttgtgagag cgacgccagg gccaagacta cagaggcgga      120 tgacccctc aaggacaggg agctaccagg ctgtccagaa gggaagaaaa tggagtttat      180
caccagccta ctggatgctc tcaccactga catggttcag gccattaact cagcagcgcc      240
cactggaggt gggaggttct cagagccaga ccccagccac accctggagg agcgggtagt      300
gcactggtat ttcagccagc tggacagcaa tagcagcaac aacattaaca agcgggagat      360
gaagcccttc aagcgctacg tgaagaagaa agccaagccc aagaaatgtg cccggcgttt      420
caccgactac tgtgacctga acaaagacaa ggtcatttca ctgcctgagc tgaagggctg      480
cctgggtgtt agcaaagaag gacgcctcgt ctaaggagca gaaaacccaa gggcaggtgg      540
agagtccagg caggcaggat ggatcaccag acacctaacc ttcagcgttg ccatggccct      600
gcc                                                                   603

<210> SEQ ID NO 25
<211> LENGTH: 492
<212> TYPE: DNA
<213> ORGANISM: Homo sapiens
<220> FEATURE:
<221> NAME/KEY: misc_feature
<223> OTHER INFORMATION: Incyte ID No: 3316785T6

<400> SEQUENCE: 25
atatttattt acagcatata aatctctttc ttctcaaccc caacaacacc ctccccacc       60 cccccaaaac cctctaaaag ttgtcagtag cagatccaaa aacttacaat aagagagaga      120
ataaagtctt tcttcccttt ccttttccca ctgtggtatt agatattggt gttttaaaat      180
gaaaccaaaa acaaaacacg caagtaagag ttattaaaag tgcaaacatg gtgggcacca      240
cttatgttac acgggatgtg gcagggccat gggcaacgct gaaggttagg tgtctggtga      300
tccatcctgc ctccctggac tctccacctg cccttgggtt ttctgctcct tagacgaggc      360
gtccttcttt gctaacaccc aggcagccct tcagctcagg cagtgaaatg accttgtctt      420
tgttcaggtc acagtagtcg gtgaaacgcc gggcacattt cttgggcttg ctttcttct      480 tcacgtagcg ct                                                         492

<210> SEQ ID NO 26
<211> LENGTH: 580
<212> TYPE: DNA
<213> ORGANISM: Homo sapiens
<220> FEATURE:
```

```
<221> NAME/KEY: misc_feature
<223> OTHER INFORMATION: Incyte ID No: 746080R1
<221> NAME/KEY: unsure
<222> LOCATION: 74, 78-79, 448
<223> OTHER INFORMATION: a, t, c, g, or other

<400> SEQUENCE: 26
gagatttata tgctgatata taaatatata tgtaaattgt atagttcttt tgtacaggca      60
ttggcattgc tgtntgtnna tttctctccc tctgcctgct gtgggtggtg ggcactctgg     120
acacatagtc cagctttcta aaatccagga ctctatcctg gcctactaa  acttctgttt    180
ggagactgac ccttgtgtat aaagacggga gtcctgcaat tgtactgcgg actccacgag    240
ttcttttctg gtgggaggac tatattgccc catgccatta gttgtcaaaa ttgataagtc    300
acttggctct cggccttgtc cagggaggtt gggctaagga gagtggaaac tgccctggga    360
gaggaaggga gtccagatcc catgaatagc ccacacaggt accggctctc agagggtccg    420
tgcattcctg ctctccggac ccccaaangg cccagcattg gtggtgcacc agtatcttag    480
tgaccctcgg agcaaattat ccacaaagga tttgcattac gtcactcgaa acgttttcat    540
ccatgcttag catctactct gtataacgca tgagagggag                          580

<210> SEQ ID NO 27
<211> LENGTH: 501
<212> TYPE: DNA
<213> ORGANISM: Homo sapiens
<220> FEATURE:
<221> NAME/KEY: misc_feature
<223> OTHER INFORMATION: Incyte ID No: 2155305F6
<221> NAME/KEY: unsure
<222> LOCATION: 61, 106, 131, 177, 181, 187, 275, 312, 343, 393, 432,
      485-486, 491-492
<223> OTHER INFORMATION: a, t, c, g, or other

<400> SEQUENCE: 27
cttggctctc ggccttgtcc agggaggttg ggctaaggag agatggaaac tgccctggga     60
naggaaggga gtccagatcc catgaatagc ccacacaggt accggntctc agagggtccg    120
tgcattcctg ntctccggac ccccaaaggg cccagcattg gtggtgcac  cagtatntta    180
ntatccntct gagcaaatta tccacaaagg atttgcatta cgtcactcga acgttttca     240
tccatgctta gcatctactc tgtataacgc atganagggg aggcaaagaa gaaaaagaca    300
cacagaaggg cntttaaaaa agtagatatt taatatctaa gcnggggagg ggacaggaca    360
gaaagcctgc actgagggt gcggtgccaa canggaaact cttcagctcc ctggcaaacc     420
taccagtgag gntcccagag acgcagctgt ctcagtgcca ggggcagatt gggtgtgact    480
ctccnntcct nnatctcctg c                                              501

<210> SEQ ID NO 28
<211> LENGTH: 276
<212> TYPE: DNA
<213> ORGANISM: Homo sapiens
<220> FEATURE:
<221> NAME/KEY: misc_feature
<223> OTHER INFORMATION: Incyte ID No: 3151704H1
<221> NAME/KEY: unsure
<222> LOCATION: 36
<223> OTHER INFORMATION: a, t, c, g, or other

<400> SEQUENCE: 28
tcctgctgtt gtcctagtgg ctatcacagg cctggntggg tgggttgggg gaggtgtcag     60
tcaccttgtt ggtaacacta aagttgtttt gttggttttt taaaacccca atactgaggt    120
```

```
tcttcctgtt ccctcaagtt ttcttatggg cttccaggct ttaagctaat tccagaagta      180
aaactgatct tgggtttcct attctgcctc ccctagaagg gcagggtgat aacccagcta      240
cagggaatcc cggcccagct ttccacaggc atcaca                                276
```

<210> SEQ ID NO 29
<211> LENGTH: 273
<212> TYPE: DNA
<213> ORGANISM: Homo sapiens
<220> FEATURE:
<221> NAME/KEY: misc_feature
<223> OTHER INFORMATION: Incyte ID No: 4567720H1

<400> SEQUENCE: 29

```
gctttccaca gcatcacag gcatcttccg cggattctag ggtgggctgc ccagccttct      60
ggtctgaggc gcagtccctc tgcccaggtg ctgtgcctat tcaagtggcc ttcaggcaga     120
gcagcaagtg gcccttagcg ccccttccca taagcagctg tggtggcagt gagggaggtt    180
gggtagccct ggactggtcc cctcctcaga tcacccttgc aaatctggcc tcatcttgta    240
ttccaacccg acatccctaa aagtacctcc acc                                  273
```

<210> SEQ ID NO 30
<211> LENGTH: 500
<212> TYPE: DNA
<213> ORGANISM: Homo sapiens
<220> FEATURE:
<221> NAME/KEY: misc_feature
<223> OTHER INFORMATION: Incyte ID No: 1711093F6
<221> NAME/KEY: unsure
<222> LOCATION: 416, 458
<223> OTHER INFORMATION: a, t, c, g, or other

<400> SEQUENCE: 30

```
ttgtattcca acccgacatc cctaaaagta cctccacccg ttccgggtct ggaaggcgtt      60
ggcaccacaa gcactgtccc tgtgggagga gcacaacctt ctcgggacag gatctgatgg    120
ggtcttgggc taaaggaggt ccctgctgtc ctggagaaag tcctagaggt tatctcagga    180
atgactggtg gccctgcccc aacgtggaaa ggtgggaagg aagccttctc ccattagccc    240
caatgagaga actcaacgtg ccggagctga gtgggccttg cacgagacac tggccccact    300
ttcaggcctg gaggaagcat gcacacatgg agacggcgcc tgcctgtaga ctgtttggat    360
cttcgagatc tccccaggca tcttgtctcc cacaggatcg tgtgtgtagg tggtgntgtg    420
tggttttcct ttgtgaagga tagagggaaa ctatttgnag cttgttttat aaaaaataaa    480
aaatgggtaa atcttgaaaa                                                 500
```

<210> SEQ ID NO 31
<211> LENGTH: 619
<212> TYPE: DNA
<213> ORGANISM: Canis familiaris
<220> FEATURE:
<221> NAME/KEY: misc_feature
<223> OTHER INFORMATION: Incyte ID No: 702768776H1

<400> SEQUENCE: 31

```
ggacgcctcg tctaaggagt ggaaaaccac agggcaggtg gagagaccag ggaggcagga      60
cggactgccc gatgcccaac cttcaccagc tccccaggcc cggccacatc ccatgtaaca    120
tgagtggtgc ccaccgtgtt tgcacttttg ataactctca tttgcgtgtt ttcttcctgg    180
ttgcattttt aaacaccagt atctaatacc acagtgggaa aaggaaaggg aaaaagactg    240
tttattctct ctcttattgt aagttttggg atctgctact gacaactttg agggggtttt    300
```

```
gggggcggg tttgggggga gggtgtttgt ttcggggact gagaagaaag agatttatat      360
actgtacata aatatatatg taaattgtat agttcttttg tacaggcgtt ggcattgctg      420
tttgtttatt cccctccctc tccctgctct tgtggcgggg gctctggaca catagcccag      480
ctttctagaa cccagactgt gcccatagcc cacctggatt ccatttggag actgaccctg      540
tgtgtgtgcg taaagactgg agcccgcaga ttatattgtc gactccatcg gttctttctg      600
gtgggagggg ggtactgcc                                                  619

<210> SEQ ID NO 32
<211> LENGTH: 294
<212> TYPE: DNA
<213> ORGANISM: Rattus norvegicus
<220> FEATURE:
<221> NAME/KEY: misc_feature
<223> OTHER INFORMATION: Incyte ID No: 700271122H1

<400> SEQUENCE: 32
agataccctc accacagaca tggttcaggc cattaactca gcagcgccca ctgaaggtgg       60
gaggttctca gagccagacc ccagccacac cctggaggag cgggtggcac actggtactt      120
cagccagctg gatagcaaca gcagtgatga cattaacaag cgggagatga aaccgttcaa      180
gcgctatgtg aagaagaaag ccaagcccaa gaagtgcgcc cggcgcttca ccgactactg      240
tgacctgaac aaggataagg ccatctcgct gcctgagctg aagggctgcc tggg            294

<210> SEQ ID NO 33
<211> LENGTH: 239
<212> TYPE: DNA
<213> ORGANISM: Rattus norvegicus
<220> FEATURE:
<221> NAME/KEY: misc_feature
<223> OTHER INFORMATION: Incyte ID No: 701648524H1

<400> SEQUENCE: 33
gtctgagaag acaggactga ccatcagaca cctaaccttc agcgctgccc gtggtccagc       60
cacagcccat gtaacataag tggtgccctc catgtttgca cttttaataa ctcttatgtg      120
tgtgttctgt ttctggttcc atttgtaaac accagttatc taataccgca gtgggatcag      180
gaaatggaag aaaagctgtt tattctctct tttattgtta agttttttgga tctgctact      239

<210> SEQ ID NO 34
<211> LENGTH: 288
<212> TYPE: DNA
<213> ORGANISM: Rattus norvegicus
<220> FEATURE:
<221> NAME/KEY: misc_feature
<223> OTHER INFORMATION: Incyte ID No: 700306729H1

<400> SEQUENCE: 34
gggctgcctg ggtgttagca agaagttgg acgtctcgtc taaagagcag aaaaatcgaa        60
aggccaatgg agagtctgag aagacaggac tgaccatcag acacctaacc ttcagcgctg      120
cccgtggccc agccacagcc catgtaacat aagtggtgcc ctccatgttt gcacttttaa      180
taactcttat gtgtgtgttc tgtttctggt tccatttgta aaccaccagtt atctaatacc     240 gcagtgggat caggaaaggg aagaaaagct gtttattctc tcttttat                   288

<210> SEQ ID NO 35
<211> LENGTH: 130
<212> TYPE: DNA
<213> ORGANISM: Rattus norvegicus
```

<220> FEATURE:
<221> NAME/KEY: misc_feature
<223> OTHER INFORMATION: Incyte ID No: 700594568H1

<400> SEQUENCE: 35

| | |
|---|---|
| aaaccgttca agcgctatgt gaagaagaaa gccaagccca agaagtgcgc ccggcgcttc | 60 |
| accgactact gtgacctgaa caaggataag gccatctcgc tgcctgagct gaagggctgc | 120 |
| ctgggtgtta | 130 |

<210> SEQ ID NO 36
<211> LENGTH: 505
<212> TYPE: DNA
<213> ORGANISM: Rattus norvegicus
<220> FEATURE:
<221> NAME/KEY: misc_feature
<223> OTHER INFORMATION: Incyte ID No: 701886717H1

<400> SEQUENCE: 36

| | |
|---|---|
| tgggaccaag aagaaagaga tttatatact gtatataaat atatatgtaa attgtataga | 60 |
| tcttttgtac aggcattgac atcactgttt gtcccttccc ttcccaatac ttcctctgga | 120 |
| ctcatagtcc aactctctca aactgtatcc ttagcttacc tgagtttcac tgtggatgga | 180 |
| ctctgtgaga gtagctagga gccctgtgct tgtgctgtgg acaccacgtt ttcttctggt | 240 |
| gagaagaagg tactggtcca tgccattagc tctcaaagtt cagtcacttg gctgttggct | 300 |
| ggtcctcaag cagaccccat ccctgtctcc tgacctgaag gaaatgtgca cagagaagcc | 360 |
| acctctatgt aggagtttag aatctgacca gccgtcttct ctctcacaga tgggcgtagg | 420 |
| ctgtgctgtg tggttttccc ttgggggggc gggagcaagg agaagtattt gtagcttgtt | 480 |
| ttataaaaaa taaaaaaaaa tggat | 505 |

<210> SEQ ID NO 37
<211> LENGTH: 263
<212> TYPE: DNA
<213> ORGANISM: Rattus norvegicus
<220> FEATURE:
<221> NAME/KEY: misc_feature
<223> OTHER INFORMATION: Incyte ID No: 700694069H1

<400> SEQUENCE: 37

| | |
|---|---|
| cttctgtttc tggttccatt tgtaaacacc agttatctaa taccgcaatg ggatcaggaa | 60 |
| agggaagtca agctgtttat tctctctctt attgttaagt ttttggatct gctactgaca | 120 |
| acttgtaggt tatcagggga cgggtgggac caagaagaca gagatttata tactgtatat | 180 |
| aaatttatat gtacaattgt atagatcttt tgtacaggca ttgacatcac tgtttgtctc | 240 |
| ttcccttccc aatacttcct ctg | 263 |

<210> SEQ ID NO 38
<211> LENGTH: 112
<212> TYPE: DNA
<213> ORGANISM: Rattus norvegicus
<220> FEATURE:
<221> NAME/KEY: misc_feature
<223> OTHER INFORMATION: Incyte ID No: 700139225H1

<400> SEQUENCE: 38

| | |
|---|---|
| cagcaaagca ggtactcctg caagatcatg aatggtgttc tctggagccg ggtttctgt | 60 |
| ccaccgcaca ggttctcaga gccagacccc agccacaccc tggaggagcg gg | 112 |

<210> SEQ ID NO 39

```
<211> LENGTH: 216
<212> TYPE: DNA
<213> ORGANISM: Rattus norvegicus
<220> FEATURE:
<221> NAME/KEY: misc_feature
<223> OTHER INFORMATION: Incyte ID No: 700888003H1

<400> SEQUENCE: 39
tggaccgagc aagttgaaga gtccggcaga gacaaggacc agataagaaa tatgagcatc    60
cctcctgtga tcaagagcac cagtcggctc ttgaggaagc caagcaaccc aagaatgaca   120
atgtagtgat ccctgagtgt acacacggcg gcctctacaa gccagtgcaa tgccacccat   180
ccactggata ctgctggtgt gtgctggtag acactg                              216

<210> SEQ ID NO 40
<211> LENGTH: 208
<212> TYPE: DNA
<213> ORGANISM: Rattus norvegicus
<220> FEATURE:
<221> NAME/KEY: misc_feature
<223> OTHER INFORMATION: Incyte ID No: 701234138H1

<400> SEQUENCE: 40
ggatgcgctc tccactgaca tggtccacgc cgtctctgac ccctcttcct catctggcag    60
gctgtcagag ccagacccca gccacaccct ggaggagagg gttgtgcatt gggacttcaa   120
gctgcttgat aagaactcta gcggagacat tggcaagaag gaaatcaaac cctttaagag   180
gttcctgcga aagaaatcca agcccaaa                                       208

<210> SEQ ID NO 41
<211> LENGTH: 452
<212> TYPE: PRT
<213> ORGANISM: Mus musculus
<220> FEATURE:
<221> NAME/KEY: misc_feature
<223> OTHER INFORMATION: Incyte ID No: g5305327

<400> SEQUENCE: 41

Met Leu Pro Ala Arg Val Arg Leu Leu Thr Pro His Leu Leu Leu
 1               5                  10                  15

Val Leu Val Gln Leu Ser Pro Ala Gly Gly His Arg Thr Thr Gly
                20                  25                  30

Pro Arg Phe Leu Ile Ser Asp Arg Asp Pro Pro Cys Asn Pro His
                35                  40                  45

Cys Pro Arg Thr Gln Pro Lys Pro Ile Cys Ala Ser Asp Gly Arg
                50                  55                  60

Ser Tyr Glu Ser Met Cys Glu Tyr Gln Arg Ala Lys Cys Arg Asp
                65                  70                  75

Pro Ala Leu Ala Val Val His Arg Gly Arg Cys Lys Asp Ala Gly
                80                  85                  90

Gln Ser Lys Cys Arg Leu Glu Arg Ala Gln Ala Leu Glu Gln Ala
                95                 100                 105

Lys Lys Pro Gln Glu Ala Val Phe Val Pro Glu Cys Gly Glu Asp
               110                 115                 120

Gly Ser Phe Thr Gln Val Gln Cys His Thr Tyr Thr Gly Tyr Cys
               125                 130                 135

Trp Cys Val Thr Pro Asp Gly Lys Pro Ile Ser Gly Ser Ser Val
               140                 145                 150

Gln Asn Lys Thr Pro Val Cys Ser Gly Pro Val Thr Asp Lys Pro
               155                 160                 165
```

-continued

```
Leu Ser Gln Gly Asn Ser Gly Arg Lys Asp Asp Gly Ser Lys Pro
                170                 175                 180

Thr Pro Thr Met Glu Thr Gln Pro Val Phe Asp Gly Asp Glu Ile
                185                 190                 195

Thr Ala Pro Thr Leu Trp Ile Lys His Leu Val Ile Lys Asp Ser
                200                 205                 210

Lys Leu Asn Asn Thr Asn Val Arg Asn Ser Glu Lys Val His Ser
                215                 220                 225

Cys Asp Gln Glu Arg Gln Ser Ala Leu Glu Glu Ala Arg Gln Asn
                230                 235                 240

Pro Arg Glu Gly Ile Val Ile Pro Glu Cys Ala Pro Gly Gly Leu
                245                 250                 255

Tyr Lys Pro Val Gln Cys His Gln Ser Thr Gly Tyr Cys Trp Cys
                260                 265                 270

Val Leu Val Asp Thr Gly Arg Pro Leu Pro Gly Thr Ser Thr Arg
                275                 280                 285

Tyr Val Met Pro Ser Cys Glu Ser Asp Ala Arg Ala Lys Ser Val
                290                 295                 300

Glu Ala Asp Asp Pro Phe Lys Asp Arg Glu Leu Pro Gly Cys Pro
                305                 310                 315

Glu Gly Lys Lys Met Glu Phe Ile Thr Ser Leu Leu Asp Ala Leu
                320                 325                 330

Thr Thr Asp Met Val Gln Ala Ile Asn Ser Ala Ala Pro Thr Gly
                335                 340                 345

Gly Gly Arg Phe Ser Glu Pro Asp Pro Ser His Thr Leu Glu Glu
                350                 355                 360

Arg Val Ala His Trp Tyr Phe Ser Gln Leu Asp Ser Asn Ser Ser
                365                 370                 375

Asp Asp Ile Asn Lys Arg Glu Met Lys Pro Phe Lys Arg Tyr Val
                380                 385                 390

Lys Lys Lys Ala Lys Pro Lys Lys Cys Ala Arg Arg Phe Thr Asp
                395                 400                 405

Tyr Cys Asp Leu Asn Lys Asp Lys Val Ile Ser Leu Pro Glu Leu
                410                 415                 420

Lys Gly Cys Leu Gly Val Ser Lys Glu Gly Gly Ser Leu Gly Ser
                425                 430                 435

Phe Pro Gln Gly Lys Arg Ala Gly Thr Asn Pro Phe Ile Gly Arg
                440                 445                 450

Leu Val
```

DNA ENCODING SPARC-RELATED PROTEINS

This application is a continuation-in-part of U.S. Ser. No. 09/349,015 filed Jul. 7, 1999.

FIELD OF THE INVENTION

This invention relates to mammalian cDNAs which encode SPARC-related proteins and to the use of the cDNAs and the encoded proteins in the diagnosis and treatment of cell proliferative disorders.

BACKGROUND OF THE INVENTION

Phylogenetic relationships among organisms have been demonstrated many times, and studies from a diversity of prokaryotic and eukaryotic organisms suggest a more or less gradual evolution of molecules, biochemical and physiological mechanisms, and metabolic pathways. Despite different evolutionary pressures, the proteins of nematode, fly, rat, and man have common chemical and structural features and generally perform the same cellular function. Comparisons of the nucleic acid and protein sequences from organisms where structure and/or function are known accelerate the investigation of human sequences and allow the development of model systems for testing diagnostic and therapeutic agents for human conditions, diseases, and disorders.

The interaction of a cell with its surrounding extracellular matrix (ECM) influences cell behavior. The ECM, composed of fibrous proteins, proteoglycans and glycoproteins, fills the extracellular space with an elaborate protein network that establishes cellular shape, adhesion, detachment, motility, growth, division, and differentiation. Variations in the composition of the ECM determine the distinctive character of tissues and account for differences in strength and flexibility of connective tissues such as skin, bone, tendon, ligament and cartilage. Restructuring of the ECM accompanies embryonic development, tissue remodeling, angiogenesis, and wound healing.

Glycoproteins of the ECM typically contain multiple domains that mediate protein-protein interactions among ECM proteins and between ECM proteins and cell surface receptors. They frequently contain a variety of post-translational modifications that are required for their function, including covalently attached N- and O-linked complex-carbohydrates, phosphorylated serine and threonine residues and sulfated tyrosine residues. SPARC, an abbreviation for secreted protein acidic and rich in cysteine, also termed osteonectin, BM-40, and 43K protein, is an ECM glycoprotein that carries out multiple functions (Lane and Sage (1994) FASEB J 163–173; Motamed (1999) Int J Biochem Cell Biol 31:1363–1366). It has a molecular weight of 33 kDa in the absence of post-translational modifications, is 303 amino acids in length, and contains covalently attached N-linked complex-type carbohydrate and a signal peptide of 17 amino acids. Among its roles, SPARC modulates cell shape, adhesion, and migration of cells. Cells which over-express SPARC have a rounded morphology, whereas cells which under-express SPARC flatten. Acting as an anti-adhesin, SPARC disrupts interactions of cells with other ECM proteins. It is expressed during embryogenesis, tissue remodeling and repair. SPARC is present at high levels in developing bone and teeth, where it may be involved in calcification and calcium ion binding and may function in the development of ossified and mineralized tissues. SPARC is also present at high concentrations in activated platelets and megakaryocytes. SPARC binds cytokines, divalent cations, several collagen types, hydroxyapatite, albumin, thrombospondin and cell membranes on platelets and endothelial cells. It modulates the responses of cells to cytokines and inhibits the progression of the cell cycle from $G_1$ to S phase.

SPARC is made up of three domains, which individually have been shown to carry out specific functions (Motamed, supra). The acidic domain binds $Ca^{2+}$, inhibits cell spreading and chemotactic responses to growth factors, modulates levels of plasminogen activator inhibitor-1, fibronectin, and thrombospondin-1. The cysteine-rich domain has homology with follistatin, an inhibitor of transforming growth factor b-like cytokines, and also shows similarity to serpin-type protease inhibitors and epidermal growth factor (EGF)-like motifs. This domain controls cell proliferation, angiogenesis, and disassembly of focal adhesions that link the ECM to the actin cytoskeleton. The extracellular calcium-binding domain contains an EF-hand motif, binds to cells and several types of collagen, induces matrix metalloproteinases, inhibits cell spreading and proliferation, and controls focal adhesions. Binding of collagen is dependent on $Ca^{2+}$ and the state of protein glycosylation.

During normal development, angiogenesis, and wound healing, SPARC modulates the effects of a variety of growth factors involved in cell cycle control, cell migration, and proliferation. Perturbed cellular regulation by growth factors is associated with altered levels of SPARC expression and pathological processes in various tissues. For example, SPARC shows high levels of expression in lesions of atherosclerosis compared to normal vessels (Raines et al. (1992) Proc Natl Acad Sci 89:1281–1285). It controls the activity of platelet-derived growth factor (PDGF), which promotes cell migration, proliferation, and cellular metabolic changes. SPARC binds to PDGF and inhibits its interaction with receptors. By regulating the availability of PDGF in response to vascular injury, SPARC may control proliferative repair processes. SPARC delays the entry of aortic endothelial cells into S phase and may facilitate withdrawal from the cell cycle in response to injury or developmental signals (Funk and Sage (1991) Proc Natl Acad Sci 88:2648–2652). SPARC may also play a role in the calcification of atherosclerotic plaques (Watson et al. (1994) J Clin Invest 93:2106–2113).

SPARC shows high levels of expression in brain tumor cells in gliomas where it controls the activity of vascular endothelial growth factor (VEGF), the principal angiogenic growth factor identified in human astroglial tumors (Vajkoczy et al. (2000) Int J Cancer 87:261–268). VEGF participates in a signal-transduction pathway that mediates glioma angiogenesis through stimulation of tyrosine phosphorylation and activation of mitogen-activated protein kinases. SPARC binds to VEGF and inhibits its association with cell-surface receptors. In addition, the anti-adhesive properties of SPARC and its ability to induce and activate proteolytic enzymes that degrade the ECM may also play roles in promoting cell migration and tumor cell infiltration into surrounding tissue.

Overexpression of SPARC is also associated with osteoarthritis and rheumatoid arthritis (Nakamura et al. (1996) Arthritis and Rheumatism 39:539–551). High levels of SPARC are found in cartilage and synovial fluids of patients with osteoarthritis or rheumatoid arthritis compared to levels in normal cartilage. Levels of SPARC increase in articular chondrocyte cultures in response to transforming growth factor b1 and bone morphogenetic protein 2 and decrease in response to inflammatory cytokines, IL-1b, IL-1a, tumor necrosis factor a, lipospolysaccharide, phorbol myristate acetate, basic fibroblast growth factor, and dexamethasone. SPARC activates expression of matrix metalloproteinases in synovial fibroblasts and may play roles in the destruction and repair of cartilage.

In addition, aberrant expression of SPARC is associated with a number of other diseases. SPARC shows high levels of expression in breast, ovarian and prostate cancer where it may facilitate tumor progression through control of cell adhesion, growth factors and matrix metalloproteinase activity (Gilles et al. (1998) Cancer Res 58:5529–5536; Porter et al. (1995) J Histochem Cytochem 43:791–800; Brown et al. (1999) Gynecol Oncol 75:25–33; Thomas et al. (2000) Clin Cancer Res 6:1140–1149). Elevated expression of SPARC is associated with Scleroderma (Unemori and Amento (1991) Curr Opin Rheumatol 3:953–959), human lens cataracts (Kantorow et al. (2000) Mol Vis 6:24–29) and ECM deposits in renal disease (Bassuk et al. (2000) Kidney Int 57:117–128). The discovery of mammalian cDNAs encoding SPARC-related proteins satisfies a need in the art by providing compositions which are useful in the diagnosis and treatment of cell proliferative disorders.

SUMMARY OF THE INVENTION

The invention is based on the discovery of mammalian cDNAs which encodes mammalian SPARC-related proteins, SPARC-1 and SPARC-2, which are useful in the diagnosis and treatment of atherosclerosis, anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis.

The invention provides an isolated mammalian cDNA or a fragment thereof encoding mammalian proteins or portions thereof selected from the amino acid sequences of SEQ ID NO:1 or SEQ ID NO: 2, a variant having at least 56% identity to the amino acid sequences of SEQ ID NO:1 or SEQ ID NO: 2, antigenic epitopes of SEQ ID NO:1 or SEQ ID NO:2, oligopeptides of SEQ ID NO:1 or SEQ ID NO:2, and biologically active portions of SEQ ID NO:1 or SEQ ID NO:2.

The invention also provides an isolated mammalian cDNA or the complement thereof selected from the nucleic acid sequences of SEQ ID NO:3, a variant having at least 83% identity to the nucleic acid sequence of SEQ ID NO:3, a fragment of SEQ ID NOs:4–13, and an oligonucleotide of SEQ ID NO:3. The invention additionally provides a composition, a substrate, and a probe comprising the cDNA, or the complement of the cDNA, encoding SPARC-1. The invention further provides a vector containing the cDNA, a host cell containing the vector and a method for using the cDNA to make SPARC-1. The invention still further provides a transgenic cell line or organism comprising a vector containing the cDNA encoding SPARC-1. The invention additionally provides a mammalian fragment or the complement thereof selected from the group consisting of SEQ ID NOs:14–19. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention also provides an isolated mammalian cDNA or the complement thereof selected from the group consisting of nucleic acid sequences of SEQ ID NO:20, a variant having 84% identity to the nucleic acid sequence of SEQ ID NO:20, a fragment of SEQ ID NOs:21–30, an oligonucleotide of SEQ ID NO:20. The invention additionally provides a composition, a substrate, and a probe comprising the cDNA, or the complement of the cDNA, encoding SPARC-2. The invention further provides a vector containing the cDNA, a host cell containing the vector and a method for using the cDNA to make SPARC-2. The invention still further provides a transgenic cell line or organism comprising a vector containing the cDNA encoding SPARC-2. The invention additionally provides a mammalian fragment or the complement thereof selected from the group consisting of SEQ ID NOs:31–40. In one aspect, the invention provides a substrate containing at least one of these fragments. In a second aspect, the invention provides a probe comprising the fragment which can be used in methods of detection, screening, and purification. In a further aspect, the probe is a single stranded complementary RNA or DNA molecule.

The invention provides a method for using a cDNA to detect the differential expression of a nucleic acid in a sample comprising hybridizing a probe to the nucleic acids, thereby forming hybridization complexes and comparing hybridization complex formation with a standard, wherein the comparison indicates the differential expression of the cDNA in the sample. In one aspect, the method of detection further comprises amplifying the nucleic acids of the sample prior to hybridization. In another aspect, the method showing differential expression of the cDNA is used to diagnose atherosclerosis or a cell proliferative disorder. In another aspect, the cDNA or a fragment or a complement thereof may comprise an element on an array.

The invention additionally provides a method for using a cDNA or a fragment or a complement thereof to screen a library or plurality of molecules or compounds to identify at least one ligand which specifically binds the cDNA, the method comprising combining the cDNA with the molecules or compounds under conditions allowing specific binding, and detecting specific binding to the cDNA, thereby identifying a ligand which specifically binds the cDNA. In one aspect, the molecules or compounds are selected from aptamers, DNA molecules, RNA molecules, peptide nucleic acids, artificial chromosome constructions, peptides, transcription factors, repressors, and regulatory molecules.

The invention provides a purified mammalian protein or a portion thereof selected from the group consisting of an amino acid sequence of SEQ ID NO:1, a variant having at least 56% identity to the amino acid sequence of SEQ ID NO:1, an antigenic epitope of SEQ ID NO:1, an oligopeptide of SEQ ID NO:1, and a biologically active portion of SEQ ID NO:1. The invention also provides a composition comprising the purified protein or a portion thereof in conjunction with a pharmaceutical carrier. The invention further provides a method of using the SPARC-1 to treat a subject with a cell proliferative disorder comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with atherosclerosis or a cell proliferative disorder.

The invention provides a purified mammalian protein or a portion thereof selected from the group consisting of an amino acid sequence of SEQ ID NO:2, a variant having at least 56% identity to the amino acid sequence of SEQ ID NO:2, an antigenic epitope of SEQ ID NO:2, an oligopeptide of SEQ ID NO:2, and a biologically active portion of SEQ ID NO:2. The invention also provides a composition comprising the purified protein or a portion thereof in conjunction with a pharmaceutical carrier. The invention further provides a method of using the SPARC-2 to treat a subject with a cell proliferative disorder comprising administering to a patient in need of such treatment the composition containing the purified protein. The invention still further provides a method for using a protein to screen a library or a plurality of molecules or compounds to identify at least one ligand, the method comprising combining the protein with the molecules or compounds under conditions to allow specific binding and detecting specific binding, thereby identifying a ligand which specifically binds the protein. In one aspect, the molecules or compounds are selected from DNA molecules, RNA molecules, peptide nucleic acids, peptides, proteins, mimetics, agonists, antagonists, antibodies, immunoglobulins, inhibitors, and drugs. In another aspect, the ligand is used to treat a subject with a cell proliferative disorder.

The invention provides a method of using a mammalian protein to screen a subject sample for antibodies which specifically bind the protein comprising isolating antibodies from the subject sample, contacting the isolated antibodies with the protein under conditions that allow specific binding, dissociating the antibody from the bound-protein, and comparing the quantity of antibody with known standards, wherein the presence or quantity of antibody is diagnostic of atherosclerosis or a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis.

The invention also provides a method of using a mammalian protein to prepare and purify antibodies comprising immunizing a animal with the protein under conditions to elicit an antibody response, isolating animal antibodies, attaching the protein to a substrate, contacting the substrate with isolated antibodies under conditions to allow specific binding to the protein, and dissociating the antibodies from the protein, thereby obtaining purified antibodies.

The invention provides purified antibodies which bind specifically to polypeptides comprising the amino acid sequences selected from SEQ ID NOs:1 and 2 and fragments thereof. The invention also provides a method of using an antibody to diagnose atherosclerosis and cell proliferative disorders comprising combining the antibody comparing the quantity of bound antibody to known standards, thereby establishing the presence of atherosclerosis or a cell proliferative disorder, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis. The invention further provides a method of using an antibody to treat atherosclerosis and cell proliferative disorders comprising administering to a patient in need of such treatment a pharmaceutical composition comprising the purified antibody.

The invention provides a method for inserting a marker gene into the genomic DNA of a mammal to disrupt the expression of the endogenous polynucleotide. The invention also provides a method for using a cDNA to produce a mammalian model system, the method comprising constructing a vector containing the cDNA selected from SEQ ID NOs:3–40, transforming the vector into an embryonic stem cell, selecting a transformed embryonic stem, microinjecting the transformed embryonic stem cell into a mammalian blastocyst, thereby forming a chimeric blastocyst, transferring the chimeric blastocyst into a pseudopregnant dam, wherein the dam gives birth to a chimeric offspring containing the cDNA in its germ line, and breeding the chimeric mammal to produce a homozygous, mammalian model system.

BRIEF DESCRIPTION OF THE FIGURES AND TABLE

FIGS. 1A, 1B, 1C, 1D, 1E, 1F, 1G, 1H and 1I show the mammalian SPARC-1 (SEQ ID NO:1) encoded by the cDNA (SEQ ID NO:3). The translation was produced using MACDNASIS PRO software (Hitachi Software Engineering, South San Francisco Calif.).

FIGS. 2A, 2B, 2C, 2D, 2E, 2F, 2G, 2H, 2I and 2J show the mammalian SPARC-2 (SEQ NO:2) encoded by the cDNA (SEQ ID NO:20). The translation was produced using MACDNASIS PRO software (Hitachi Software Engineering).

FIGS. 3A, 3B, and 3C demonstrate the conserved chemical and structural similarities among the sequences of SPARC-1 (2617724.orf 1; SEQ ID NO: 1), SPARC-2 (6899373.orf2; SEQ ID NO:2), and Mus musculus SPARC-related protein (g5305327; SEQ ID NO:41). The alignment was produced using the MEGALIGN program of LASERGENE software (DNASTAR, Madison Wis.).

Tables 1A and 1B show the northern analysis for SPARC-1 produced using the LIFESEQ Gold database (Incyte Genomics, Palo Alto Calif.). In Table 1A, the first column presents the tissue categories; the second column, the number of clones in the tissue category; the third column, the number of libraries in which at least one transcript was found; the fourth column, absolute abundance of the transcript; and the fifth column, percent abundance of the transcript. Table 1B shows expression of SPARC-1 in tissues from patients with a cell proliferative disorder. The first column lists the library name, the second column, the number of clones sequenced for that library; the third column, the description of the tissue; the fourth column, the absolute abundance of the transcript; and the fifth column, the percent abundance of the transcript.

Tables 2A and 2B show the northern analysis for SPARC-2 produced using the LIFESEQ Gold database (Incyte Genomics, Palo Alto Calif.). In Table 2A, the first column presents the tissue categories; the second column, the number of clones in the tissue category; the third column, the number of libraries in which at least one transcript was found; the fourth column, the absolute abundance of the transcript; and the fifth column, the percent abundance of the transcript. Table 2B shows expression of SPARC-1 in tissues from patients with cell proliferative disorders. The first column lists the library name, the second column, the number of clones sequenced for that library; the third column, description of the tissue; the fourth column, absolute abundance of the transcript; and the fifth column, percent abundance of the transcript.

DESCRIPTION OF THE INVENTION

It is understood that this invention is not limited to the particular machines, materials and methods described. It is also to be understood that the terminology used herein is for the purpose of describing particular embodiments and is not intended to limit the scope of the present invention which will be limited only by the appended claims. As used herein, the singular forms "a", "an", and "the" include plural reference unless the context clearly dictates otherwise. For example, a reference to "a host cell" includes a plurality of such host cells known to those skilled in the art.

Unless defined otherwise, all technical and scientific terms used herein have the same meanings as commonly understood by one of ordinary skill in the art to which this invention belongs. All publications mentioned herein are cited for the purpose of describing and disclosing the cell lines, protocols, reagents and vectors which are reported in the publications and which might be used in connection with the invention. Nothing herein is to be construed as an admission that the invention is not entitled to antedate such disclosure by virtue of prior invention.

Definitions

"SPARC-1" and "SPARC-2" refer to substantially purified protein obtained from any mammalian species, including bovine, canine, murine, ovine, porcine, rodent, simian, and preferably the human species, and from any source, whether natural, synthetic, semi-synthetic, or recombinant.

"Array" refers to an ordered arrangement of at least two cDNAs on a substrate. At least one of the cDNAs represents a control or standard sequence, and the other, a cDNA of diagnostic interest. The arrangement of from about two to about 40,000 cDNAs on the substrate assures that the size and signal intensity of each labeled hybridization complex formed between a cDNA and a sample nucleic acid is individually distinguishable.

The "complement" of a cDNA of the Sequence Listing refers to a nucleic acid molecule which is completely complementary over its full length and which will hybridize to the cDNA or an mRNA under conditions of high stringency.

"cDNA" refers to an isolated polynucleotide, nucleic acid molecule, or any fragment or complement thereof. It may have originated recombinantly or synthetically, be double-stranded or single-stranded, represent coding and/or non-coding sequence, an exon with or without an intron from a genomic DNA molecule.

The phrase "cDNA encoding a protein" refers to a nucleic acid sequence that closely aligns with sequences which encode conserved regions, motifs or domains that were identified by employing analyses well known in the art. These analyses include BLAST (Basic Local Alignment Search Tool; Altschul (1993) J Mol Evol 36: 290–300; Altschul et al. (1990) J Mol Biol 215:403410) which provides identity within the conserved region.

"Derivative" refers to a cDNA or a protein that has been subjected to a chemical modification. Derivatization of a cDNA can involve substitution of a nontraditional base such as queosine or of an analog such as hypoxanthine. These substitutions are well known in the art. Derivatization of a protein involves the replacement of a hydrogen by an acetyl, acyl, alkyl, amino, formyl, or morpholino group. Derivative molecules retain the biological activities of the naturally occurring molecules but may confer advantages such as longer lifespan or enhanced activity.

"Differential expression" refers to an increased, upregulated or present, or decreased, downregulated or absent, gene expression as detected by the absence, presence, or at least two-fold changes in the amount of transcribed messenger RNA or translated protein in a sample.

"Disorder" refers to conditions, diseases or syndromes in which the cDNAs and SPARC-1 or SPARC-2 are differentially expressed, particularly atherosclerosis; cell proliferative disorders, such as brain tumors, including anaplastic oligodendroglioma, astrocytoma, oligoastrocytoma, glioblastoma, meningioma, ganglioneuroma, neuronal neoplasm; cancers, including breast adenocarcinoma, prostate adenocarcinoma, stomach adenocarcinoma, metastasizing neuroendocrine carcinoma; autoimmune diseases, including multiple sclerosis and rheumatoid arthritis; Huntington's disease; fibrocystic breast disease; cholecystitis and cholelithiasis; and osteoarthritis.

"Fragment" refers to a chain of consecutive nucleotides from about 200 to about 700 base pairs in length. Fragments may be used in PCR or hybridization technologies to identify related nucleic acid molecules and in binding assays to screen for a ligand. Nucleic acids and their ligands identified in this manner are useful as therapeutics to regulate replication, transcription or translation.

A "hybridization complex" is formed between a cDNA and a nucleic acid of a sample when the purines of one molecule hydrogen bond with the pyrimidines of the complementary molecule, e.g., 5'-A-G-T-C-3' base pairs with 3'-T-C-A-G-5'. The degree of complementarity and the use of nucleotide analogs affect the efficiency and stringency of hybridization reactions.

"Ligand" refers to any agent, molecule, or compound which will bind specifically to a complementary site on a cDNA molecule or polynucleotide, or to an epitope or a protein. Such ligands stabilize or modulate the activity of polynucleotides or proteins and may be composed of inorganic or organic substances including nucleic acids, proteins, carbohydrates, fats, and lipids.

"Oligonucleotide" refers a single stranded molecule from about 18 to about 60 nucleotides in length which may be used in hybridization or amplification technologies or in regulation of replication, transcription or translation. Substantially equivalent terms are amplimer, primer, and oligomer.

"Portion" refers to any part of a protein used for any purpose; but especially, to an epitope for the screening of ligands or for the production of antibodies.

"Post-translational modification" of a protein can involve lipidation, glycosylation, phosphorylation, acetylation, racemization, proteolytic cleavage, and the like. These processes may occur synthetically or biochemically. Biochemical modifications will vary by cellular location, cell type, pH, enzymatic milieu, and the like.

"Probe" refers to a cDNA that hybridizes to at least one nucleic acid in a sample. Where targets are single stranded, probes are complementary single strands. Probes can be labeled with reporter molecules for use in hybridization reactions including Southern, northern, in situ, dot blot, array, and like technologies or in screening assays.

"Protein" refers to a polypeptide or any portion thereof. A "portion" of a protein refers to that length of amino acid sequence which would retain at least one biological activity, a domain identified by PFAM or PRINTS analysis or an antigenic epitope of the protein identified using Kyte-Doolittle algorithms of the PROTEAN program (DNASTAR, Madison Wis.). An "oligopeptide" is an amino acid sequence from about five residues to about 15 residues that is used as part of a fusion protein to produce an antibody.

"Purified" refers to any molecule or compound that is separated from its natural environment and is from about 60% free to about 90% free from other components with which it is naturally associated "Sample" is used in its broadest sense as containing nucleic acids, proteins, antibodies, and the like. A sample may comprise a bodily fluid; the soluble fraction of a cell preparation, or an aliquot of media in which cells were grown; a chromosome, an organelle, or membrane isolated or extracted from a cell; genomic DNA, RNA, or cDNA in solution or bound to a substrate; a cell; a tissue; a tissue print; a fingerprint, buccal cells, skin, or hair; and the like.

"Specific binding" refers to a special and precise interaction between two molecules which is dependent upon their structure, particularly their molecular side groups. For example, the intercalation of a regulatory protein into the major groove of a DNA molecule, the hydrogen bonding along the backbone between two single stranded nucleic acids, or the binding between an epitope of a protein and an agonist, antagonist, or antibody.

"Similarity" as applied to sequences, refers to the quantification (usually percentage) of nucleotide or residue matches between at least two sequences aligned using a standardized algorithm such as Smith-Waterman alignment (Smith and Waterman (1981) J Mol Biol 147:195–197) or BLAST2 (Altschul et al. (1997) Nucleic Acids Res 25:3389–3402). BLAST2 may be used in a standardized and reproducible way to insert gaps in one of the sequences in order to optimize alignment and to achieve a more meaningful comparison between them.

"Substrate" refers to any rigid or semi-rigid support to which cDNAs or proteins are bound and includes membranes, filters, chips, slides, wafers, fibers, magnetic or nonmagnetic beads, gels, capillaries or other tubing, plates, polymers, and microparticles with a variety of surface forms including wells, trenches, pins, channels and pores.

"Variant" refers to molecules that are recognized variations of a cDNA or a protein encoded by the cDNA. Splice variants may be determined by BLAST score, wherein the score is at least 100, and most preferably at least 400. Allelic variants have a high percent identity to the cDNAs and may differ by about three bases per hundred bases. "Single nucleotide polymorphism" (SNP) refers to a change in a single base as a result of a substitution, insertion or deletion. The change may be conservative (purine for purine) or non-conservative (purine to pyrimidine) and may or may not result in a change in an encoded amino acid or its secondary, tertiary, or quaternary structure.

THE INVENTION

The invention is based on the discovery of cDNAs which encode SPARC-1 and SPARC-2 and on the use of the cDNAs, or fragments thereof, and proteins, or portions thereof, directly or as compositions in the characterization, diagnosis, and treatment of atherosclerosis and cell proliferative disorders, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis.

SPARC-1 of the present invention was discovered using a method for identifying gene sequences which coexpress with known genes associated with atherosclerosis in a plurality of samples. The known atherosclerosis genes are listed and their expression described in U.S. Ser. No. 09/349,015 filed Jul. 7, 1999 incorporated by reference herein.

Nucleic acids encoding SPARC-1 of the present invention were first identified in Incyte Clone 2617724 from the gallbladder cDNA library (GBLANOT01) using a computer search for amino acid sequence alignments. A consensus sequence, SEQ ID NO:3, was derived from the following overlapping and/or extended nucleic acid sequences (SEQ ID NO:4–13): Incyte Clones 1388229H1 (CARGDIT02), 2617724F6 (GBLANOT01), 2081850F6 (UTRSNOT08), 2313837H1 (NGANNOT01), 1804413F6 (SINTNOT13), 3207379H1 (PENCNOT03), 2347051F6 (TESTTUT02), 1259341F1 (MENITUT03), 1804413T6 (SINTNOT13), and 081943R1 (SYNORAB01). Table 1A shows expression of the transcript across the tissue categories (also listed in Example IV). SPARC-1 is expressed predominantly in exocrine glands, female and male reproductive tissue, and in the musculoskeletal system. Table 1B shows expression of the transcript in gastrointestinal, breast, prostate, musculoskeletal system, and nervous system tissues, particularly in tissues from patients with cell proliferative disorders. Overexpression of SPARC-1 in libraries (STOMTUP02, BRSTTUT15, BRSTTUT02, PROSTUS23, PROSTUT04) is associated with adenocarcinoma in stomach, breast, and prostate tissues. In addition, overexpression in breast libraries (BRSTTMT02 and BRSTTMC01) is associated with nonproliferative fibrocystic and proliferative fibrocystic breast disease. Overexpression in libraries (BRAITUT26, BRAIDIT01, MENITUT03, BRAITUT07, and NGANNOT01) is associated with brain and neuroganglion tumors. Overexpression in libraries (CARGDIT02, CARGDIT01, SYNORAB01) is associated with osteoarthritis, and rheumatoid arthritis in cartilage and hip. Overexpression in gallbladder (GBLANOT02) is associated with cholecystitis and cholelithiasis. A fragment thereof the cDNA from about nucleotide 559 to about nucleotide 609 is also useful in diagnostic assays.

Nucleic acids encoding SPARC-2 of the present invention were first identified in Incyte Clone 6899373 from the liver cDNA library (LIVRTMR01) using a computer search for amino acid sequence alignments. A consensus sequence, SEQ ID NO:20, was derived from the following overlapping and/or extended nucleic acid sequences (SEQ ID NO:21–30): Incyte Clones 6899373H1 (LIVRTMR01), 6898356H1 (LIVRTMR01), 6977387H1 (BRAHTDR04), 6835981H1 (BRSTNON02), 3316785T6 (PROSBPT03), 746080R1 (BRAITUT01), 2155305F6 (BRAINOT09), 3151704H1 (ADRENON04), 4567720H1 (HELATXT01), and 1711093F6 (PROSNOT16). Table 2A shows expression of the transcript across the tissue categories (also listed in Example IV). SPARC-2 is expressed predominantly in germ cells, liver and the nervous system. Table 2B shows expression of the transcript in female and male reproductive tissues, liver, and the nervous system particularly in tissues from patients with cell proliferative and neurological disorders. SPARC-2 shows increased expression in a cervical tumor line library (HELATXT01) in response to treatment with inflammatory-cytokines, tumor necrosis factor-alpha and IL-1 beta. SPARC-2 is overexpressed in brain tumor libraries (BRAITUT12, BRAITUT01, BRAITUP02, BRAITUP02) and in nervous system tissue from patients with neurological diseases such as Huntington's (BRAYDIN03) and multiple sclerosis (NERVMSMSM01). SPARC-2 is also overexpressed in a prostate tumor library (PROSTUS19). In addition, SPARC-2 shows underexpression in a library from metastasizing neuroendocrine carcinoma (LIVRTUT1) compared to a library from microscopically normal tissue (LIVRTUMR01) from the same donor. A fragment thereof the cDNA from about nucleotide 158 to about nucleotide 208 is also useful in diagnostic assays.

In one embodiment, the invention encompasses a polypeptide comprising the amino acid sequence of SEQ ID NO:1. SPARC-1 is 446 amino acids in length and has one potential amidation site at 1367, two N-glycosylation sites at N206 and N362; three potential cAMP-dependent protein kinase phosphorylation sites at T97, S383 and T429; ten potential protein casein kinase II phosphorylation sites at S62, S156, S214, S222, T274, S315, S339, T346, S363, and S405; ten potential protein kinase C phosphorylation sites at T150, T167, T208, T265, T273, S273, T284, S335, T424, T429, S438; one potential tyrosine kinase phosphorylation site at Y96; and three potential N-myristoylation sites at G143, G166, and G303. Analyses by MOTIFS, PFAM, PRINTS, and BLOCKS indicate that the regions of SPARC-1 from F109 to C153 and from 1237 to C281 are similar to a thyroglobulin type-1 repeat signature; the region from L379 to D423 is similar to an osteonectin domain; the regions from V351 to K382 and D397 to L409 are similar to an EF-hand calcium binding domain; the region from C40 to C84 is similar to a Kazal-type serine protease inhibitor domain; and the regions from C124 to S142 and from C251 to 1269 are similar to a type III EGF-like signature. These domains are found in SPARC and the mouse SPARC-related protein (g5305327; SEQ ID NO:41). As shown in FIGS. 3A, 3B, and 3C, SPARC-1 has chemical and structural similarity with a mouse SPARC-related protein (g5305327; SEQ ID NO:41). In particular, SPARC-1 and the mouse SPARC-related protein share 56% identity. An antibody which specifically binds SPARC-1 is useful in assays to diagnose adenocarcinoma, brain and neuroganglion tumors, multiple sclerosis, osteoarthritis and rheumatoid arthritis. Exemplary portions of SEQ ID NO:1 are an antigenic epitope, residue A416 to residue G446 of SEQ ID NO:1 (identified using the PROTEAN program (DNASTAR); and a biologically active portion, the conserved osteonectin domain, residue L379 to residue D423 of SEQ ID NO:1.

In another embodiment, the invention encompasses a polypeptide comprising the amino acid sequence of SEQ ID NO:2. SPARC-2 is 434 amino acids in length and has two potential amidation sites at S172 and E317, two N-glycosylation sites at N214 and N374; one potential cAMP-dependent protein kinase phosphorylation site at T405; ten potential protein casein kinase II phosphorylation sites at S37, S65, S161, S233, T301, S306. S351, T358, S369, and S417; six potential protein kinase C phosphorylation sites at S37, T163, S172, S221, T276, and S284; one potential tyrosine kinase phosphorylation site at Y225; and three potential N-myristoylation sites at G91, G314, and G347. Analyses by MOTIFS, PFAM, PRINTS, and BLOCKS indicate that the regions of SPARC-2 from F114 to C158 and from I248 to C292 are similar to a thyroglobulin type-1 repeat signature; the region from M335 to V434 is similar to an osteonectin domain; the regions from D372 to M384 and D409 to L421 are similar to an EF-hand calcium binding domain; the region from C47 to C87 is similar to a Kazal-type serine protease inhibitor domain; and the regions from C129 to S147 and from Q232 to L280 are similar to a type III EGF-like signature. As shown in FIGS. 3A, 3B, and 3C, SPARC-2 has chemical and structural similarity with a mouse SPARC-related protein (g5305327; SEQ ID NO:41). In particular, SPARC-2 and the mouse SPARC-related protein share 96% identity and share the SPARC-related domains. An antibody which specifically binds SPARC-2 is useful in assays to diagnose brain and prostate tumors, Huntington's disease, and multiple sclerosis. Exemplary portions of SEQ ID NO:2 are an antigenic epitope, residue V162 to residue D192 of SEQ ID NO:2 identified using the PROTEAN program (DNASTAR); and a biologically active portion, the conserved osteonectin domain, residue M335 to residue V434 of SEQ ID NO:2.

Mammalian variants of the cDNAs encoding SPARC-1 and SPARC-2 were identified using BLAST2 with default parameters and the ZOOSEQ databases (Incyte Genomics). These preferred variants have from about 83% to about 100% identity to SEQ ID NO:3 or SEQ ID NO:20 as shown in the table below. The first column shows the SEQ ID for the human cDNA; the second column, the SEQ IDvar for variant cDNAs; the third column, the Incyte clone number for the variant cDNAs; the fourth column, the library name; the fifth column, the percent identity to the human cDNA; and the sixth column, the alignment of the variant cDNA to the human cDNA.

| SEQ ID$_H$ | SEQ ID$_{var}$ | Clone$_{Var}$ | Library Name | Nt$_H$ Alignment | Identity |
|---|---|---|---|---|---|
| 3 | 14 | 702245306H1 | CNLUNOT01 | 1232–1295 | 89% |
| 3 | 15 | 702570096T2 | RASDNON01 | 1021–1377 | 83% |
| 3 | 16 | 701234138H1 | RASJNON03 | 1159–1362 | 85% |
| 3 | 17 | 700888003H1 | RAVANOT01 | 847–998 | 89% |
| 3 | 18 | 700268254H1 | RAADNOT03 | 201–316 | 89% |
| 3 | 19 | 700271122H1 | RAADNOT03 | 1217–1273 | 89% |
| 20 | 31 | 702768776H1 | CNLINOT01 | 1448–1924 | 87% |
| 20 | 32 | 700271122H1 | RAADNOT03 | 1148–1434 | 91% |
| 20 | 33 | 701648524H1 | RALITXT40 | 1516–1726 | 87% |
| 20 | 34 | 700306729H1 | RALINOT01 | 1423–1683 | 84% |
| 20 | 35 | 700594568H1 | RATRNOT04 | 1316–1439 | 92% |
| 20 | 36 | 701886717H1 | RALITXS02 | 1778–1861, 3526–3557 | 94%, 100% |
| 20 | 37 | 700694069H1 | RAADNON01 | 1778–1861, 1619–1734 | 90%, 85% |
| 20 | 38 | 700139225H1 | RALINOT01 | 1202–1244 | 100% |
| 20 | 39 | 700888003H1 | RAVANOT01 | 923–984 | 91% |
| 20 | 40 | 701234138H1 | RASJNON03 | 1208–1251 | 95% |

These cDNAs are particularly useful for producing transgenic cell lines or organisms which model human disorders and upon which potential therapeutic treatments for such disorders may be tested.

It will be appreciated by those skilled in the art that as a result of the degeneracy of the genetic code, a multitude of cDNAs encoding SPARC-1 and SPARC-2, some bearing minimal similarity to the cDNAs of any known and naturally occurring gene, may be produced. Thus, the invention contemplates each and every possible variation of cDNA that could be made by selecting combinations based on possible codon choices. These combinations are made in accordance with the standard triplet genetic code as applied to the polynucleotides encoding naturally occurring SPARC-1 and SPARC-2, and all such variations are to be considered as being specifically disclosed.

The cDNAs and fragments thereof (SEQ ID NOs:3–40) may be used in hybridization, amplification, and screening technologies to identify and distinguish among SEQ ID NOs:3 and 20 and related molecules in a sample. The mammalian cDNAs may be used to produce transgenic cell lines or organisms which are model systems for human atherosclerosis and cell proliferative disorders and upon which the toxicity and efficacy of potential therapeutic treatments may be tested. Toxicology studies, clinical trials, and subject/patient treatment profiles may be performed and monitored using the cDNAs, proteins, antibodies and molecules and compounds identified using the cDNAs and proteins of the present invention.

Characterization and Use of the Invention cDNA Libraries

In a particular embodiment disclosed herein, mRNA was isolated from mammalian cells and tissues using methods which are well known to those skilled in the art and used to prepare the cDNA libraries. The Incyte clones listed above were isolated from mammalian cDNA libraries. Three library preparations representative of the invention are described in the EXAMPLES below. The consensus sequences were chemically and/or electronically assembled from fragments including Incyte clones and extension and/or shotgun sequences using computer programs such as PHRAP (P Green, University of Washington, Seattle Wash.), and AUTOASSEMBLER application (Applied Biosystems, Foster City Calif.). Clones, extension and/or shotgun sequences are electronically assembled into clusters and/or master clusters.

Sequencing

Methods for sequencing nucleic acids are well known in the art and may be used to practice any of the embodiments of the invention. These methods employ enzymes such as the Klenow fragment of DNA polymerase I, SEQUENASE, Taq DNA polymerase and thermostable T7 DNA polymerase (Amersham Pharmacia Biotech (APB), Piscataway N.J.), or combinations of polymerases and proofreading exonucleases such as those found in the ELONGASE amplification system (Life Technologies, Gaithersburg Md.). Preferably, sequence preparation is automated with machines such MICROLAB 2200 system (Hamilton, Reno Nev.) and the DNA ENGINE thermal cycler (MJ Research, Watertown Mass.). Machines commonly used for sequencing include the ABI PRISM 3700, 377 or 373 DNA sequencing systems (PE Biosystems), the MEGABACE 1000 DNA sequencing system (APB), and the like. The sequences may be analyzed using a variety of algorithms well known in the art and described in Ausubel et al. (1997; *Short Protocols in Molecular Biology*, John Wiley & Sons, New York N.Y., unit 7.7) and in Meyers (1995; *Molecular Biology and Biotechnology*, Wiley VCH, New York N.Y., pp. 856–853).

Shotgun sequencing may also be used to complete the sequence of a particular cloned insert of interest. Shotgun strategy involves randomly breaking the original insert into segments of various sizes and cloning these fragments into vectors. The fragments are sequenced and reassembled using overlapping ends until the entire sequence of the original insert is known. Shotgun sequencing methods are well known in the art and use thermostable DNA polymerases, heat-labile DNA polymerases, and primers chosen from representative regions flanking the cDNAs of interest. Incomplete assembled sequences are inspected for identity using various algorithms or programs such as CONSED (Gordon (1998) Genome Res 8:195–202) which are well known in the art. Contaminating sequences including vector or chimeric sequences or deleted sequences can be removed or restored, respectively, organizing the incomplete assembled sequences into finished sequences.

Extension of a Nucleic Acid Sequence

The sequences of the invention may be extended using various PCR-based methods known in the art. For example, the XL-PCR kit (PE Biosystems), nested primers, and commercially available cDNA or genomic DNA libraries may be used to extend the nucleic acid sequence. For all PCR-based methods, primers may be designed using commercially available software, such as OLIGO 4.06 primer analysis software (National Biosciences, Plymouth Minn.) to be about 22 to 30 nucleotides in length, to have a GC content of about 50% or more, and to anneal to a target molecule at temperatures from about 55 C. to about 68 C. When extending a sequence to recover regulatory elements, it is preferable to use genomic, rather than cDNA libraries.

Hybridization

The cDNA and fragments thereof can be used in hybridization technologies for various purposes. A probe may be designed or derived from unique regions such as the 5' regulatory region or from a nonconserved region (i.e., 5' or 3' of the nucleotides encoding the conserved catalytic domain of the protein) and used in protocols to identify naturally occurring molecules encoding the SPARC-1 and SPARC-2, allelic variants, or related molecules. The probe may be DNA or RNA, may be single stranded and should have at least 50% sequence identity to any of the nucleic acid sequences, SEQ ID NOs:3–40. Hybridization probes may be produced using oligolabeling, nick translation, end-labeling, or PCR amplification in the presence of a reporter molecule. A vector containing the cDNA or a fragment thereof may be used to produce an mRNA probe in vitro by addition of an RNA polymerase and labeled nucleotides. These procedures may be conducted using commercially available kits such as those provided by APB.

The stringency of hybridization is determined by G+C content of the probe, salt concentration, and temperature. In particular, stringency can be increased by reducing the concentration of salt or raising the hybridization temperature. In solutions used for some membrane based hybridizations, addition of an organic solvent such as formamide allows the reaction to occur at a lower temperature. Hybridization can be performed at low stringency with buffers, such as 5×SSC with 1% sodium dodecyl sulfate (SDS) at 60 C., which permits the formation of a hybridization complex between nucleic acid sequences that contain some mismatches. Subsequent washes are performed at higher stringency with buffers such as 0.2×SSC with 0.1% SDS at either 45 C. (medium stringency) or 68 C. (high stringency). At high stringency, hybridization complexes will remain stable only where the nucleic acids are completely complementary. In some membrane-based hybridizations, preferably 35% or most preferably 50%, formamide can be added to the hybridization solution to reduce the temperature at which hybridization is performed, and background signals can be reduced by the use of other detergents such as Sarkosyl or TRITON X-100 (Sigma-Aldrich, St. Louis Mo.) and a blocking agent such as denatured salmon sperm DNA. Selection of components and conditions for hybridization are well known to those skilled in the art and are reviewed in Ausubel (supra) and Sambrook et al. (1989) *Molecular Cloning, A Laboratory Manual*, Cold Spring Harbor Press, Plainview N.Y.

Arrays may be prepared and analyzed using methods known in the art. Oligonucleotides may be used as either probes or targets in an array. The array can be used to monitor the expression level of large numbers of genes simultaneously and to identify genetic variants, mutations, and single nucleotide polymorphisms. Such information may be used to determine gene function; to understand the genetic basis of a condition, disease, or disorder; to diagnose a condition, disease, or disorder; and to develop and monitor the activities of therapeutic agents. (See, e.g., Brennan et al. (1995) U.S. Pat. No. 5,474,796; Schena et al. (1996) Proc Natl Acad Sci 93:10614–10619; Baldeschweiler et al. (1995) PCT application WO95/251116; Shalon et al. (1995) PCT application WO95/35505; Heller et al. (1997) Proc Natl Acad Sci 94:2150–2155; and Heller et al. (1997) U.S. Pat. No. 5,605,662.)

Hybridization probes are also useful in mapping the naturally occurring genomic sequence. The probes may be hybridized to: 1) a particular chromosome, 2) a specific region of a chromosome, or 3) an artificial chromosome construction such as human artificial chromosome (HAC), yeast artificial chromosome (YAC), bacterial artificial chromosome (BAC), bacterial P1 construction, or single chromosome cDNA libraries.

Expression

Any one of a multitude of cDNAs encoding SPARC-1 or SPARC-2 may be cloned into a vector and used to express the proteins, or portions thereof, in host cells. The nucleic acid sequence can be engineered by such methods as DNA shuffling (U.S. Pat. No. 5,830,721) and site-directed mutagenesis to create new restriction sites, alter glycosylation patterns, change codon preference to increase expression in a particular host, produce splice variants, extend half-life, and the like. The expression vector may contain transcriptional and translational control elements (promoters, enhancers, specific initiation signals, and polyadenylated 3' sequence) from various sources which have been selected for their efficiency in a particular host. The vector, cDNA, and regulatory elements are combined using in vitro recombinant DNA techniques, synthetic techniques, and/or in vivo genetic recombination techniques well known in the art and described in Sambrook (supra, ch. 4, 8, 16 and 17).

A variety of host systems may be transformed with an expression vector. These include, but are not limited to, bacteria transformed with recombinant bacteriophage, plasmid, or cosmid DNA expression vectors; yeast transformed with yeast expression vectors; insect cell systems transformed with baculovirus expression vectors; plant cell systems transformed with expression vectors containing viral and/or bacterial elements, or animal cell systems (Ausubel supra, unit 16). For example, an adenovirus transcription/translation complex may be utilized in mammalian cells. After sequences are ligated into the E1 or E3 region of the viral genome, the infective virus is used to transform and express the protein in host cells. The Rous sarcoma virus enhancer or SV40 or EBV-based vectors may also be used for high-level protein expression.

Routine cloning, subcloning, and propagation of nucleic acid sequences can be achieved using the multifunctional PBLUESCRIPT vector (Stratagene, La Jolla Calif.) or PSPORT1 plasmid (Life Technologies). Introduction of a nucleic acid sequence into the multiple cloning site of these vectors disrupts the lacZ gene and allows colorimetric screening for transformed bacteria. In addition, these vectors may be useful for in vitro transcription, dideoxy sequencing, single strand rescue with helper phage, and creation of nested deletions in the cloned sequence.

For long term production of recombinant proteins, the vector can be stably transformed into cell lines along with a selectable or visible marker gene on the same or on a separate vector. After transformation, cells are allowed to grow for about 1 to 2 days in enriched media and then are transferred to selective media. Selectable markers, antimetabolite, antibiotic, or herbicide resistance genes, confer resistance to the relevant selective agent and allow growth and recovery of cells which successfully express the introduced sequences. Resistant clones identified either by survival on selective media or by the expression of visible markers, such as anthocyanins, green fluorescent protein (GFP), β glucuronidase, luciferase and the like, may be propagated using culture techniques. Visible markers are also used to quantify the amount of protein expressed by the introduced genes. Verification that the host cell contains the desired mammalian cDNA is based on DNA-DNA or DNA-RNA hybridizations or PCR amplification techniques.

The host cell may be chosen for its ability to modify a recombinant protein in a desired fashion. Such modifications include acetylation, carboxylation, glycosylation, phosphorylation, lipidation, acylation and the like. Post-translational processing which cleaves a "prepro" form may also be used to specify protein targeting, folding, and/or activity. Different host cells available from the ATCC (Manassas Va.) which have specific cellular machinery and characteristic mechanisms for post-translational activities may be chosen to ensure the correct modification and processing of the recombinant protein.

Recovery of Proteins from Cell Culture

Heterologous moieties engineered into a vector for ease of purification include glutathione S-transferase (GST), 6×His, FLAG, MYC, and the like. GST and 6-His are purified using commercially available affinity matrices such as immobilized glutathione and metal-chelate resins, respectively. FLAG and MYC are purified using commercially available monoclonal and polyclonal antibodies. For ease of separation following purification, a sequence encoding a proteolytic cleavage site may be part of the vector located between the protein and the heterologous moiety. Methods for recombinant protein expression and purification are discussed in Ausubel (supra, unit 16) and are commercially available.

Chemical Synthesis of Peptides

Proteins or portions thereof may be produced not only by recombinant methods, but also by using chemical methods well known in the art. Solid phase peptide synthesis may be carried out in a batchwise or continuous flow process which sequentially adds α-amino- and side chain-protected amino acid residues to an insoluble polymeric support via a linker group. A linker group such as methylamine-derivatized polyethylene glycol is attached to poly(styrene-co-divinylbenzene) to form the support resin. The amino acid residues are N-α-protected by acid labile Boc (t-butyloxycarbonyl) or base-labile Fmoc (9-fluorenylmethoxycarbonyl). The carboxyl group of the protected amino acid is coupled to the amine of the linker group to anchor the residue to the solid phase support resin. Trifluoroacetic acid or piperidine are used to remove the protecting group in the case of Boc or Fmoc, respectively. Each additional amino acid is added to the anchored residue using a coupling agent or pre-activated amino acid derivative, and the resin is washed. The full length peptide is synthesized by sequential deprotection, coupling of derivitized amino acids, and washing with dichloromethane and/or N, N-dimethylformamide. The peptide is cleaved between the peptide carboxy terminus and the linker group to yield a peptide acid or amide. (Novabiochem 1997/98 Catalog and Peptide Synthesis Handbook, San Diego Calif. pp. S1–S20). Automated synthesis may also be carried out on machines such as the ABI 431A peptide synthesizer (Applied Biosystems). A protein or portion thereof may be substantially purified by preparative high performance liquid chromatography and its composition confirmed by amino acid analysis or by sequencing (Creighton (1984) *Proteins, Structures and Molecular Properties,* W H Freeman, New York N.Y.).

Preparation and Screening of Antibodies

Various hosts including goats, rabbits, rats, mice, humans, and others may be immunized by injection with SPARC-1 or SPARC-2 or any portions thereof. Adjuvants such as Freund's, mineral gels, and surface active substances such as lysolecithin, pluronic polyols, polyanions, peptides, oil emulsions, keyhole limpet hemacyanin (KLH), and dinitrophenol may be used to increase immunological response. The oligopeptide, peptide, or portion of protein used to induce antibodies should consist of at least about five amino acids, more preferably ten amino acids, which are identical to a portion of the natural protein. Oligopeptides may be fused with proteins such as KLH in order to produce antibodies to the chimeric molecule.

Monoclonal antibodies may be prepared using any technique which provides for the production of antibodies by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol Methods 81:3142; Cote et al. (1983) Proc Natl Acad Sci 80:2026–2030; and Cole et al. (1984) Mol Cell Biol 62:109–120.)

Alternatively, techniques described for the production of single chain antibodies may be adapted, using methods known in the art, to produce epitope specific single chain antibodies. Antibody fragments which contain specific binding sites for epitopes of the protein may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 246:1275–1281.)

The SPARC-1 or SPARC-2 or portions thereof may be used in screening assays of phagemid or B-lymphocyte immunoglobulin libraries to identify antibodies having the desired specificity. Numerous protocols for competitive binding or immunoassays using either polyclonal or monoclonal antibodies with established specificities are well known in the art. Such immunoassays typically involve the measurement of complex formation between the protein and its specific antibody. A two-site, monoclonal-based immunoassay utilizing monoclonal antibodies reactive to two non-interfering epitopes is preferred, but a competitive binding assay may also be employed (Pound (1998) *Immunochemical Protocols,* Humana Press, Totowa N.J.).

Labeling of Molecules for Assay

A wide variety of reporter molecules and conjugation techniques are known by those skilled in the art and may be used in various nucleic acid, amino acid, and antibody assays. Synthesis of labeled molecules may be achieved using commercially available kits (Promega, Madison Wis.) for incorporation of a labeled nucleotide such as $^{32}$P-dCTP (APB), Cy3-dCTP or Cy5-dCTP (Operon Technologies, Alameda Calif.), or amino acid such as $^{35}$S-methionine (APB). Nucleotides and amino acids may be directly labeled with a variety of substances including fluorescent, chemiluminescent, or chromogenic agents, and the like, by chemical conjugation to amines, thiols and other groups present in the molecules using reagents such as BIODIPY or FITC (Molecular Probes, Eugene Oreg.).

Diagnostics

The cDNAs, fragments, oligonucleotides, complementary RNA and DNA molecules, and PNAs and may be used to detect and quantify differential gene expression, absence/presence vs. excess, expression of mRNAs or to monitor mRNA levels during therapeutic intervention. Similarly antibodies which specifically bind SPARC-1 or SPARC-2 may be used to quantitate the protein. Disorders associated with differential expression include atherosclerosis and cell proliferative disorders, particularly anaplastic oligodendroglioma, astrocytoma, oligoastrocytoma, glioblastoma, meningioma, ganglioneuroma, neuronal neoplasm, multiple sclerosis, Huntington's disease, breast adenocarcinoma, prostate adenocarcinoma, stomach adenocarcinoma, metastasizing neuroendocrine carcinoma, nonproliferative fibrocystic and proliferative fibrocystic breast disease, gallbladder cholecystitis and cholelithiasis, osteoarthritis, and rheumatoid arthritis. Upregulation of SPARC-1 is associated with adenocarcinoma in stomach, breast, and prostate tissues, nonproliferative fibrocystic and proliferative fibrocystic breast disease, brain and neuroganglion tumors, osteoarthritis, rheumatoid arthritis, cholecystitis and cholelithiasis. Upregulation of SPARC-2 is associated with brain tumors, prostate tumors, Huntington's disease, and multiple sclerosis. Downregulation of SPARC-2 is associated with metastasizing neuroendocrine carcinomas. The diagnostic assay may use hybridization or amplification technology to compare gene expression in a biological sample from a patient to standard samples in order to detect differential gene expression. Qualitative or quantitative methods for this comparison are well known in the art.

For example, the cDNA or probe may be labeled by standard methods and added to a biological sample from a patient under conditions for the formation of hybridization complexes. After an incubation period, the sample is washed and the amount of label (or signal) associated with hybridization complexes, is quantified and compared with a standard value. If complex formation in the patient sample is significantly altered (higher or lower) in comparison to either a normal or disease standard, then differential expression indicates the presence of a disorder.

In order to provide standards for establishing differential expression, normal and disease expression profiles are established. This is accomplished by combining a sample taken from normal subjects, either animal or human, with a cDNA under conditions for hybridization to occur. Standard hybridization complexes may be quantified by comparing the values obtained using normal subjects with values from an experiment in which a known amount of a substantially purified sequence is used. Standard values obtained in this manner may be compared with values obtained from samples from patients who were diagnosed with a particular condition, disease, or disorder. Deviation from standard values toward those associated with a particular disorder is used to diagnose that disorder.

Such assays may also be used to evaluate the efficacy of a particular therapeutic treatment regimen in animal studies and in clinical trial or to monitor the treatment of an individual patient. Once the presence of a condition is established and a treatment protocol is initiated, diagnostic assays may be repeated on a regular basis to determine if the level of expression in the patient begins to approximate that which is observed in a normal subject. The results obtained from successive assays may be used to show the efficacy of treatment over a period ranging from several days to months.

Immunological Methods

Detection and quantification of a protein using either specific polyclonal or monoclonal antibodies are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes is preferred, but a competitive binding assay may be employed. (See, e.g., Coligan et al. (1997) *Current Protocols in Immunology*, Wiley-Interscience, New York N.Y.; and Pound, supra).

Therapeutics

Chemical and structural similarities, in the context of the osteonectin, thyroglobulin type-1, EF-hand, Kazal-type serine protease inhibitor, and EGF domains, exist between regions of SPARC-1 (SEQ ID NO:1), SPARC-2 (SEQ ID NO:2) and the mouse SPARC-related protein (g5305327; SEQ ID NO:41) shown in FIG. 3. Differential expression of SPARC-1 is associated with gastrointestinal, breast, prostate, musculoskeletal system, and nervous system tissues and with cell proliferative disorders as shown in Tables 1A and 1B. SPARC-1 clearly plays a role in adenocarcinoma in stomach, breast, and prostate tissues, fibrocystic breast disease, brain and neuroganglion tumors, osteoarthritis and rheumatoid arthritis, and cholecystitis and cholelithiasis. Differential expression of SPARC-2 is associated with female and male reproductive tissues, liver, and the nervous system and with cell proliferative disorders as shown in Tables 2A and 2B. SPARC-2 clearly plays a role in brain tumors, prostate tumors, metastasizing neuroendocrine carcinoma, and neurological diseases such as Huntington's and multiple sclerosis.

In the treatment of conditions associated with increased expression of the SPARC-1 or SPARC-2, it is desirable to decrease expression or protein activity. In one embodiment, the an inhibitor, antagonist or antibody of the protein may be administered to a subject to treat a condition associated with increased expression or activity. In another embodiment, a pharmaceutical composition comprising an inhibitor, antagonist or antibody in conjunction with a pharmaceutical carrier may be administered to a subject to treat a condition associated with the increased expression or activity of the endogenous protein. In an additional embodiment, a vector expressing the complement of the cDNA or fragments thereof may be administered to a subject to treat the disorder.

In the treatment of conditions associated with decreased expression of the SPARC-2 such as metastasizing neuroendocrine carcinoma, it is desirable to increase expression or protein activity. In one embodiment, the protein, an agonist or enhancer may be administered to a subject to treat a condition associated with decreased expression or activity. In another embodiment, a pharmaceutical composition comprising the protein, an agonist or enhancer in conjunction with a pharmaceutical carrier may be administered to a subject to treat a condition associated with the decreased expression or activity of the endogenous protein. In an additional embodiment, a vector expressing cDNA may be administered to a subject to treat the disorder.

Any of the cDNAs, complementary molecules, or fragments thereof, proteins or portions thereof, vectors delivering these nucleic acid molecules or expressing the proteins, and their ligands may be administered in combination with other therapeutic agents. Selection of the agents for use in combination therapy may be made by one of ordinary skill in the art according to conventional pharmaceutical principles. A combination of therapeutic agents may act synergistically to affect treatment of a particular disorder at a lower dosage of each agent.

Modification of Gene Expression Using Nucleic Acids

Gene expression may be modified by designing complementary or antisense molecules (DNA, RNA, or PNA) to the control, 5', 3', or other regulatory regions of the genes encoding SPARC-1 and SPARC-2. Oligonucleotides designed with reference to the transcription initiation site are preferred. Similarly, inhibition can be achieved using triple helix base-pairing which inhibits the binding of polymerases, transcription factors, or regulatory molecules (Gee et al. In: Huber and Carr (1994) *Molecular and Immunologic Approaches*, Futura Publishing, Mt. Kisco N.Y., pp. 163–177). A complementary molecule may also be designed to block translation by preventing binding between ribosomes and mRNA. In one alternative, a library or plurality of cDNAs or fragments thereof may be screened to identify those which specifically bind a regulatory, nontranslated sequence.

Ribozymes, enzymatic RNA molecules, may also be used to catalyze the specific cleavage of RNA. The mechanism of ribozyme action involves sequence-specific hybridization of the ribozyme molecule to complementary target RNA followed by endonucleolytic cleavage at sites such as GUA, GUU, and GUC. Once such sites are identified, an oligonucleotide with the same sequence may be evaluated for secondary structural features which would render the oligonucleotide inoperable. The suitability of candidate targets may also be evaluated by testing their hybridization with complementary oligonucleotides using ribonuclease protection assays.

Complementary nucleic acids and ribozymes of the invention may be prepared via recombinant expression, in vitro or in vivo, or using solid phase phosphoramidite chemical synthesis. In addition, RNA molecules may be modified to increase intracellular stability and half-life by addition of flanking sequences at the 5' and/or 3' ends of the molecule or by the use of phosphorothioate or 2' O-methyl rather than phosphodiesterase linkages within the backbone of the molecule. Modification is inherent in the production of PNAs and can be extended to other nucleic acid molecules. Either the inclusion of nontraditional bases such as inosine, queosine, and wybutosine, and or the modification of adenine, cytidine, guanine, thymine, and uridine with acetyl-, methyl-, thio- groups renders the molecule less available to endogenous endonucleases.

Screening and Purification Assays

The cDNAs encoding SPARC-1 and SPARC-2 may be used to screen a library of molecules or compounds for specific binding affinity. The libraries may be aptamers, DNA molecules, RNA molecules, PNAs, peptides, proteins such as transcription factors, enhancers, repressors, and other ligands which regulate the activity, replication, transcription, or translation of the cDNA in the biological system. The assay involves combining the cDNA or a fragment thereof with the library of molecules under conditions allowing specific binding, and detecting specific binding to identify at least one molecule which specifically binds the single stranded or, if appropriate, double stranded molecule.

In one embodiment, the cDNA of the invention may be incubated with a plurality of purified molecules or compounds and binding activity determined by methods well known in the art, e.g., a gel-retardation assay (U.S. Pat. No. 6,010,849) or a reticulocyte lysate transcriptional assay. In another embodiment, the cDNA may be incubated with nuclear extracts from biopsied and/or cultured cells and tissues. Specific binding between the cDNA and a molecule or compound in the nuclear extract is initially determined by gel shift assay and may be later confirmed by recovering and raising antibodies against that molecule or compound. When these antibodies are added into the assay, they cause a supershift in the gel-retardation assay.

In another embodiment, the cDNA may be used to purify a molecule or compound using affinity chromatography methods well known in the art. In one embodiment, the cDNA is chemically reacted with cyanogen bromide groups on a polymeric resin or gel. Then a sample is passed over and reacts with or binds to the cDNA. The molecule or compound which is bound to the cDNA may be released from the cDNA by increasing the salt concentration of the flow-through medium and collected.

In a further embodiment,, the protein or a portion thereof may be used to purify a ligand from a sample. A method for using a mammalian protein or a portion thereof to purify a ligand would involve combining the protein or a portion thereof with a sample under conditions to allow specific binding, detecting specific binding between the protein and ligand, recovering the bound protein, and using an appropriate chaotropic agent to separate the protein from the purified ligand.

In a preferred embodiment, SPARC-1 and SPARC-2 or portions thereof may be used to screen a plurality of molecules or compounds in any of a variety of screening assays. The portion of the protein employed in such screening may be free in solution, affixed to an abiotic or biotic substrate (e.g. borne on a cell surface), or located intracellularly. For example, in one method, viable or fixed prokaryotic host cells that are stably transformed with recombinant nucleic acids that have expressed and positioned a peptide on their cell surface can be used in screening assays. The cells are screened against a plurality or libraries of ligands and the specificity of binding or formation of complexes between the expressed protein and the ligand may be measured. Specific binding between the protein and molecule may be measured. Depending on the kind of library being screened, the assay may be used to identify DNA molecules, RNA molecules, peptide nucleic acids, peptides, proteins, mimetics, agonists, antagonists, antibodies, immunoglobulins, inhibitors, and drugs or any other ligand, which specifically binds the protein.

In one aspect, this invention comtemplates a method for high throughput screening using very small assay volumes and very small amounts of test compound as described in U.S. Pat. No. 5,876,946, incorporated herein by reference. This method is used to screen large numbers of molecules and compounds via specific binding. In another aspect, this invention also contemplates the use of competitive drug screening assays in which neutralizing antibodies capable of binding the protein specifically compete with a test compound capable of binding to the protein or oligopeptide or portion thereof. Molecules or compounds identified by screening may be used in a mammalian model system to evaluate their toxicity, diagnostic, or therapeutic potential.

Pharmacology

Pharmaceutical compositions are those substances wherein the active ingredients are contained in an effective amount to achieve a desired and intended purpose. The determination of an effective dose is well within the capability of those skilled in the art. For any compound, the therapeutically effective dose may be estimated initially either in cell culture assays or in animal models. The animal model is also used to achieve a desirable concentration range and route of administration. Such information may then be used to determine useful doses and routes for administration in humans.

A therapeutically effective dose refers to that amount of protein or inhibitor which ameliorates the symptoms or condition. Therapeutic efficacy and toxicity of such agents may be determined by standard pharmaceutical procedures in cell cultures or experimental animals, e.g., $ED_{50}$ (the dose therapeutically effective in 50% of the population) and $LD_{50}$. (the dose lethal to 50% of the population). The dose ratio between toxic and therapeutic effects is the therapeutic index, and it may be expressed as the ratio, $LD_{50}/ED_{50}$. Pharmaceutical compositions which exhibit large therapeutic indexes are preferred. The data obtained from cell culture assays and animal studies are used in formulating a range of dosage for human use.

Model Systems

Animal models may be used as bioassays where they exhibit a phenotypic response similar to that of humans and where exposure conditions are relevant to human exposures. Mammals are the most common models, and most infectious agent, cancer, drug, and toxicity studies are performed on rodents such as rats or mice because of low cost, availability, lifespan, reproductive potential, and abundant reference literature. Inbred and outbred rodent strains provide a convenient model for investigation of the physiological consequences of under- or over-expression of genes of interest and for the development of methods for diagnosis and treatment of diseases. A mammal inbred to over-express a particular gene (for example, secreted in milk) may also serve as a convenient source of the protein expressed by that gene.

Toxicology

Toxicology is the study of the effects of agents on living systems. The majority of toxicity studies are performed on rats or mice. Observation of qualitative and quantitative changes in physiology, behavior, homeostatic processes, and lethality in the rats or mice are used to generate a toxicity profile and to assess potential consequences on human health following exposure to the agent.

Genetic toxicology identifies and analyzes the effect of an agent on the rate of endogenous, spontaneous, and induced genetic mutations. Genotoxic agents usually have common chemical or physical properties that facilitate interaction with nucleic acids and are most harmful when chromosomal aberrations are transmitted to progeny. Toxicological studies may identify agents that increase the frequency of structural or functional abnormalities in the tissues of the progeny if administered to either parent before conception, to the mother during pregnancy, or to the developing organism. Mice and rats are most frequently used in these tests because their short reproductive cycle allows the production of the numbers of organisms needed to satisfy statistical requirements.

Acute toxicity tests are based on a single administration of an agent to the subject to determine the symptomology or lethality of the agent. Three experiments are conducted: 1) an initial dose-range-finding experiment, 2) an experiment to narrow the range of effective doses, and 3) a final experiment for establishing the dose-response curve.

Subchronic toxicity tests are based on the repeated administration of an agent. Rat and dog are commonly used in these studies to provide data from species in different families. With the exception of carcinogenesis, there is considerable evidence that daily administration of an agent at high-dose concentrations for periods of three to four months will reveal most forms of toxicity in adult animals.

Chronic toxicity tests, with a duration of a year or more, are used to demonstrate either the absence of toxicity or the carcinogenic potential of an agent. When studies are conducted on rats, a minimum of three test groups plus one control group are used, and animals are examined and monitored at the outset and at intervals throughout the experiment.

Transgenic Animal Models

Transgenic rodents that over-express or under-express a gene of interest may be inbred and used to model human diseases or to test therapeutic or toxic agents. (See, e.g., U.S. Pat. Nos. 5,175,383 and 5,767,337.) In some cases, the introduced gene may be activated at a specific time in a specific tissue type during fetal or postnatal development. Expression of the transgene is monitored by analysis of phenotype, of tissue-specific mRNA expression, or of serum and tissue protein levels in transgenic animals before, during, and after challenge with experimental drug therapies.

Embryonic Stem Cells

Embryonic (ES) stem cells isolated from rodent embryos retain the potential to form embryonic tissues. When ES cells are placed inside a carrier embryo, they resume normal development and contribute to tissues of the live-born animal. ES cells are the preferred cells used in the creation of experimental knockout and knockin rodent strains. Mouse ES cells, such as the mouse 129/SvJ cell line, are derived from the early mouse embryo and are grown under culture conditions well known in the art. Vectors used to produce a transgenic strain contain a disease gene candidate and a marker gen, the latter serves to identify the presence of the introduced disease gene. The vector is transformed into ES cells by methods well known in the art, and transformed ES cells are identified and microinjected into mouse cell blastocysts such as those from the C57BL/6 mouse strain. The blastocysts are surgically transferred to pseudopregnant dams, and the resulting chimeric progeny are genotyped and bred to produce heterozygous or homozygous strains.

ES cells derived from human blastocysts may be manipulated in vitro to differentiate into at least eight separate cell lineages. These lineages are used to study the differentiation of various cell types and tissues in vitro, and they include endoderm, mesoderm, and ectodermal cell types which differentiate into, for example, neural cells, hematopoietic lineages, and cardiomyocytes.

Knockout Analysis

In gene knockout analysis, a region of a mammalian gene is enzymatically modified to include a non-mammalian gene such as the neomycin phosphotransferase gene (neo; Capecchi (1989) Science 244:1288–1292). The modified gene is transformed into cultured ES cells and integrates into the endogenous genome by homologous recombination. The inserted sequence disrupts transcription and translation of the endogenous gene. Transformed cells are injected into rodent blastulae, and the blastulae are implanted into pseudopregnant dams. Transgenic progeny are crossbred to obtain homozygous inbred lines which lack a functional copy of the mammalian gene. In one example, the mammalian gene is a human gene.

Knockin Analysis

ES cells can be used to create knockin humanized animals (pigs) or transgenic animal models (mice or rats) of human diseases. With knockin technology, a region of a human gene is injected into animal ES cells, and the human sequence integrates into the animal cell genome. Transformed cells are injected into blastulae and the blastulae are implanted as described above. Transgenic progeny or inbred lines are studied and treated with potential pharmaceutical agents to obtain information on treatment of the analogous human condition. These methods have been used to model several human diseases.

Non-Human Primate Model

The field of animal testing deals with data and methodology from basic sciences such as physiology, genetics, chemistry, pharmacology and statistics. These data are paramount in evaluating the effects of therapeutic agents on non-human primates as they can be related to human health. Monkeys are used as human surrogates in vaccine and drug evaluations, and their responses are relevant to human exposures under similar conditions. Cynomolgus and Rhesus monkeys (*Macaca fascicularis* and *Macaca mulatta*, respectively) and Common Marmosets (*Callithrix jacchus*) are the most common non-human primates (NHPs) used in these investigations. Since great cost is associated with developing and maintaining a colony of NHPs, early research and toxicological studies are usually carried out in rodent models. In studies using behavioral measures such as drug addiction, NHPs are the first choice test animal. In addition, NHPs and individual humans exhibit differential sensitivities to many drugs and toxins and can be classified as a range of phenotypes from "extensive metabolizers" to "poor metabolizers" of these agents.

In additional embodiments, the cDNAs which encode the mammalian protein may be used in any molecular biology techniques that have yet to be developed, provided the new techniques rely on properties of cDNAs that are currently known, including, but not limited to, such properties as the triplet genetic code and specific base pair interactions.

EXAMPLES

The examples below are provided to illustrate the subject invention and are not included for the purpose of limiting the invention. For purposes of example, preparation of the human gallbladder (GBLANOT01) and normalized breast (BRSTNON2) libraries will be described.

I cDNA Library Construction

Gallbladder

The tissue used for the GBLANOT01 library was obtained from a diseased gallbladder removed from a 53-year-old Caucasian female during a cholecystectomy. Pathology indicated mild chronic cholecystitis and cholelithiasis. The frozen tissue was homogenized and lysed in TRIZOL reagent (1 g tissue/10 ml; Life Technologies) using a POLYTRON homogenizer (PT-3000; (Brinkmann Instruments, Westbury N.J.). After brief incubation on ice, chloroform was added (1:5 v/v), and the mixture was centrifuged to separate the phases. The upper aqueous phase was removed to a fresh tube, and isopropanol was added to precipitate RNA. The RNA was resuspended in RNase-free water and treated with DNase. The RNA was re-extracted with acid phenol-chloroform and reprecipitated with sodium acetate and ethanol. Poly(A+) RNA was isolated using the OLIGOTEX kit (Qiagen, Chatsworth Calif.).

Normalized Breast

About $1.2 \times 10^6$ independent clones of the pooled BRSTNOT34 and BRSTNOT35 plasmid libraries in *E. coli* strain DH12S competent cells (Life Technologies) were grown in liquid culture under carbenicillin (25 mg/l) and methicillin (1 mg/ml) selection following transformation by electroporation. To reduce the number of excess cDNA copies according to their abundance levels in the library, the cDNA library was normalized in two rounds according to the procedure of Soares et al. (1994; Proc Natl Acad Sci 91:9228–9232) and Bonaldo et al.(1996; Genome Research 6:791–806), with the following modifications. The primer to template ratio in the primer extension reaction was increased from 2:1 to 300:1. The reannealing hybridization was extended from 13 to 48 hr. The single stranded DNA circles of the normalized library were purified by hydroxyapatite chromatography and converted to partially double-stranded by random priming, ligated into pINCY plasmid and electroporated into DH12S competent cells (Life Technologies).

II Construction of pINCY Plasmid

The plasmid was constructed by digesting the pSPORT1 plasmid (Life Technologies) with EcoRI restriction enzyme (New England Biolabs, Beverly Mass.) and filling the overhanging ends using Klenow enzyme (New England Biolabs) and 2'-deoxynucleotide 5'-triphosphates (dNTPs). The plasmid was self-ligated and transformed into the bacterial host, E. coli strain JM109.

An intermediate plasmid produced by the bacteria (pSPORT 1-ΔRI) showed no digestion with EcoRI and was digested with Hind HI (New England Biolabs) and the overhanging ends were again filled in with Klenow and dNTPs. A linker sequence was phosphorylated, ligated onto the 5' blunt end, digested with EcoRI, and self-ligated. Following transformation into JM109 host cells, plasmids were isolated and tested for preferential digestibility with EcoRI, but not with Hind III. A single colony that met this criteria was designated pINCY plasmid.

After testing the plasmid for its ability to incorporate cDNAs from a library prepared using NotI and EcoRI restriction enzymes, several clones were sequenced; and a single clone containing an insert of approximately 0.8 kb was selected from which to prepare a large quantity of the plasmid. After digestion with NotI and EcoRI, the plasmid was isolated on an agarose gel and purified using a QIAQUICK column (Qiagen) for use in library construction.

III Isolation and Sequencing of cDNA Clones

Plasmid DNA was released from the cells and purified using either the MINIPREP kit (Edge Biosystems, Gaithersburg Md.) or the REAL PREP 96 plasmid kit (Qiagen). This kit consists of a 96-well block with reagents for 960 purifications. The recommended protocol was employed except for the following changes:1) the bacteria were cultured in 1 ml of sterile TERRIFIC BROTH (BD Biosciences, Sparks Md.) with carbenicillin at 25 mg/l and glycerol at 0.4%; 2) after inoculation, the cells were cultured for 19 hours and then lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4 C.

The cDNAs were prepared for sequencing using the MICROLAB 2200 system (Hamilton) in combination with the DNA ENGINE thermal cyclers (MJ Research). The cDNAs were sequenced by the method of Sanger and Coulson (1975; J Mol Biol 94:441–448) using an ABI PRISM 377 sequencing system (PE Biosystems) or the MEGABACE 1000 DNA sequencing system (APB). Most of the isolates were sequenced according to standard ABI protocols and kits (PE Biosystems) with solution volumes of 0.25×–1.0×concentrations. In the alternative, cDNAs were sequenced using solutions and dyes from APB.

IV Extension of cDNA Sequences

The cDNAs were extended using the cDNA clone and oligonucleotide primers. One primer was synthesized to initiate 5' extension of the known fragment, and the other, to initiate 3' extension of the known fragment. The initial primers were designed using OLIGO 4.06 software (National Biosciences), to be about 22 to 30 nucleotides in length, to have a GC content of about 50% or more, and to anneal to the target sequence at temperatures of about 68 C. to about 72 C. Any stretch of nucleotides that would result in hairpin structures and primer-primer dimerizations was avoided.

Selected cDNA libraries were used as templates to extend the sequence. If more than one extension was necessary, additional or nested sets of primers were designed. Preferred libraries have been size-selected to include larger cDNAs and random primed to contain more sequences with 5' or upstream regions of genes. Genomic libraries are used to obtain regulatory elements, especially extension into the 5' promoter binding region.

High fidelity amplification was obtained by PCR using methods such as that taught in U.S. Pat. No. 5,932,451. PCR was performed in 96-well plates using the DNA ENGINE thermal cycler (MJ Research). The reaction mix contained DNA template, 200 nmol of each primer, reaction buffer containing $Mg^{2+}$, $(NH_4)_2SO_4$, and β-mercaptoethanol, Taq DNA polymerase (APB), ELONGASE enzyme (Life Technologies), and Pfu DNA polymerase (Stratagene), with the following parameters for primer pair PCI A and PCI B (Incyte Genomics): Step 1: 94 C., three min; Step 2: 94 C., 15 sec; Step 3: 60 C., one min; Step 4: 68 C., two min; Step 5: Steps 2, 3, and 4 repeated 20 times; Step 6: 68C, five min; Step 7: storage at 4 C. In the alternative, the parameters for primer pair 17 and SK+ (Stratagene) were as follows: Step 1: 94 C., three min; Step 2: 94 C., 15 sec; Step 3: 57C., one min; Step 4: 68 C., two min; Step 5: Steps 2, 3, and 4 repeated 20 times; Step 6: 68 C., five min; Step 7: storage at 4 C.

The concentration of DNA in each well was determined by dispensing 100 μl PICOGREEN quantitation reagent (0.25% reagent in 1×TE, v/v; Molecular Probes) and 0.5 μl of undiluted PCR product into each well of an opaque fluorimeter plate (Corning, Acton Mass.) and allowing the DNA to bind to the reagent. The plate was scanned in a Fluoroskan II (Labsystems Oy) to measure the fluorescence of the sample and to quantify the concentration of DNA. A 5 μl to 10 μl aliquot of the reaction mixture was analyzed by electrophoresis on a 1% agarose mini-gel to determine which reactions were successful in extending the sequence.

The extended clones were desalted, concentrated, transferred to 384-well plates, digested with CviJI cholera virus endonuclease (Molecular Biology Research, Madison Wis.), and sonicated or sheared prior to religation into pUC18 vector (APB). For shotgun sequences, the digested nucleotide sequences were separated on low concentration (0.6 to 0.8%) agarose gels, fragments were excised, and the agar was digested with AGARACE enzyme (Promega). Extended clones were religated using T4 DNA ligase (New England Biolabs) into pUC 18 vector (APB), treated with Pfu DNA polymerase (Stratagene) to fill-in restriction site overhangs, and transfected into E. coli competent cells. Transformed cells were selected on antibiotic-containing media, and individual colonies were picked and cultured overnight at 37 C. in 384-well plates in LB/2×carbenicillin liquid media.

The cells were lysed, and DNA was amplified using primers, Taq DNA polymerase (APB) and Pfu DNA polymerase (Stratagene) with the following parameters: Step 1: 94 C., three min; Step 2: 94 C., 15 sec; Step 3: 60 C., one min; Step 4: 72 C., two min; Step 5: steps 2, 3, and 4 repeated 29 times; Step 6: 72 C., five min; Step 7: storage at 4 C. DNA was quantified using PICOGREEN quantitative reagent (Molecular Probes) as described above. Samples with low DNA recoveries were reamplified using the conditions described above. Samples were diluted with 20% dimethylsulfoxide (DMSO; 1:2, v/v), and sequenced using DYENAMIC energy transfer sequencing primers and the DYENAMIC DIRECT cycle sequencing kit (APB) or the ABI PRISM BIGDYE terminator cycle sequencing kit (PE Biosystems).

V Homology Searching of cDNA Clones and Their Deduced Proteins

The cDNAs of the Sequence Listing or their deduced amino acid sequences were used to query databases such as GenBank, SwissProt, BLOCKS, and the like. These databases that contain previously identified and annotated sequences or domains were searched using BLAST or BLAST 2 (Altschul et al. supra; Altschul, supra) to produce alignments and to determine which sequences were exact matches or homologs. The alignments were to sequences of prokaryotic (bacterial) or eukaryotic (animal, fungal, or plant) origin. Alternatively, algorithms such as the one described in Smith and Smith (1992, Protein Engineering 5:35–51) could have been used to deal with primary sequence patterns and secondary structure gap penalties. All of the sequences disclosed in this application have lengths of at least 49 nucleotides, and no more than 12% uncalled bases (where N is recorded rather than A, C, G, or T).

As detailed in Karlin (supra), BLAST matches between a query sequence and a database sequence were evaluated statistically and only reported when they satisfied the threshold of $10^{-25}$ for nucleotides and $10^{-14}$ for peptides. Homology was also evaluated by product score calculated as follows: the % nucleotide or amino acid identity [between the query and reference sequences] in BLAST is multiplied by the % maximum possible BLAST score [based on the lengths of query and reference sequences] and then divided by 100. In comparison with hybridization procedures used in the laboratory, the electronic stringency for an exact match was set at 70, and the conservative lower limit for an exact match was set at approximately 40 (with 1–2% error due to uncalled bases).

The BLAST software suite, freely available sequence comparison algorithms (NCBI, Bethesda Md.; http://www.ncbi.nlm.nih.gov/gorflbl2.html), includes various sequence analysis programs including "blastn" that is used to align nucleic acid molecules and BLAST 2 that is used for direct pairwise comparison of either nucleic or amino acid molecules. BLAST programs are commonly used with gap and other parameters set to default settings, e.g.: Matrix: BLOSUM62; Reward for match:1; Penalty for mismatch: –2; Open Gap: 5 and Extension Gap: 2 penalties; Gapxdropoff: 50; Expect:10; Word Size: 11; and Filter: on. Identity is measured over the entire length of a sequence or some smaller portion thereof. Brenner et al. (1998; Proc Natl Acad Sci 95:6073–6078, incorporated herein by reference) analyzed the BLAST for its ability to identify structural homologs by sequence identity and found 30% identity is a reliable threshold for sequence alignments of at least 150 residues and 40%, for alignments of at least 70 residues.

The mammalian cDNAs of this application were compared with assembled consensus sequences or templates found in the LIFESEQ GOLD database. Component sequences from cDNA, extension, full length, and shotgun sequencing projects were subjected to PHRED analysis and assigned a quality score. All sequences with an acceptable quality score were subjected to various pre-processing and editing pathways to remove low quality 3' ends, vector and linker sequences, polyA tails, Alu repeats, mitochondrial and ribosomal sequences, and bacterial contamination sequences. Edited sequences had to be at least 50 bp in length, and low-information sequences and repetitive elements such as dinucleotide repeats, Alu repeats, and the like, were replaced by "Ns" or masked.

Edited sequences were subjected to assembly procedures in which the sequences were assigned to gene bins. Each sequence could only belong to one bin, and sequences in each bin were assembled to produce a template. Newly sequenced components were added to existing bins using BLAST and CROSSMATCH. To be added to a bin, the component sequences had to have a BLAST quality score greater than or equal to 150 and an alignment of at least 82% local identity. The sequences in each bin were assembled using PHRAP. Bins with several overlapping component sequences were assembled using DEEP PHRAP. The orientation of each template was determined based on the number and orientation of its component sequences.

Bins were compared to one another and those having local similarity of at least 82% were combined and reassembled. Bins having templates with less than 95% local identity were split. Templates were subjected to analysis by STITCHER/EXON MAPPER algorithms that analyze the probabilities of the presence of splice variants, alternatively spliced exons, splice junctions, differential expression of alternative spliced genes across tissue types or disease states, and the like. Assembly procedures were repeated periodically, and templates were annotated using BLAST against GenBank databases such as GBpri. An exact match was defined as having from 95% local identity over 200 base pairs through 100% local identity over 100 base pairs and a homolog match as having an E-value (or probability score) of $\leq 1 \times 10^{-8}$. The templates were also subjected to frameshift FASTx against GENPEPT, and homolog match was defined as having an E-value of $\leq 1 \times 10^{-8}$. Template analysis and assembly was described in U.S. Ser. No. 09/276,534, filed Mar. 25, 1999.

Following assembly, templates were subjected to BLAST, motif, and other functional analyses and categorized in protein hierarchies using methods described in U.S. Ser. Nos. 08/812,290 and 08/811,758, both filed Mar. 6, 1997; in U.S. Ser. No. 08/947,845, filed Oct. 9, 1997; and in U.S. Ser. No. 09/034,807, filed Mar. 4, 1998. Then templates were analyzed by translating each template in all three forward reading frames and searching each translation against the PFAM database of hidden Markov model-based protein families and domains using the HMMER software package (Washington University School of Medicine, St. Louis Mo.).

The cDNA was further analyzed using MACDNASIS PRO software (Hitachi Software Engineering), and LASERGENE software (DNASTAR) and queried against public databases such as the GenBank rodent, mammalian, vertebrate, prokaryote, and eukaryote databases, SwissProt, BLOCKS, PRINTS, PFAM, and Prosite.

VI Chromosome Mapping

Radiation hybrid and genetic mapping data available from public resources such as the Stanford Human Genome Center (SHGC), Whitehead Institute for Genome Research (WIGR), and Généthon are used to determine if any of the cDNAs presented in the Sequence Listing have been mapped. Any of the fragments of the cDNAs encoding SPARC-1 and SPARC-2 that have been mapped result in the assignment of all related regulatory and coding sequences mapping to the same location. The genetic map locations are described as ranges, or intervals, of human chromosomes. The map position of an interval, in cM (which is roughly equivalent to 1 megabase of human DNA), is measured relative to the terminus of the chromosomal p-arm.

VII Hybridization Technologies and Analyses

Immobilization of cDNAs on a Substrate

The cDNAs are applied to a substrate by one of the following methods. A mixture of cDNAs is fractionated by gel electrophoresis and transferred to a nylon membrane by capillary transfer. Alternatively, the cDNAs are individually ligated to a vector and inserted into bacterial host cells to form a library. The cDNAs are then arranged on a substrate by one of the following methods. In the first method, bacterial cells containing individual clones are robotically picked and arranged on a nylon membrane. The membrane is placed on LB agar containing selective agent (carbenicillin, kanamycin, ampicillin, or chloramphenicol depending on the vector used) and incubated at 37 C. for 16 hr. The membrane is removed from the agar and consecutively placed colony side up in 10% SDS, denaturing solution (1.5 M NaCl, 0.5 M NaOH), neutralizing solution (1.5 M NaCl, 1 M Tris, pH 8.0), and twice in 2×SSC for 10 min each. The membrane is then UV irradiated in a STRATALINKER UV-crosslinker (Stratagene).

In the second method, cDNAs are amplified from bacterial vectors by thirty cycles of PCR using primers complementary to vector sequences flanking the insert. PCR amplification increases a starting concentration of 1–2 ng nucleic acid to a final quantity greater than 5 µg. Amplified nucleic acids from about 400 bp to about 5000 bp in length are purified using SEPHACRYL-400 beads (APB). Purified nucleic acids are arranged on a nylon membrane manually or using a dot/slot blotting manifold and suction device and are immobilized by denaturation, neutralization, and UW irradiation as described above. Purified nucleic acids are robotically arranged and immobilized on polymer-coated glass slides using the procedure described in U.S. Pat. No. 5,807, 522. Polymer-coated slides are prepared by cleaning glass microscope slides (Corning, Acton Mass.) by ultrasound in 0.1% SDS and acetone, etching in 4% hydrofluoric acid (VWR Scientific Products, West Chester Pa.), coating with 0.05% aminopropyl silane (Sigma Aldrich) in 95% ethanol, and curing in a 110 C. oven. The slides are washed extensively with distilled water between and after treatments. The nucleic acids are arranged on the slide and then immobilized by exposing the array to UV irradiation using a STRATALINKER UV-crosslinker (Stratagene). Arrays are then washed at room temperature in 0.2% SDS and rinsed three times in distilled water. Non-specific binding sites are blocked by incubation of arrays in 0.2% casein in phosphate buffered saline (PBS; Tropix, Bedford Mass.) for 30 min at 60 C.; then the arrays are washed in 0.2% SDS and rinsed in distilled water as before.

Probe Preparation for Membrane Hybridization

Hybridization probes derived from the cDNAs of the Sequence Listing are employed for screening cDNAs, mRNAs, or genomic DNA in membrane-based hybridizations. Probes are prepared by diluting the cDNAs to a concentration of 40–50 ng in 45 µl TE buffer, denaturing by heating to 100 C. for five min, and briefly centrifuging. The denatured cDNA is then added to a REDIPRIME tube (APB), gently mixed until blue color is evenly distributed, and briefly centrifuged. Five µl of [$^{32}$P]dCTP is added to the tube, and the contents are incubated at 37 C. for 10 min. The labeling reaction is stopped by adding 5 µl of 0.2M EDTA, and probe is purified from unincorporated nucleotides using a PROBEQUANT G-50 microcolumn (APB). The purified probe is heated to 100 C. for five min, snap cooled for two min on ice, and used in membrane-based hybridizations as described below.

Probe Preparation for Polymer Coated Slide Hybridization

Hybridization probes derived from mRNA isolated from samples are employed for screening cDNAs of the Sequence Listing in array-based hybridizations. Probe is prepared using the GEMbright kit (Incyte Genomics) by diluting mRNA to a concentration of 200 ng in 9 µl TE buffer and adding 5 µl 5×buffer, 1 µl 0.1 M DTT, 3 µl Cy3 or Cy5 labeling mix, 1 µl RNase inhibitor, 1 µl reverse transcriptase, and 5 µl 1×yeast control mRNAs. Yeast control mRNAs are synthesized by in vitro transcription from noncoding yeast genomic DNA (W. Lei, unpublished). As quantitative controls, one set of control mRNAs at 0.002 ng, 0.02 ng, 0.2 ng, and 2 ng are diluted into reverse transcription reaction mixture at ratios of 1:100,000, 1:10,000, 1:1000, and 1:100 (w/w) to sample mRNA respectively. To examine mRNA differential expression patterns, a second set of control mRNAs are diluted into reverse transcription reaction mixture at ratios of 1:3, 3:1, 1:10, 10:1, 1:25, and 25:1 (w/w). The reaction mixture is mixed and incubated at 37 C. for two hr. The reaction mixture is then incubated for 20 min at 85 C., and probes are purified using two successive CHROMA SPIN+TE 30 columns (Clontech, Palo Alto Calif.). Purified probe is ethanol precipitated by diluting probe to 90 µl in DEPC-treated water, adding 2 µl 1 mg/ml glycogen, 60 µl 5 M sodium acetate, and 300 µl 100% ethanol. The probe is centrifuged for 20 min at 20,800×g, and the pellet is resuspended in 12 µl resuspension buffer, heated to 65 C. for five min, and mixed thoroughly. The probe is heated and mixed as before and then stored on ice. Probe is used in high density array-based hybridizations as described below.

Membrane-based Hybridization

Membranes are pre-hybridized in hybridization solution containing 1% Sarkosyl and 1×high phosphate buffer (0.5 M NaCl, 0.1 M Na$_2$HPO$_4$, 5 mM EDTA, pH 7) at 55 C. for two hr. The probe, diluted in 15 ml fresh hybridization solution, is then added to the membrane. The membrane is hybridized with the probe at 55 C. for 16 hr. Following hybridization, the membrane is washed for 15 min at 25 C. in 1 mM Tris (pH 8.0), 1% Sarkosyl, and four times for 15 min each at 25 C. in 1 mM Tris (pH 8.0). To detect hybridization complexes, XOMAT-AR film (Eastman Kodak, Rochester N.Y.) is exposed to the membrane overnight at −70 C., developed, and examined visually.

Polymer Coated Slide-based Hybridization

Probe is heated to 65 C. for five min, centrifuged five min at 9400 rpm in a 5415 C. microcentrifuge (Eppendorf Scientific, Westbury N.Y.), and then 18 µl is aliquoted onto the array surface and covered with a coverslip. The arrays are transferred to a waterproof chamber having a cavity just slightly larger than a microscope slide. The chamber is kept at 100% humidity internally by the addition of 140 pi of 5×SSC in a corner of the chamber. The chamber containing the arrays is incubated for about 6.5 hr at 60 C. The arrays are washed for 10 min at 45C. in 1×SSC, 0.1% SDS, and three times for 10 min each at 45 C. in 01×SSC, and dried.

Hybridization reactions are performed in absolute or differential hybridization formats. In the absolute hybridization format, probe from one sample is hybridized to array elements, and signals are detected after hybridization complexes form. Signal strength correlates with probe mRNA levels in the sample. In the differential hybridization format, differential expression of a set of genes in two biological samples is analyzed. Probes from the two samples are prepared and labeled with different labeling moieties. A mixture of the two labeled probes is hybridized to the array elements, and signals are examined under conditions in which the emissions from the two different labels are individually detectable. Elements on the array that are hybridized to substantially equal numbers of probes derived from both biological samples give a distinct combined fluorescence (Shalon WO95/35505).

Hybridization complexes are detected with a microscope equipped with an Innova 70 mixed gas 10 W laser (Coherent, Santa Clara Calif.) capable of generating spectral lines at 488 nm for excitation of Cy3 and at 632 nm for excitation of Cy5. The excitation laser light is focused on the array using a 20X microscope objective (Nikon, Melville N.Y.). The slide containing the array is placed on a computer-controlled X-Y stage on the microscope and raster-scanned past the objective with a resolution of 20 micrometers. In the differential hybridization format, the two fluorophores are sequentially excited by the laser. Emitted light is split, based on wavelength, into two photomultiplier tube detectors (PMT R1477, Hamamatsu Photonics Systems, Bridgewater N.J.) corresponding to the two fluorophores. Appropriate filters positioned between the array and the photomultiplier tubes are used to filter the signals. The emission maxima of the fluorophores used are 565 nm for Cy3 and 650 nm for Cy5. The sensitivity of the scans is calibrated using the signal intensity generated by the yeast control mRNAs added to the probe mix. A specific location on the array contains a complementary DNA sequence, allowing the intensity of the signal at that location to be correlated with a weight ratio of hybridizing species of 1:100,000.

The output of the photomultiplier tube is digitized using a 12-bit RTI-835H analog-to-digital (A/D) conversion board (Analog Devices, Norwood Mass.) installed in an IBM-compatible PC computer. The digitized data are displayed as an image where the signal intensity is mapped using a linear 20-color transformation to a pseudocolor scale ranging from blue (low signal) to red (high signal). The data is also analyzed quantitatively. Where two different fluorophores are excited and measured simultaneously, the data are first corrected for optical crosstalk (due to overlapping emission spectra) between the fluorophores using the emission spectrum for each fluorophore. A grid is superimposed over the fluorescence signal image such that the signal from each spot is centered in each element of the grid. The fluorescence signal within each element is then integrated to obtain a numerical value corresponding to the average intensity of the signal. The software used for signal analysis is the GEMTOOLS program (Incyte Genomics).

VIII Electronic Analysis

BLAST was used to search for identical or related molecules in the GenBank or LIFESEQ databases (Incyte Genomics). The product score for human and rat sequences was calculated as follows: the BLAST score is multiplied by the % nucleotide identity and the product is divided by (5 times the length of the shorter of the two sequences), such that a 100% alignment over the length of the shorter sequence gives a product score of 100. The product score takes into account both the degree of similarity between two sequences and the length of the sequence match. For example, with a product score of 40, the match will be exact within a 1% to 2% error, and with a product score of at least 70, the match will be exact. Similar or related molecules are usually identified by selecting those which show product scores between 8 and 40.

Electronic northern analysis was performed at a product score of 70 as shown in Tables 1 and 2. All sequences and cDNA libraries in the LIFESEQ database were categorized by system, organ/tissue and cell type. The categories included cardiovascular system, connective tissue, digestive system, embryonic structures, endocrine system, exocrine glands, female and male genitalia, germ cells, hemic/immune system, liver, musculoskeletal system, nervous system, pancreas, respiratory system, sense organs, skin, stomatognathic system, unclassified/mixed, and the urinary tract. For each category, the number of libraries in which the sequence was expressed were counted and shown over the total number of libraries in that category. In a non-normalized library, expression levels of two or more are significant.

IX Complementary Molecules

Molecules complementary to the cDNA, from about 5 (PNA) to about 5000 bp (complement of a cDNA insert), are used to detect or inhibit gene expression. These molecules are selected using OLIGO 4.06 software (National Biosciences). Detection is described in Example VII. To inhibit transcription by preventing promoter binding, the complementary molecule is designed to bind to the most unique 5' sequence and includes nucleotides of the 5' UTR upstream of the initiation codon of the open reading frame. Complementary molecules include genomic sequences (such as enhancers or introns) and are used in "triple helix" base pairing to compromise the ability of the double helix to open sufficiently for the binding of polymerases, transcription factors, or regulatory molecules. To inhibit translation, a complementary molecule is designed to prevent ribosomal binding to the mRNA encoding the mammalian protein.

Complementary molecules are placed in expression vectors and used to transform a cell line to test efficacy; into an organ, tumor, synovial cavity, or the vascular system for transient or short term therapy; or into a stem cell, zygote, or other reproducing lineage for long term or stable gene therapy. Transient expression lasts for a month or more with a non-replicating vector and for three months or more if appropriate elements for inducing vector replication are used in the transformation/expression system.

Stable transformation of appropriate dividing cells with a vector encoding the complementary molecule produces a transgenic cell line, tissue, or organism (U.S. Pat. No. 4,736,866). Those cells that assimilate and replicate sufficient quantities of the vector to allow stable integration also produce enough complementary molecules to compromise or entirely eliminate activity of the cDNA encoding the mammalian protein.

X Expression of SPARC-1 and SPARC-2

Expression and purification of the mammalian protein are achieved using either a mammalian cell expression system or an insect cell expression system. The pUB6/NV5-His vector system (Invitrogen, Carlsbad Calif.) is used to express SPARC-1 or SPARC-2 in CHO cells. The vector contains the selectable bsd gene, multiple cloning sites, the promoter/enhancer sequence from the human ubiquitin C gene, a C-terminal V5 epitope for antibody detection with anti-V5 antibodies, and a C-terminal polyhistidine (6×His) sequence for rapid purification on PROBOND resin (Invitrogen). Transformed cells are selected on media containing blasticidin.

*Spodoptera frugiperda* (Sf9) insect cells are infected with recombinant *Autographica californica* nuclear polyhedrosis virus (baculovirus). The polyhedrin gene is replaced with the mammalian cDNA by homologous recombination and the polyhedrin promoter drives cDNA transcription. The protein is synthesized as a fusion protein with 6×his which enables purification as described above. Purified protein is used in the following activity and to make antibodies.

XI Production of Antibodies

SPARC-1 and SPARC-2 are purified using polyacrylamide gel electrophoresis and used to immunize mice or rabbits. Antibodies are produced using the protocols below. Alternatively, the amino acid sequences of SPARC-1 and SPARC-2 are analyzed using LASERGENE software (DNASTAR) to determine regions of high antigenicity. An antigenic epitope, usually found near the C-terminus or in a hydrophilic region is selected, synthesized, and used to raise antibodies. Typically, epitopes of about 15 residues in length are produced using an ABI 431 A peptide synthesizer (Applied Biosystems) using Fmoc-chemistry and coupled to KLH (Sigma-Aldrich) by reaction with N-maleimidobenzoyl-N-hydroxysuccinimide ester to increase antigenicity.

Rabbits are immunized with the epitope-KLH complex in complete Freund's adjuvant. Immunizations are repeated at intervals thereafter in incomplete Freund's adjuvant. After a minimum of seven weeks for mouse or twelve weeks for rabbit, antisera are drawn and tested for antipeptide activity. Testing involves binding the peptide to plastic, blocking with 1% bovine serum albumin, reacting with rabbit antisera, washing, and reacting with radio-iodinated goat anti-rabbit IgG. Methods well known in the art are used to determine antibody titer and the amount of complex formation.

XII Purification of Naturally Occurring Protein Using Specific Antibodies

Naturally occurring or recombinant protein is purified by immunoaffinity chromatography using antibodies which specifically bind the protein. An immunoaffinity column is constructed by covalently coupling the antibody to CNBr-activated SEPHAROSE resin (APB). Media containing the protein is passed over the immunoaffinity column, and the column is washed using high ionic strength buffers in the presence of detergent to allow preferential absorbance of the protein. After coupling, the protein is eluted from the column using a buffer of pH 2–3 or a high concentration of urea or thiocyanate ion to disrupt antibody/protein binding, and the protein is collected.

XIII Screening Molecules for Specific Binding with the cDNA or Protein

The cDNA, or fragments thereof, or the protein, or portions thereof, are labeled with $^{32}$P-dCTP, Cy3-dCTP, or Cy5-dCTP (APB), or with BIODIPY or FIHTC (Molecular Probes, Eugene Oreg.), respectively. Libraries of candidate molecules or compounds previously arranged on a substrate are incubated in the presence of labeled cDNA or protein. After incubation under conditions for either a nucleic acid or amino acid sequence, the substrate is washed, and any position on the substrate retaining label, which indicates specific binding or complex formation, is assayed, and the ligand is identified. Data obtained using different concentrations of the nucleic acid or protein are used to calculate affinity between the labeled nucleic acid or protein and the bound molecule.

XIV Two-Hybrid Screen

A yeast two-hybrid system, MATCHMAKER LexA Two-Hybrid system (Clontech Laboratories, Palo Alto Calif.), is used to screen for peptides that bind the mammalian protein of the invention. A cDNA encoding the protein is inserted into the multiple cloning site of a pLexA vector, ligated, and transformed into E. coli. cDNA, prepared from mRNA, is inserted into the multiple cloning site of a pB42AD vector, ligated, and transformed into E. coli to construct a cDNA library. The pLexA plasmid and pB42AD-cDNA library constructs are isolated from E. coli and used in a 2:1 ratio to co-transform competent yeast EGY48[p8op-lacZ] cells using a polyethylene glycol/lithium acetate protocol. Transformed yeast cells are plated on synthetic dropout (SD) media lacking histidine (-His), tryptophan (-Trp), and uracil (-Ura), and incubated at 30 C. until the colonies have grown up and are counted. The colonies are pooled in a minimal volume of 1×TE (pH 7.5), replated on SD/-His/-Leu/-Trp/-Ura media supplemented with 2% galactose (Gal), 1% raffinose (Raf), and 80 mg/ml 5-bromo-4-chloro-3-indolyl β-d-galactopyranoside (X-Gal), and subsequently examined for growth of blue colonies. Interaction between expressed protein and cDNA fusion proteins activates expression of a LEU2 reporter gene in EGY48 and produces colony growth on media lacking leucine (-Leu). Interaction also activates expression of β-galactosidase from the p8op-lacZ reporter construct that produces blue color in colonies grown on X-Gal.

Positive interactions between expressed protein and cDNA fusion proteins are verified by isolating individual positive colonies and growing them in SD/-Trp/-Ura liquid medium for 1 to 2 days at 30 C. A sample of the culture is plated on SD/-Trp/-Ura media and incubated at 30 C. until colonies appear. The sample is replica-plated on SD/-Trp/-Ura and SD/-His/-Trp/-Ura plates. Colonies that grow on SD containing histidine but not on media lacking histidine have lost the pLexA plasmid. Histidine-requiring colonies are grown on SD/Gal/Raf/X-Gal/-Trp/-Ura, and white colonies are isolated and propagated. The pB42AD-cDNA plasmid, which contains a cDNA encoding a protein that physically interacts with the mammalian protein, is isolated from the yeast cells and characterized.

XV SPARC-1 and SPARC-2 Assays

"SPARC-like activity of SPARC-1 or SPARC-2 is determined in ligand-binding assays using candidate ligand molecules, such as PDGF, VEGF, collagen, or other proteins that bind to SPARC. The protein is labeled with $^{125}$I Bolton-Hunter reagent (Bolton and Hunter (1973) Biochem J 133:529–539). Candidate molecules, previously arrayed in wells of a multi-well plate, are incubated with the labeled SPARC-1 or SPARC-2, washed, and any wells with labeled SPARC-1 or SPARC-2 complex are assayed. Data obtained using different concentrations of SPARC-1 or SPARC-2 are used to calculate values for the number, affinity, and association of SPARC-1 or SPARC-2 with the candidate molecules.

All patents and publications mentioned in the specification are incorporated by reference herein. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the field of molecular biology or related fields are intended to be within the scope of the following claims.

TABLE 1A

| Tissue Category | Clone Count | Found in | Abs Abund | Pct Abund |
|---|---|---|---|---|
| Cardiovascular System | 253105 | 8/64 | 14 | 0.0055 |
| Connective Tissue | 134008 | 6/41 | 9 | 0.0067 |
| Digestive System | 447016 | 18/130 | 33 | 0.0074 |
| Embryonic Structures | 106591 | 4/21 | 7 | 0.0066 |
| Endocrine System | 210781 | 1/50 | 1 | 0.0005 |
| Exocrine Glands | 252458 | 16/61 | 25 | 0.0099 |
| Reproductive, Female | 392343 | 25/92 | 48 | 0.0122 |
| Reproductive, Male | 430286 | 17/109 | 46 | 0.0107 |
| Germ Cells | 36677 | 0/5 | 0 | 0.0000 |
| Hemic and Immune System | 662225 | 4/153 | 7 | 0.0011 |
| Liver | 92176 | 1/25 | 2 | 0.0022 |
| Musculoskeletal System | 154504 | 10/44 | 18 | 0.0117 |
| Nervous System | 904527 | 16/185 | 24 | 0.0027 |
| Pancreas | 100545 | 2/21 | 5 | 0.0050 |
| Respiratory System | 362922 | 10/83 | 12 | 0.0033 |
| Sense Organs | 19253 | 1/8 | 1 | 0.0052 |
| Skin | 72082 | 2/15 | 2 | 0.0028 |
| Stomatognathic System | 10988 | 0/4 | 0 | 0.0000 |

TABLE 1A-continued

| Tissue Category | Clone Count | Found in | Abs Abund | Pct Abund |
|---|---|---|---|---|
| Unclassified/Mixed | 103494 | 1/8 | 1 | 0.0010 |
| Urinary Tract | 252077 | 11/57 | 11 | 0.0044 |
| Totals | 4998058 | 153/1176 | 266 | 0.0053 |

TABLE 2A-continued

| Tissue Category | Clone Count | Found in | Abs Abund | Pct Abund |
|---|---|---|---|---|
| Hemic and Immune System | 662225 | 3/153 | 6 | 0.0009 |
| Liver | 92176 | 4/25 | 6 | 0.0065 |
| Musculoskeletal System | 154504 | 3/44 | 4 | 0.0026 |
| Nervous System | 904527 | 31/185 | 51 | 0.0056 |
| Pancreas | 100545 | 1/21 | 1 | 0.0010 |

TABLE 1B

Found in:

| Library ID | Clone Count | Library Description | Abs Abund | Pct Abund |
|---|---|---|---|---|
| STOMTUP02 | 18163 | stomach tumor, adenoCA, poorly differentiated, 3' CGAP | 11 | 0.0606 |
| GBLANOT02 | 3444 | gallbladder, cholecystitis, cholelithiasis, 21M | 2 | 0.0581 |
| BRSTTMT02 | 3241 | breast, PF changes, mw/multifocal ductal CA in situ, 46F | 2 | 0.0617 |
| BRSTTUT15 | 6539 | breast tumor, adenoCA, 46F, m/BRSTNOT17 | 4 | 0.0612 |
| BRSTTMC01 | 4491 | breast, NF changes, mw/ductal adenoCA, 40-57F, pool, 1g cDNA | 2 | 0.0445 |
| BRSTTUT02 | 7099 | breast tumor, adenoCA, 54F, m/BRSTNOT03 | 3 | 0.0423 |
| PROSTUS23 | 7712 | prostate tumor, adenoCA, 58, 61, 66, 68M, pool, SUB | 16 | 0.2075 |
| PROSTUT04 | 8552 | prostate tumor, adenoCA, 57M, m/PROSNOT06 | 3 | 0.0351 |
| CARGDIT02 | 3440 | cartilage, OA, M/F | 5 | 0.1453 |
| CARGDIT01 | 7235 | cartilage, OA | 3 | 0.0415 |
| SYNORAB01 | 5131 | synovium, hip, rheuA, 68F | 2 | 0.0390 |
| BRAITUT26 | 1665 | brain tumor, posterior fossa, meningioma, 70M | 1 | 0.0601 |
| BRAIDIT01 | 3669 | brain, multiple sclerosis | 2 | 0.0545 |
| MENITUT03 | 4010 | brain tumor, benign meningioma, 35F | 2 | 0.0499 |
| BRAITUT07 | 6246 | brain tumor, frontal, neuronal neoplasm, 32M | 3 | 0.0480 |
| NGANNOT01 | 13628 | neuroganglion tumor, ganglioneuroma, 9M | 3 | 0.0220 |

TABLE 2A

| Tissue Category | Clone Count | Found in | Abs Abund | Pct Abund |
|---|---|---|---|---|
| Cardiovascular System | 253105 | 1/64 | 1 | 0.0004 |
| Connective Tissue | 134008 | 3/41 | 3 | 0.0022 |
| Digestive System | 447016 | 1/130 | 1 | 0.0002 |
| Embryonic Structures | 106591 | 1/21 | 2 | 0.0019 |
| Endocrine System | 210781 | 4/50 | 5 | 0.0024 |
| Exocrine Glands | 252458 | 4/61 | 5 | 0.0020 |
| Reproductive, Female | 392343 | 3/92 | 6 | 0.0015 |
| Reproductive, Male | 430286 | 13/109 | 19 | 0.0044 |
| Germ Cells | 36677 | 1/5 | 5 | 0.0136 |

TABLE 2A-continued

| Tissue Category | Clone Count | Found in | Abs Abund | Pct Abund |
|---|---|---|---|---|
| Respiratory System | 362922 | 0/83 | 0 | 0.0000 |
| Sense Organs | 19253 | 0/8 | 0 | 0.0000 |
| Skin | 72082 | 0/15 | 0 | 0.0000 |
| Stomatognathic System | 10988 | 0/4 | 0 | 0.0000 |
| Unclassified/Mixed | 103494 | 3/8 | 4 | 0.0039 |
| Urinary Tract | 252077 | 0/57 | 0 | 0.0000 |
| Totals | 4998058 | 76/1176 | 119 | 0.0024 |

TABLE 2B

Found in:

| Library ID | Clone Count | Library Description | Abs Abund | Pct Abund |
|---|---|---|---|---|
| HELATXT01 | 3900 | cervical tumor line, HeLa, adenoCA, 31F, t/TNF, IL-1 | 4 | 0.1026 |
| HELATUM01 | 4033 | cervical tumor line, HeLa S3, adenoCA, 31F, untreated, WM/WN | 1 | 0.0248 |
| HELAUNT01 | 4089 | cervical tumor line, HeLa, adenoCA, 31F, untreated | 1 | 0.0245 |
| PROSTUS19 | 4087 | prostate tumor, adenoCA, 59M, SUB, m/PROSNOT19 | 2 | 0.0489 |
| LIVRTMR01 | 2673 | liver, mw/mets neuroendocrine CA, 62F, RP, m/LIVRTUT13 | 2 | 0.0748 |
| BRAITUT12 | 7273 | brain tumor, frontal, astrocytoma, 40F, m/BRAINOT14 | 6 | 0.0825 |
| BRAITUT01 | 7218 | brain tumor, frontal, oligoastrocytoma, 50F | 2 | 0.0277 |
| BRAITUP02 | 14513 | brain tumor, glioblastama, pool, NORM, CGAP | 4 | 0.0276 |
| BRAYDIN03 | 7635 | brain, hypothalamus, Huntington's, mw/CVA, 57M, NORM | 2 | 0.0262 |
| BRAITUP03 | 21644 | brain tumor, anaplastic oligodendroglioma, pool, NORM, CGAP | 5 | 0.0231 |
| NERVMSM01 | 8643 | multiple sclerosis, 46M, NORM, WM/WN | 2 | 0.0231 |

Not found in:

| Library ID | Clone Count | Library Description |
|---|---|---|
| LIVRTUT13 | 10424 | liver tumor, mets neuroendocrine CA, 62F, m/LIVRTMRO1 |

What is claimed is:

1. An isolated cDNA encoding a protein comprising SEQ ID NO:2 or the complement of the encoding cDNA.

2. An isolated cDNA comprising a nucleic acid sequence of SEQ ID NO:20 or the complement of SEQ ID NO:20.

3. A composition comprising the cDNA or the complement of the cDNA of claim 1.

4. A substrate comprising the cDNA or the complement of the cDNA of claim 1.

5. A probe comprising the cDNA or the complement of the cDNA of claim 1.

6. A vector comprising the cDNA of claim 1.

7. A host cell comprising the vector of claim 6.

8. A method for producing a protein, the method comprising:

a) culturing the host cell of claim 7 under conditions for protein expression; and b) recovering the protein from the host cell culture.

9. A method for using a cDNA to detect the differential expression of a nucleic acid in a sample comprising:

a) hybridizing the probe of claim 5 to the nucleic acids, thereby forming hybridization complexes; and b) comparing hybridization complex formation with a standard, wherein the comparison indicates the differential expression of the cDNA in the sample.

10. The method of claim 9 further comprising amplifying the nucleic acids of the sample prior to hybridization.

11. A method of using a cDNA to screen a plurality of molecules or compounds, the method comprising:
  a) combining the cDNA of claim 1 with a plurality of molecules or compounds under conditions to allow specific binding; and
  b) detecting specific binding, thereby identifying a molecule or compound which specifically binds the cDNA.

12. The method of claim 11 wherein the molecules or compounds are selected from DNA molecules, RNA molecules, peptide nucleic acids, artificial chromosome constructions, peptides, transcription factors, repressors, and regulatory molecules.

* * * * *